United States Patent
Garbán

(10) Patent No.: US 12,252,525 B2
(45) Date of Patent: Mar. 18, 2025

(54) CHIMERIC T CELL RECEPTORS, NUCLEIC ACIDS, AND METHODS OF MAKING AND USING THE SAME

(71) Applicant: NantBio, Inc., Culver City, CA (US)

(72) Inventor: Hermes Garbán, Los Angeles, CA (US)

(73) Assignee: NantBio, Inc., Culver City, CA (US)

( * ) Notice: Subject to any disclaimer, the term of this patent is extended or adjusted under 35 U.S.C. 154(b) by 268 days.

(21) Appl. No.: 17/387,347

(22) Filed: Jul. 28, 2021

(65) Prior Publication Data

US 2022/0033459 A1 Feb. 3, 2022

Related U.S. Application Data

(60) Provisional application No. 63/059,560, filed on Jul. 31, 2020.

(51) Int. Cl.
  *C07K 14/725* (2006.01)
  *A61K 39/00* (2006.01)
  *C07K 14/705* (2006.01)

(52) U.S. Cl.
  CPC ...... *C07K 14/7051* (2013.01); *A61K 39/4613* (2023.05); *A61K 39/4631* (2023.05); *A61K 39/4644* (2023.05); *C07K 14/70521* (2013.01); *A61K 2239/26* (2023.05); *C07K 2317/622* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 2016/0046700 A1* | 2/2016 | Foster | C07K 14/70578 424/134.1 |
| 2017/0008947 A1* | 1/2017 | Spencer | C07K 14/70521 |
| 2018/0186878 A1* | 7/2018 | Rosenthal | C07K 16/244 |
| 2019/0085081 A1* | 3/2019 | Bicknell | C07K 16/2851 |
| 2020/0129552 A1* | 4/2020 | Klingemann | C07K 14/4702 |

FOREIGN PATENT DOCUMENTS

| | | | |
|---|---|---|---|
| CN | 110079504 A | 8/2019 | |
| WO | 2017/158337 A1 | 9/2017 | |
| WO | WO-2019089813 A1 * | 5/2019 | ............ A61K 35/17 |
| WO | 2019/222579 A1 | 11/2019 | |
| WO | 2020/061337 A1 | 3/2020 | |
| WO | 2020/096646 A1 | 5/2020 | |

OTHER PUBLICATIONS

Van de Winkel, J. G., Ernst, L. K., Anderson, C. L., & Chiu, I. M. (1991). Gene organization of the human high affinity receptor for IgG, Fc gamma RI (CD64). Characterization and evidence for a second gene. Journal of Biological Chemistry, 266(20), 13449-13455. (Year: 1991).*
International Search Report issued in PCT/US2021/043499 issued Dec. 6, 2021.
Written Opinion issued in PCT/US2021/043499 issued Dec. 6, 2021.

* cited by examiner

*Primary Examiner* — Christopher M Babic
*Assistant Examiner* — Kimberly A Aron
(74) *Attorney, Agent, or Firm* — Harness Dickey & Pierce P.L.C.

(57) ABSTRACT

Compositions and methods for eradicating tumor cells using novel compositions are contemplated. In one aspect, a pharmaceutical composition comprising a CAR scaffold and an antigen binding domain in a single chimeric species is provided. In some aspects, the CAR scaffold may comprise a CD28 costimulatory signaling region and a CD3ζ activation domain or a complete CD3ζ activation domain. In some aspects, the CAR scaffold may be codon-optimized for improved expression in mammalian cell lines and/or for improved function upon transfection into natural killer (NK) or other immune cells. In further aspects, the antigen binding domain may comprise a VL and VH domain linked by a spacer and may be codon optimized. A CD64 leader sequence may be attached to the antigen binding domain, e.g., at the N-terminus of the antigen binding domain.

27 Claims, 68 Drawing Sheets

Specification includes a Sequence Listing.

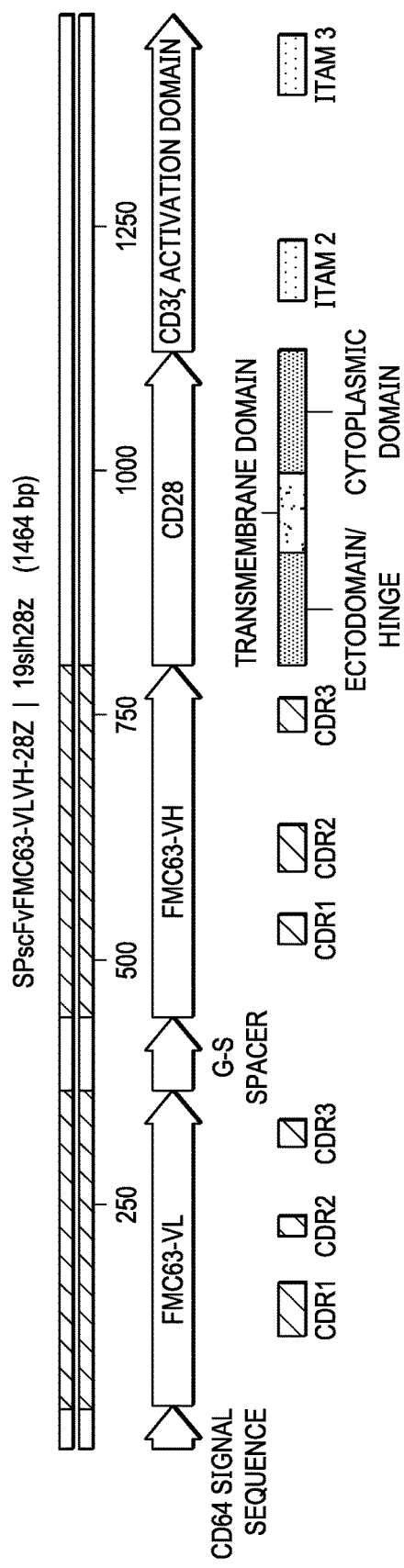
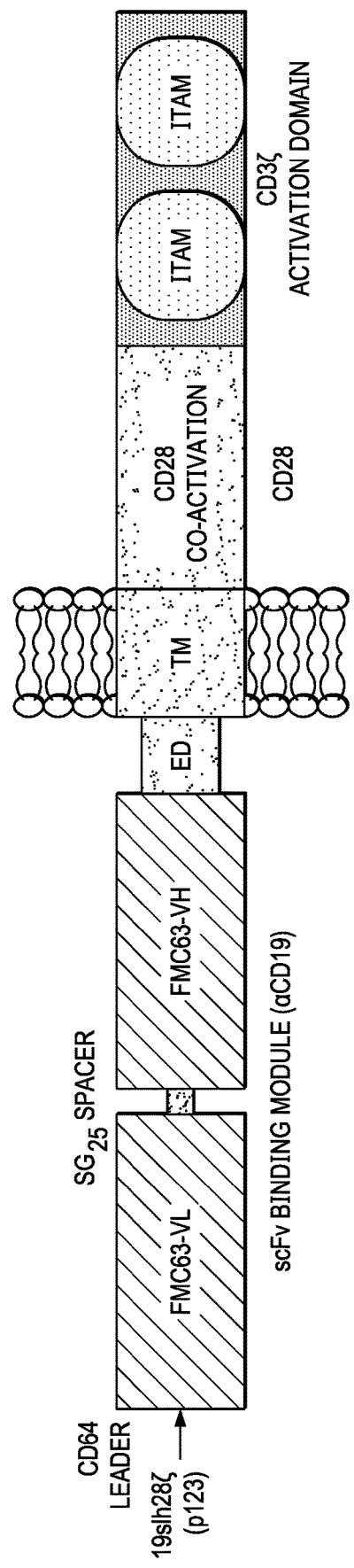
FIG. 3A
FIG. 3B

>SPscFvFMC63-VLVH-28Z | 19slh28z.dna (1464 bp)

CD64 LEADER SEQUENCE:
ATGTGGTTTCTTACTACACATTGCTGTTGTGGGTCCCGGTGGACGGT (SEQ ID NO.:1)

VARIABLE REGION:
GACATCCAGATGACACAGACTACATCCTCCCTGTCTGCCTCTCTGGGAGACAGAGTCACCATCAGTTGCAGGGCAAGTCAGGACATTA
GTAAATATTTAAATTGGTATCAGCAGAAACCAGATGGAACTGTTAAACTCCTGATCTACCATACATCAAGATTACACTCAGGAGTCCC
ATCAAGGTTCAGTGGCAGTGGGTCTGGAACAGATTATTCTCTCACCATTAGCAACCTGGAGCAAGAAGATATTGCCACTTACTTTTGC
CAACAGGGTAATACGCTTCCGTACACGTTCGGAGGGGGGACTAAGTTGGAAATAACA (SEQ ID NO.:2)

G-S SPACER:
TCCTCAGGGGGCGGGGGAAGTGGTGGGGCGGCAGCGGCGGCGAGGGGCTCAGGAGGAGGGGCTCAGGAGGAGGCGGATCAGGCGGATCA (SEQ ID NO.:3)

VARIABLE REGION:
GAGGTGAAACTGCAGGAGTCAGGACCTGGCCTGGTGGCGCCCTCACAGAGCCTGTCCGTCACTGCACTGTCTCAGGGGTCTCATT
ACCCGACTATGTGTAAGCTGGATTCGCCAGCCTCCAGGAAAGGGTCTGGAGTGGCTGGGAGTAATATGGGTAGTGAAACCACAT
ACTATAATTCAGCTCTCAAATCCAGACTGACCATCATCAAGGACAACTCCAAGAGCCAAGTTTTCTTAAAAATGAACAGTCTGCAA
ACTGATGACACAGCCATTACTACTGTGCCAAACATTATTACTACGGTGTAGCTATGCTATGGACTACTGGGGTCAAGGAACCTC
AGTCACCGTCTCCTCA (SEQ ID NO.:4)

ECTO, TRANSMEMBRANE AND SIGNALING DOMAIN:
ATTGAAGTTATGTATCCTCCTCCTTACCTAGACAATGAGAAGAGCAATGGAACCATTATCCATGTGAAGGGAAAACACCTTGTCCAA
GTCCCGTATTCCGGGACCTTCTAAGGCCCTTTGGGTGCTGGTGGTGGTCGGAGTCCTGGCTTGCTATAGCTTGCTAGTAACAGT
GGGTTTATTATTTGTGAGGAGTAAGAGGAGCAGGCTCCTGCACAGTGACTACATGAACATGACTCCCCGGCGCCCCGGGCCC
ACCCGCAAGCATTACCAGCCCTATGCCCCACCACGCGACTTCGCAGCCTATCGCTCCAGATGAAGTTCAGAGTGAAGTACGACGT
CCGGAGCAAGCGGAGAGAGGCAGGGCAGGCGGGCCACAAGCCTCTGTATAACGAGCTCAATCTAGGACGAAGAGAGGAGTACGATG
TTTTGGACAAGAGAAGAGGACGTGGCCTGGAAAGATAAGATGGCAGAAGCCTACAGTGAGATTGGGATGAAAGGCGAGCGCCGGAGG
GGCAAGGGGCACGATGGCCTTTACCAGGGTCTCAGTACAGCCACCAAGGACACCTACGATGCCCTTCACATGCAGGCCCTGCCCCCT
CGCTAA (SEQ ID NO.:5)

FIG. 4

>CD19-SPscFvFMC63.dna (801 bp)

CD64 LEADER SEQUENCE:
ATGTGGTTTCTTACTACACATTGCTGTTGTGGGTCCCGGTGACGGT (SEQ ID NO.: 1)

VARIABLE REGION:
GACATCCAGATGACACAGACTACATCCTCCCTGTCTGCCTCTCTGGGAGACAGAGTCACCATCAGTTGCAGGGCAAGTCAGGAC
ATTAGTAAATATTTAAATTGGTATCAGCAGAAACCAGATGGAACTGTTAAACTCCTGATCTACCATACATCAAGATTACACTCA
GGAGTCCCATCAAGGTTCAGTGGCAGTGGGTCTGGAACAGATTATTCTCTCACCATTAGCAACCTGGAGCAAGAAGATATTGCC
ACTTACTTTTGCCAACAGGGTAATACGCTTCCGTACACGTTCGGAGGGGGGACTAAGTTGGAAATAACA (SEQ ID NO.: 2)

G-S SPACER:
TCCTCAGGGGCGGGGGAAGTGGTGGGGGGCAGCGGCGGAGGGGGCTCAGGAGGAGGCGGATCAGGCGGATCA (SEQ ID NO.: 3)

VARIABLE REGION:
GAGGTGAAACTGCAGGAGTCAGGACCTGGCCTGGTGGCGCCCTCACAGAGCCTGTCCGTCACTGTCTCAGGGTCTCA
TTACCCGACTATGTGGTGTAAGCTGGATTCGCCAGCCTCCAGGAAAGGGTCTGGAGTGGCTGGGAGTAATATGGGGTAGTGAAACC
ACATACTATAATTCAGCTCTCAAATCCAGACTGACCATCATCAAGGACAACTCCAAGAGCCAAGTTTTCTTAAAAATGAACAGT
CTGCAAACTGATGACACAGCCATTTACTACTGTGCCAAACATTATTACTACGGTGGTAGCTATGCTATGGACTACTGGGGTCAA
GGAACCTCAGTCACCGTCTCCTCA (SEQ ID NO.: 4)

FIG. 5

```
FEATURES             Location/Qualifiers
     SOURCE          1..267
                     /organism="unspecified"
     REGION          1..15
                     /label=CD64 signal sequence
     REGION          16..122
                     /label=FMC63-VL
     REGION          123..147
                     /label=G-S Spacer
     REGION          148..267
                     /label=FMC63-VH ORIGIN
    1 mwflttlllw vpvdgdiqmt qttslsasl gdrvtiscra sqdiskylnw yqqkpdgtvk
   61 llyhtsrlh sqvpsrfsgs gsgtdysltl snleqediat yfcqqgntlp ytfgggtkle
  121 itssggggsg ggsggggsg gggsggs evk lqesgpglva psqslsvtct vsgvsipdyg
  181 vswirqppek glewlgviwg settyynsal ksrltlikdn sksqvflkmn slqtddtaly
  241 ycakhyygg syamdywgqg tsvtvss (SEQ ID NO.: 6)
```

FIG. 6

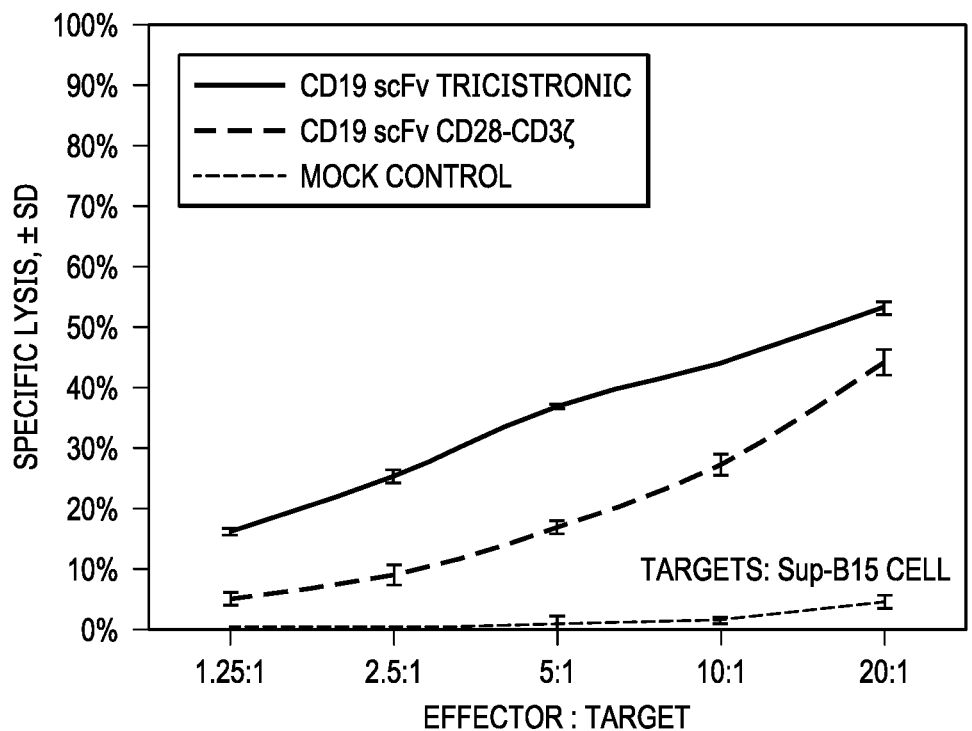
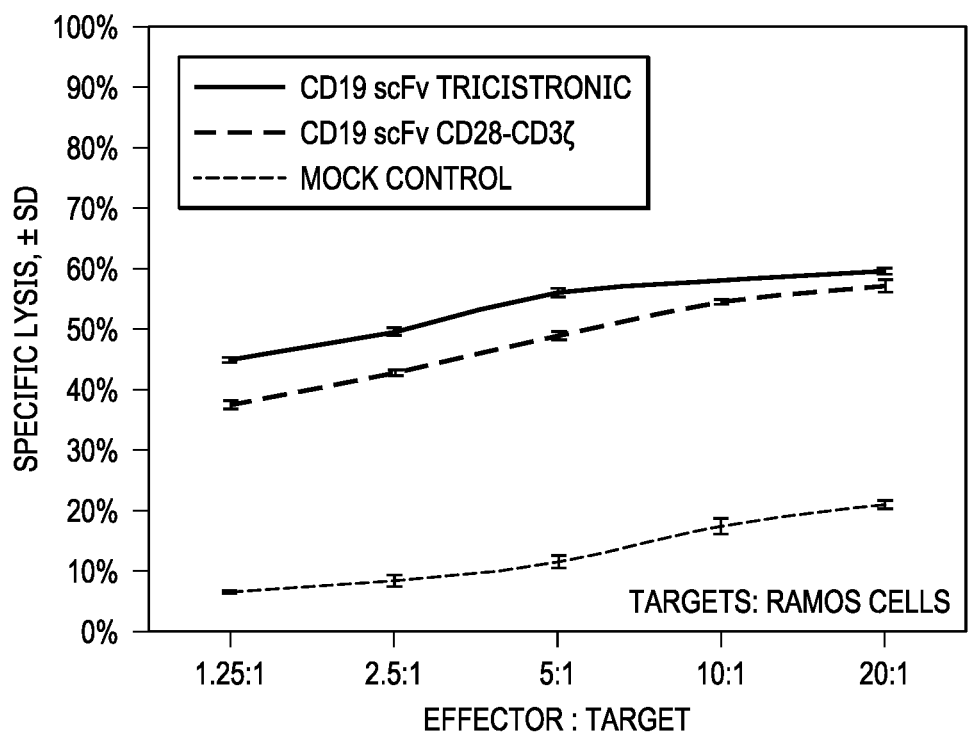

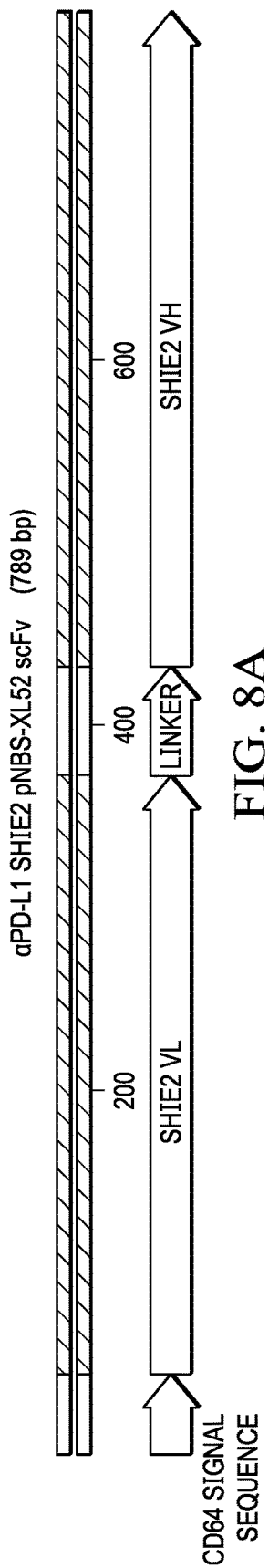

FIG. 8A

>αPD-L1 SHIE2 pNBS-XL52 scFv.dna (789 bp)

LEADER SEQUENCE:
ATGTGGTTTCTTACTACACATTGCTGTTGTGGGTCCCGGTGGACGGT (SEQ ID NO.: 1)

VARIABLE REGION:
CAGTCTGCCCTGACTCAGCCTGCCTCCGTGTCTGGGTCTCTTGGACAGTCAGTCACCATCTCCTGCACTGGAAGCAGCAGTGATGT
TGGGAGTTATAACCTTGTCTCTTGGTACCAACAGCACCCCAGGCAAAGCCCCCAAATCTCATGATTTATGATGTCAGTAAGCGGTCAG
GGGTTTCTAATCGCTTCTCTGGCTCCAAGTCTGGCAACACGGCCTCCCTGACCATCTCTGGGCTCCAGGCTGAGGACGAGGCTGAT
TATTACTGCAGCTCATATACAGGCGTATTCGGCGGAGGGACCAAGCTGACCGTCCTG (SEQ ID NO.: 7)

LINKER:
GGCGGGCGGAGGAAGCGGAGGCGGAGGATCTGGGGGCGGAGGCTCTGGGCGGAGGGGGATCT (SEQ ID NO.: 8)

VARIABLE REGION:
GAGGTGCAGCTGGTGGAGTCTGGGGGAGGCTTGGTGAAGAAGCCTGGGGTCTCCTGCAAGGCTTCTGGAGGCACCTT
CAGCAGCTATGCTATCAGCTGGGTGCGACAGGCCCCTGGACAAGGGCTTGAGTGATGGGAGGGATCATCCCTATCTTTGGTACAG
CAAACTACGCACAGAAGTTCCAGGGCAGAGTCACGATTACCGCGGACGAATCCACGAGCACAGCCTACATGGAGCTGAGCAGCCTG
AGATCTGAGGACACGGCCGTGTATTACTGTGCGAGAGCCCCGTGTACTACTACTACTGGGGCCAAGGGACCACGGT
CACCGTGAGCTCA (SEQ ID NO.: 9)

FIG. 8B

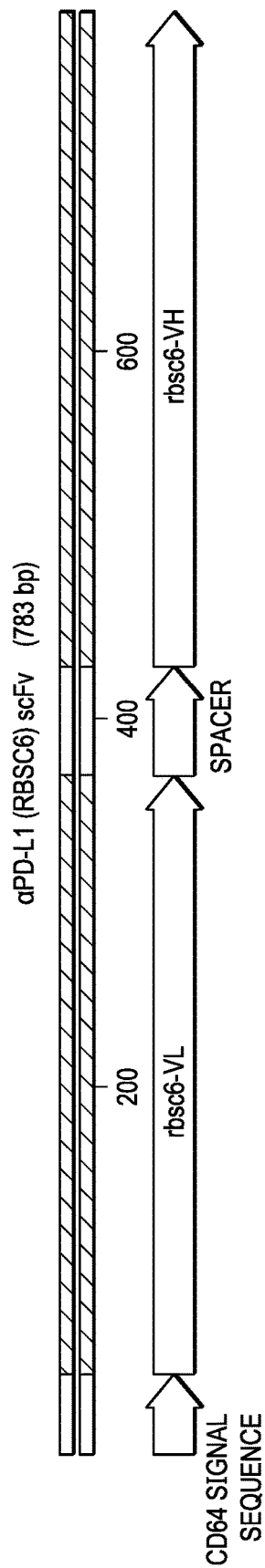

FIG. 9A

>αPD-L1 (RBSC6) scFv.dna (783 bp)

LEADER SEQUENCE:
ATGTGGTTTCTTACTACACATTGCTGTTGTGGGTCCCGGGTGGACGGT (SEQ ID NO.: 1)

VARIABLE REGION:
AACATCCAGATGACCCAGTCTCCATCTCTGTGTCTGCATCTGTAGGAGACAGAGTCACCATCACTTGTCGGGCGAGTCAGGATA
TTAGCCGCTACTTAGCCTGGTATCAGCAGAAACCAGGGAAAGCCCCTAAACTCCTGATCTATGCTGCATCCAGTTTGCAAAGTGG
GGTCCCATCGAGGTTCAGCGGCAGTGGATCTGGGACAGATTTCGCTCTCACTATCAGCAGCCTGAAGATTTTGCAACT
TACTATTGTCAACAGGCTGACAGTGTCGTTTCTCGATCACCTTCGGCCAAGGGACACGACTGGAGATTAAAGGC (SEQ ID NO.: 10)

LINKER:
GGCGGAGGAAGCGGAGGCCGGAGGATCTGGGGGCGGAGGCTCTGGCCGGAGGGGGATCT (SEQ ID NO.: 11)

VARIABLE REGION:
GAGGTGCAGCTGGTGCAGTCTGGGGGAGGCTTGGTACAGCCTGGGGGGTCCCTGAGACTCTCCTGTGCAGCCTCTGGATTCACCT
TCAGTAGCTATAGCATGAACTGGGTCCGCCAGGCTCCAGGGAAGGGGCTGGAGTGGGTTTCATACATTAGTAGTAGTAGTAC
CATACAGTACGCAGACTCTGTGAAGGGCCGATTCACCATCTCCAGAGACAATGCCAAGAACACTCACTGTATCTGCAAATGAACAGC
CTGAGAGACGAGGACACAGGGCTGTATTACTGTGCGGAGAGGGACTACTACGGTATGGACGTCTGGGGCCAAGGGACCACGG
TCACCGTGAGCTCA (SEQ ID NO.: 12)

FIG. 9B

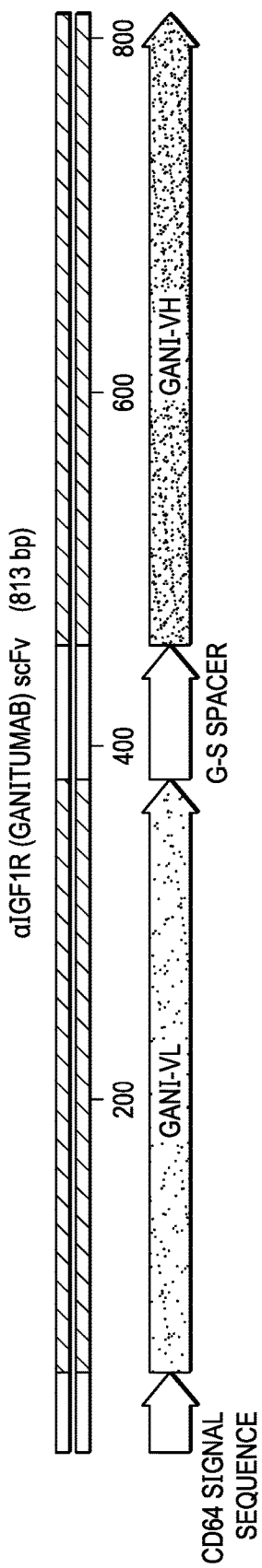

FIG. 11A

>αIGF1R (GANITUMAB) scFv.dna (813 bp)

LEADER CONSTRUCT:
ATGTGGTTTCTTACTACAATTGCTGTTGTGGGGTCCCGGTGGACGGGT (SEQ ID NO.: 1)

VARIABLE REGION:
GATGTTGTAATGACGACAGTCACCTCCGGTCACACCCGGAGAACCAGCGTCAATTAGCTGCGATCTAGCCAAAGTTT
GCTTCATTCCAATGGTTACAATTATCTGACTGTTACTTGCAGAAACCCGGCCAATCCCTCAGCTGCTCATCTACCTTGGGTCTA
ATAGGGCATCTGGGGTTCCCGATAGGTTCTCTGGCTCCGGAGCGGCACCGACTTTACGTTGAAAATCTCTAGGGTTGAGGCGGAA
GACGTAGGCGTTTACTATTGCATGCAGGGGACCCACTGGCCGCTGACCTTCGGCCAGGCACCAAGGTTGAAATAAAA
(SEQ ID NO: 13)

LINKER REGION:
TCCTCAGGAGGGGGGGGAAGTGGTGGGGGCAGCGGCGGGAGGGGGGCTCAGGAGGAGGAGGCGGATCA (SEQ ID NO: 30)

VARIABLE REGION:
GGCGGAGATCACAGGTACAGCTCCAGGAATCAGGACCCGGTTTGGTTAAGCCCTCCGGGACCCTTTCCCTCACGTGTGCAGTCTCAGG
TGGGTCAATTAGTTCTTCCAATTGGTGTGGCCAACCACCTGGTAAGGTCTCGAGTGGATAGGGGAAATTATCATA
GTGGCTCCACCAATTATAACCCCTCACTCAAGTCCAAGGTTACGATATCTGTGGACAAAGTAAAACCAATTCTCCCTCAAACTT
AGTAGTGTAACAGCGCAGAGACACCGCGGTGTACTGCGACAGGCGAACTGGAGCCTTTGACATTTGGGGACAGGG
AACTATGGTGACTGTGTCATCC (SEQ ID NO: 14)

FIG. 11B

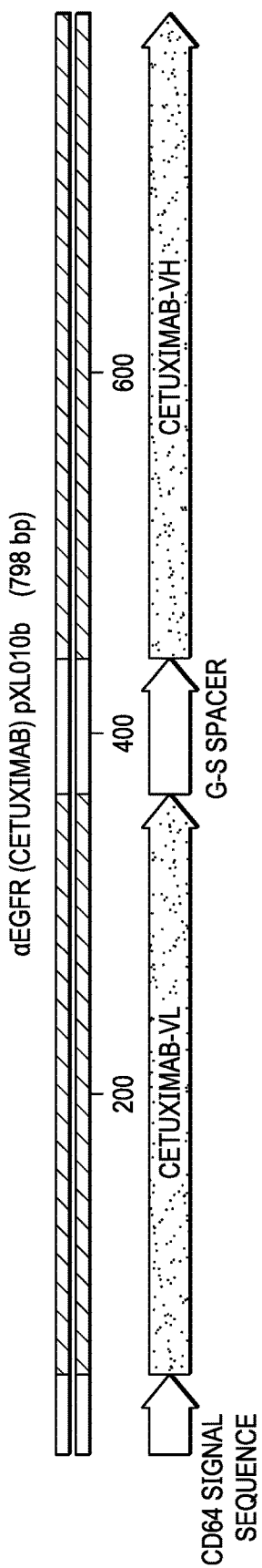

FIG. 12A

>αEGFR (CETUXIMAB) pXL010b.dna (798 bp)
LEADER CONSTRUCT:
ATGTGGTTCTTCTTACTACACATTGCTGTTGTGGGTTCCCGGTGGACGGT (SEQ ID NO.: 1)

VARIABLE REGION:
GATATTCTTCTTACTCAATCTCCCGTTATTTTGTCAGTATCCCCAGGTGAGCGAGTCAGCTTCTCTTGTCGAGGTCACAATCCAT
TGGCACCAACATACAATTGGTACCACAACAGCGCACCAACAGGGTCTCCCCGGCTCTTGATTAAGTACGCATCAGAAACATCCAT
TACCCAGTAGGTTCTCAGGGAGCGGGAGTGGCACTGACTTTACCCTGTCCATAAACACAGGCGTTGAGTCTGAGGACATCGGGACTAC
TATTGTCAGCAGAACAATTGGCCGACCACG TTTGGTGCGGAACAAAACTTGAACTCAAA (SEQ ID NO.: 15)

LINKER:
TCCTCAGGGGGCGGCGGGGGAAGTGGTGGGGGCGGCCAGGGGCCGGGGGCTCAGGAGGAGGGCGGATCAGGGCGGATCA (SEQ ID NO.: 3)

VARIABLE REGION:
CAGGTGCAGCTGCAGTCAGGGCCAAGCAGTCAGGACCTGGCCTCGTTCAGCCAAGCCAATCACTGAGTAGTAACGTGCACGGTGAGCGGCTTTAGCCT
GACAAGACTATGGTGTGTCCACTGGTCCGCCAATCCTTGGAGTCTCCTGGAAAAAGGCTTGGTGTTATCTCGGTGTTAACTTCCGGTAACACAG
ACTACAACACGCCATTCACCAGTCGCCTTAGTATTAACAAGGACAACAACTCCAAGTCTCCAGGTTTTCTTTAAAATGAACTCTCTGCAG
TCTAATGATACGGCAGCGGAATTTACTACTGTGCGGAGGGGACTCACGTACTATGACTAGTTCGCGTATTGGGGCCAAGGGACTCTCGT
TACTGTCTCAGCG (SEQ ID NO.: 16)

FIG. 12B

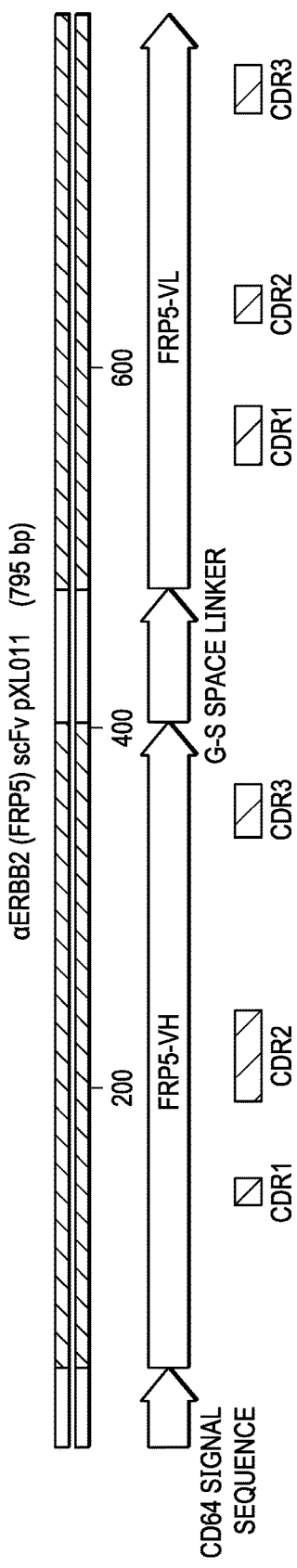

FIG. 14A

>αERBB2 (FRP5) scFv pXL011.dna (795 bp)
LEADER SEQUENCE:
ATGTGGTTTCTTACTACATTGCTGTTGTGGGTCCCGGT (SEQ ID NO.: 1)

HEAVY CHAIN:
GGACGGTCAGGTACAACTGCAGCAGTCTGGACCTGAACTGAAGAAGCCTGGAGAGACAGTCAAGATCTCCTGCAAGGCCTCTGGGT
ATCCTTTCACAAACTATGGAATGAACTGGGTGAAGCAGGCTCCAGGAAGGGTTTAAAGTGGATGGGCTGGATTAACACCTCCACT
GGAGAGTCAACATTTGCTGATGACATTCAAGGGACGGTTTGACTTCTCTTTGACTCTCTTTGACAAACCTCTGCCAACACTGCTATTTGCAGATCAA
CAACCTCAAAAGTGAAGACATGGCTACATATTTCTGTGCAAGATGGAGGTTTACCACGGCTACGTTCCTTACTGGGGCCAAGGGA
CCACGGTCACCGTTTCCTCT (SEQ ID NO.: 17)

LINKER:
TCCTCAGGGGGCGGGGAAGTGTGGGGCGGCAGCGGCGAGGGGCTCAGGAGGAGGCGGATCAGGCGGATCA (SEQ ID NO.: 18)

LIGHT CHAIN:
GACATCCAGCTGACCCAGTCTCCACAAATTCCTGTCCACTTCAGTAGGAGACAGGGTCAGCATCACCTGCAAGGCCAGTCAGGATGT
GTATAATGCTGTTGCCTGGTACCAGCAGAAACCAGGACAATCTCCTAAACTTCTGATTTACTCGGCATCTCCCGGTACACTGGAG
TCCCTTCTCGCTTCACTGGCTCTGGCCATCAGCAGTGTGCAGGCTGAAGACCTGGCAGGACCTGGCAGTTAT
TTCTGTCAGCAACATTTCGTACTCCATTCACGTTCGGCTCGGGGACAAAATTGGAGATC (SEQ ID NO: 18)

FIG. 14B

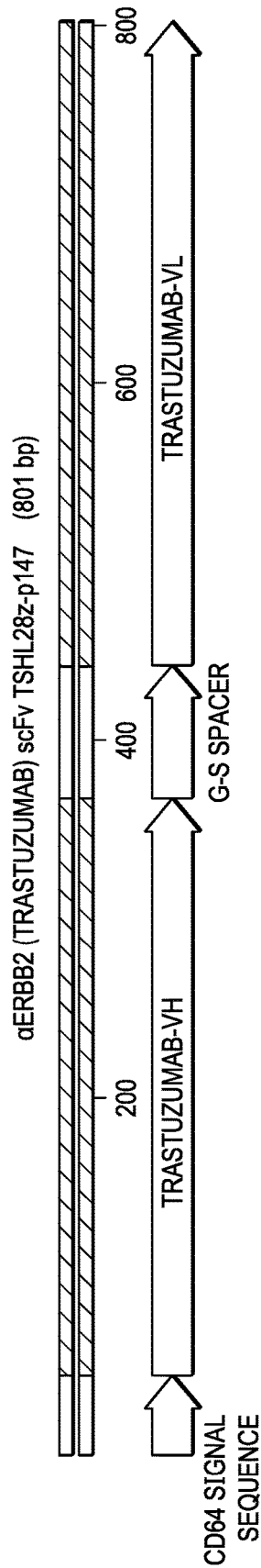

FIG. 15A

>αERBB2 (TRASTUZUMAB) scFv TSHL28z-p147.dna (801 bp)

LEADER SEQUENCE:
ATGTGGTTTCTTACTACACATTGCTGTTGTGGGTCCCGGT (SEQ ID NO.: 1)

HEAVY CHAIN:
GGACGGTGACATCCAGATGACCCAGAGCCCCAGCAGCCTGAGCGCCAGCGTGGGCGACAGAGTGACCATCACCTGCAGAGCCAGCC
AGGACGTGAACACCGCGGTGGCCTGGTATCAGCAGAAGCCCGGCAAGGCCCCCAAGCTGCTGATCTACAGCGCCAGCTTCCTGTAC
AGCGGGCGTGCCCAGCAGATTCAGCGGCAGCAGAAGGGCACCGACTTCACCCTGACCATCAGCAGCCTGCAGCCCGAGGACTTCGC
CACCTACTACTGCCAGCAGCACTACACCACCCCCCCACCTTCGGCCAGGGCACCAAGGTGGAGATCAAG (SEQ ID NO.: 19)

LINKER:
TCCTCAGGGGGCGGGGGAAGTGGTGGGGGCGGCAGCGGCGGCTCAGGGAGGAGGAGGCGGATCAGGCGGATCA (SEQ ID NO.: 3)

LIGHT CHAIN:
GAGGTGCAGCTGGTGGAGAGCGGCGGCGGCCTGGTGCAGCCCGGCGGCAGCCTGAGACTGAGCTGCGCCGCCAGCGGCTTCAACAT
CAAGGACACCTACATCCACTGGGTGAGACAGGCCCCGGCAAGGGCCTGGAGTGGGTGGCCAGAATCTACCCCACCAACGGCTACA
CCAGATACGCCGACAGCGTGAAGGGCAGATTCACCATCAGCGCCGACACCAGCAAGAACACCGCCTACCTGCAGATGAACAGCCTG
AGAGCCGAGGACACCGCCGTGTACTACTGCAGCAGATGGGGCGGCGACGGCTTCTACGCCATGGACTACTGGGGCCAGGGCACCCT
GGTGACCGTGAGCGCAGC (SEQ ID NO.: 20)

FIG. 15B

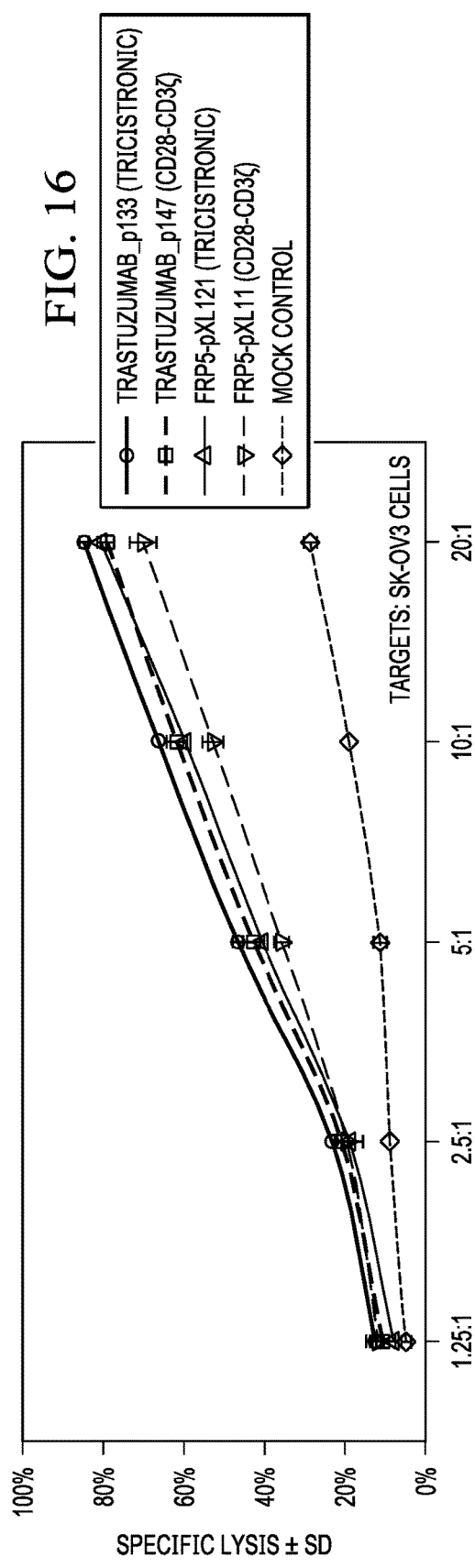
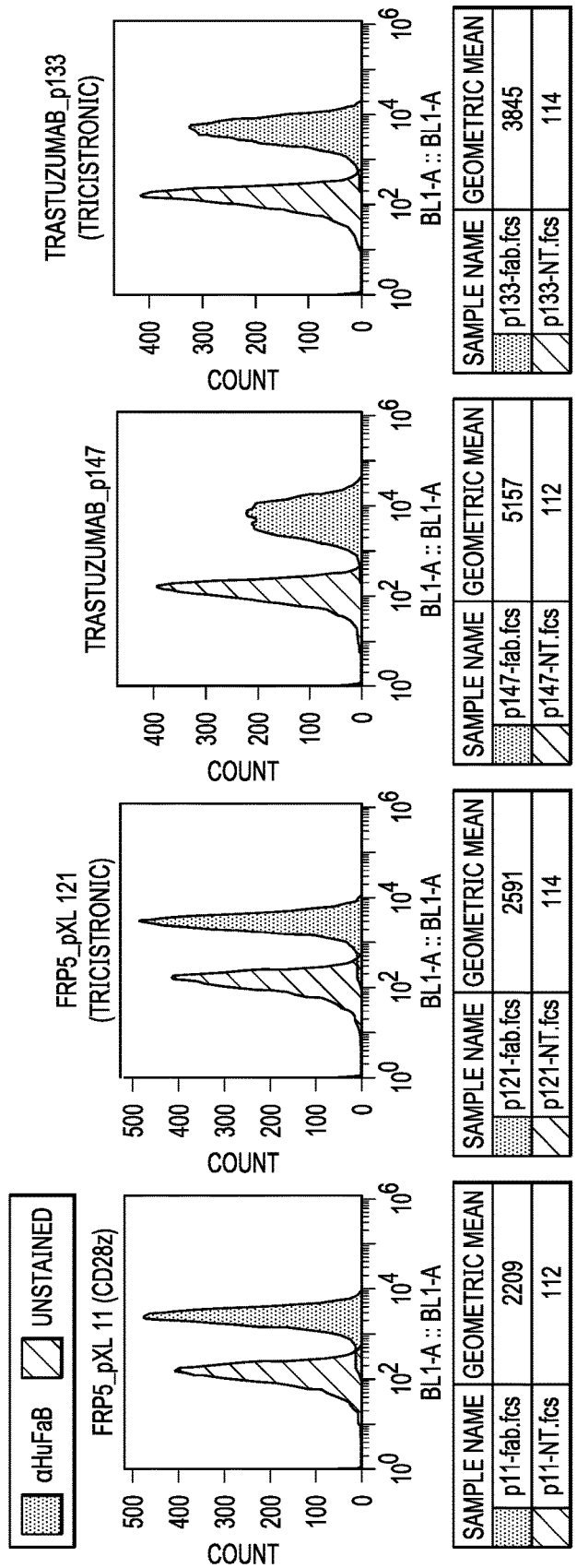
FIG. 16

SEQ ID NO.5: CAR-CD19-CD28/CD3ζ (CAR-19sih28ζ); Tail-end activation module.
ATTGAAGTTATGTATCCTCCTCCTTACCTAGACAATGAAGAGACAATGGAACCATTATCCATGTGAAAGGGAAACACCTTTGT
CCAAGTCCCCTATTTCCCGGACCTTCTAAGCCCTTTATTTTCTGGGTGCTGGTTGGTGGTGCTGCTTGCTATAGCTTGCTA
GTAACAGTGGCCTTTATTATTTTCTGGGTGAGGAGTAAGAGAGCCAGGCTCCTGCACAGTGACTACTACATGAACATGACTCCCCGC
CGCCCCGGGCCCCACCCAGCAAGCATTACCAGCCCCTATGCCCCACGCGACTTCGGACCTATCGCTCCAGAGTGAAGTTCAGC
AGGAGCGCAGACGCCCCGAGACGTACCAGCAGGGCCAGAACCAGTCTATAACGAGCTCAATCTAGGACGAAGAGAGGAGTACGAT
GTTTTGGACAAGAGACGTGGCCGGGACGATAAGATGGCGGAGGCCTACAGTGAAGCGAAGAACCCTCAGGAAGGCCTGTACAAT
GAACTGCAGAAAGATAAGATGGCGGAGGCCTACAGTGAGATTGGGATGAAAGGCGAGCGCCGGAGGGGCAAGGGCCACGATGGC
CTTTACCAGGGTCTCAGTACAGCCACGAAGGACACCTACGACGCCCTTCACATGCAGGCCCTGCCCCCTCGCTAA SEQ ID NO.21: Translated protein sequence
IEVMYPPPYLDNEKSNGTIIHVKGKHLCPSPLFPGPSKPFWVLVVVGGVLACYSLLVTVAFIIFWVRSKRSRLLHSDYMNMTPR
RPGPTRKHYQPYAPPRDFAAYRSRVKFSRSADAPAYQQGQNQLYNELNLGRREEYDVLDKRRGRDPEMGGKPQRRKNPQEGLYN
ELQKDKMAEAYSEIGMKGERRRGKGHDGLYQGLSTATKDTYDALHMQALPPR*

FIG. 17

SEQ ID NO.22: CD3ζ(HG) HUMAN CODON OPTIMIZED (DNA). TAIL-END ACTIVATION MODULE.

CAGCTGCCCATCACCGAGGCTCAATCCTTTGGGCTGCTTGATCCTAAGTTGTGTTATCTTCTTGACGGCATCCTGTTTAT
ATACGGTGTCATTTTGACAGCTCTCTTTCTCCGAGTTCAGTCGGTTCAAGTTCAGTCGGTCTCGCAGATGCTCCAGCAAGGCC
AAAATCAGCTGTATAACGAGTTGAAACCTTGGGCGACGAGAAGAATACGACGTGCTTGACAAACGCAGAGTCGGGACCCT
GAAATGGGGGGTAAGCCGCAAAGGCGAAGAATCCACAAGAGAGGTCTGTATAATGAATTGCAAAAAGACAAGATGGCTGA
GGCATACTCAGAGAGATTGGAATGAAAGGGGAAAGACGGAAAGGGCCACGATGGACTGTACCAAGGGCTGAGCACCG
CAACTAAAGATACATATGATGCTCTGCACATGCAGGCCCTGCCACCTAGATAA

SEQ ID NO.23: TRANSLATED PROTEIN SEQUENCE

QLPITEAQSFGLLDPKLCYLLDGILFIYGVILTALFLRVKFSRSADAPAYQQGQNQLYNELNLGRREEYDVLDKRRGRDP
EMGGKPQRRKNPQEGLYNELQKDKMAEAYSEIGMKGERRRGKGHDGLYQGLSTATKDTYDALHMQALPPR*

FIG. 18C scFv-CD3ζ CODON OPTIMIZED SCAFFOLD:

CAGCTGCCCATCACCGAGGCTCAATCCTTTGGGCTGCTTGATCCTAAGTTGTGTTATCTTCTTGACGGCATCCTGTTT
ATATACGGTGCATTTGACAGCTCTCTTCTCCGAGTCAAGTTCAGTCGGTCTGCAGATGCTCCAGTACCAGCAA
GGCCAAAATCAGCTGTATAACGAGTTGAACCTTGGGCGACGAGAAGAATACGACGTGCTTGACAAACGCAGAGGTCGG
GACCCTGAAATGGGGGTAAGCCGCAAAGGCGAAAGGCGAAAGGGGAAAGGGGAAAGACGGAGAGGAAAGGGGAAAGACGGAGAGGAAAGGGGAAAGACAAAG
ATGGCTGAGGCATACTCAGAGATTGGAATGAAAGGGCCACGATGGACTGTACCAAGGG
CTGAGCACCGCAACTAAAGATACATATGATGCTCTGCACATGCCAGGCCCCTGCCACCTAGATAA (SEQ ID NO.: 22)

ECTODOMAIN:

CAGCTGCCCATCACCGAGGCTCAATCCTTTGGGCTGCTTGATCCTAAG (SEQ ID NO.: 24)

TRANSMEMBRANE DOMAIN:

TTGTGTTATCTTCTTGACGGCATCCTGTTTATATACGGTGTCATTTTGACAGCTCTCTTTCTCC (SEQ ID NO.: 25)

CYTOPLASMIC DOMAIN:

GAGTCAAGTTCAGTCGGTCTGCAGATGCTCCAGCATACCAGCAAGGCCAAAATCAGCTGTATAACGAGTTGAACCTTG
GGCGACGAGAAGAATACGACGTGCTTGACAAACGCAGAGGTCGGGACCCTGAAATGGGGGTAAGCCGCAAAGGCGGA
AGAATCCACAGAGAGGGTCTGTATAATGAATTGCAAAAGACAAGATGGCTGAGGCATACTCAGAGATTGGAATGAAAG
GGGAAAGACGGAGGGGAAAGGCCACGATGGACTGTACCAAGGGCTGAGCACCGCAACTAAAGATACATATGATGCTC
TGCACATGCCAGGCCCCTGCCACCTAGATAA (SEQ ID NO.: 26)

FIG. 18D scFv-CD28/CD3ζ (CODON OPTIMIZED) SCAFFOLD:

ATTGAAGTTATGTATCCTCCTCCTTACCTAGACAATGAGAAGAGCAATGGAACCATTATCCATGTGAAAGGGAAACACCTTTGTC
CAAGTCCCCTATTTCCCGGACCTTCTAAGCCCTTTATTTTCTGGGTGAGGAGTAAGAGGAGCAGGCTCCTGCACAGTGACTACTACAGCCTATGCTGCTAGT
AACAGTGGCCTTTATTATTTCTGGGTGAGGAGTAAGAGGAGCAGGCTCCTGCACAGTGACTACTACAGCCTATGCTGCCGGC
CCGGGCCCCACCCGCAAGCATTACCAGCAGCCCCGCGTACCAGCAGGGCCAGAACCAGCTCTATAACGAGCTCAATCTAGGAGCAAGAGGCAAGGGGTACCAGGA
GCGCAGAACGCCCCCGCGTACCAGCAGCCCCGCGTACCAGCAGGGCCAGAACCAGCTCTATAACGAGCTCAATCTAGGACGACAAGAGAGAGGCCTGTACAATGAACTG
GGACAAGAGACGTGGCCGGGACCCTGAGATGGGGGAAAGCCGCAGAGAAGGCGAGGCGCCGAGGGGCAAGGGGCACGATGGCCTTTACC
CAGAAAGATAAGATGCGAGGCCTACAGTGAGATTGGGATGAAAGGCGAGCCCTTCACATGCGACGCCCTTCACATGCGACGCCCTGCCCCCTCGCTAA (SEQ ID NO.: 5)
AGGGTCTCAGTACAGCCACCAAGGACACCTACGACGCCCTTCACATGCGACGCCCTGCCCCCTCGCTAA (SEQ ID NO.: 5)

ECTODOMAIN:

ATTGAAGTTATGTATCCTCCTCCTTACCTAGACAATGAGAAGAGCAATGGAACCATTATCCATGTGAAAGGGAAACACCTTTGTC
CAAGTCCCCTATTTCCCGGACCTTCTAAGCCC (SEQ ID NO.: 27)

TRANSMEMBRANE DOMAIN:

TTTTGGGTGCTGGTGGTTGGTGGTGAGTCCTGCTATAGCTTGCTGCTAGTAACAGTGGCCTTTATTATTTTCTGG
(SEQ ID NO.: 28)

CYTOPLASMIC DOMAIN:

GTGAGGAGTAAGAGGAGCAGGCTCCTGCACAGTGACTACTACAGCCTATGCTGCCGGC
AGCCCTATGCCCCACCCGCAAGCATTACCAGCAGCCCCGCGTACCAGCA
GGGCCAGAACCAGCTCTATAACGAGCTCAATCTAGGACGACAAGAGAGAGGCCTGTACAATGAACTGCAGAAAGATAAGATGGCGGAGGCCT
GAGATGGGGGAAAGCCGCAGAGAAGGCGAGCCGCCGAGGGGCAAGGGGCACGATGGCCCTTTACCAGGGTCTCAGTACAGCCACCAAGGA
ACAGTGAGATTGGGATGAAAGGCGAGCCCTTCACATGCGACGCCCTGCCCCCTCGCTAA (SEQ ID NO.: 29)
CACCTACGACGCCCTTCACATGCGACGCCCTGCCCCCTCGCTAA (SEQ ID NO.: 29)

FIG. 18E

FIG. 20B (continued)
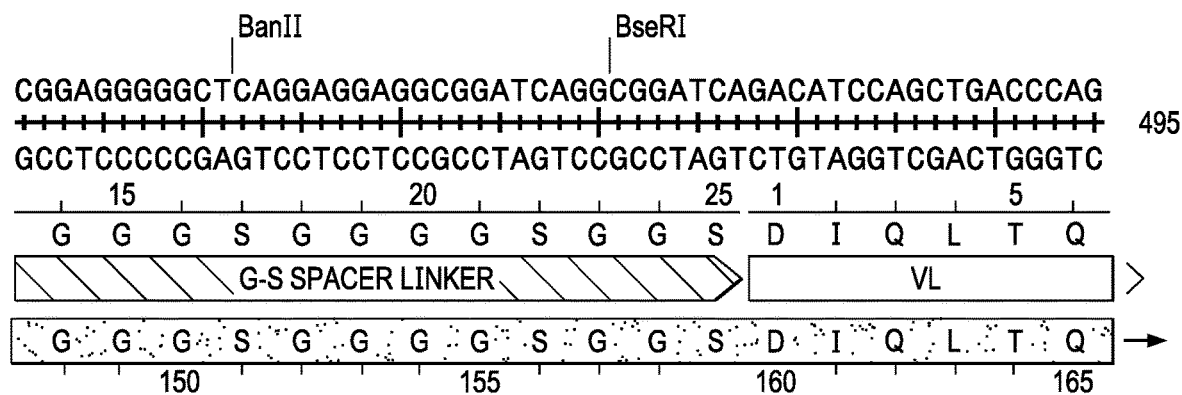
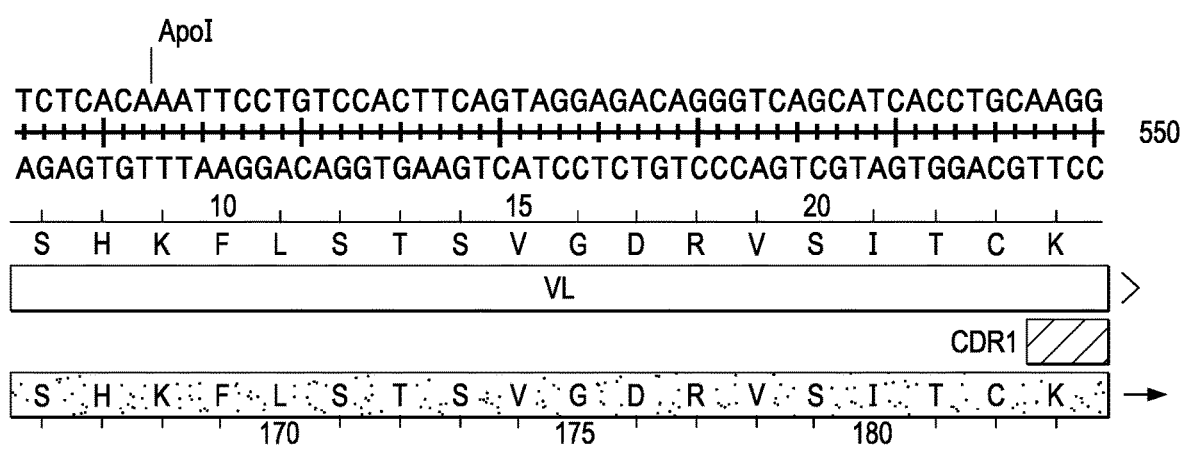
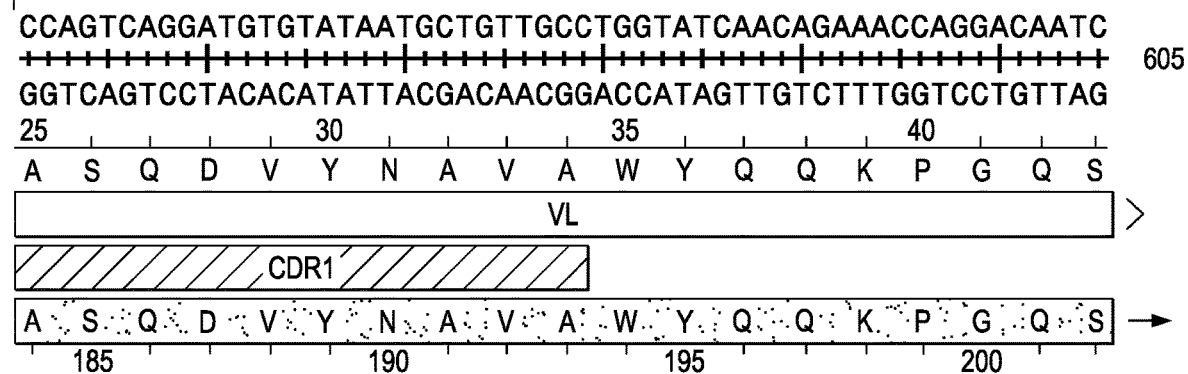

FIG. 20B (continued)

```
GGGCTGCTTGATCCTAAGTTGTGTTATCTTCTTGACGGCATCCTGTTTATATACG
++++|++++|++++|++++|++++|++++|++++|++++|++++|++++|++++|  880
CCCGACGAACTAGGATTCAACACAATAGAAGAACTGCCGTAGGACAAATATATGC
     25            30            35            40
  G    L    L    D    P    K    L    C    Y    L    L    D    G    I    L    F    I    Y
```
CD3ζ COMPLETE CO >
ECTODOMAIN / TRANSMEMBRANE DOMAIN
EXTRACELLULAR HINGE
G L L D P K L C Y L L D G I L F I Y →
280              285              290

```
GTGTCATTTTGACAGCTCTCTTTCTCCGAGTCAAGTTCAGTCGGTCTGCAGATGC
++++|++++|++++|++++|++++|++++|++++|++++|++++|++++|++++|  935
CACAGTAAAACTGTCGAGAGAAAGAGGCTCAGTTCAAGTCAGCCAGACGTCTACG
     45            50            55            60
  G    V    I    L    T    A    L    F    L    R    V    K    F    S    R    S    A    D    A
```
CD3ζ COMPLETE CO >
TRANSMEMBRANE DOMAIN / CYTOPLASMIC DOMAIN
ITAM1
G V I L T A L F L R V K F S R S A D A →
295        300        305        310

```
TCCAGCATACCAGCAAGGCCAAAATCAGCTGTATAACGAGTTGAACCTTGGGCGA
++++|++++|++++|++++|++++|++++|++++|++++|++++|++++|++++|  990
AGGTCGTATGGTCGTTCCGGTTTTAGTCGACATATTGCTCAACTTGGAACCCGCT
     65            70            75
  P    A    Y    Q    Q    G    Q    N    Q    L    Y    N    E    L    N    L    G    R
```
CD3ζ COMPLETE CO >
CYTOPLASMIC DOMAIN
ITAM1
P A Y Q Q G Q N Q L Y N E L N L G R →
315           320           325           330

FIG. 20B (continued)
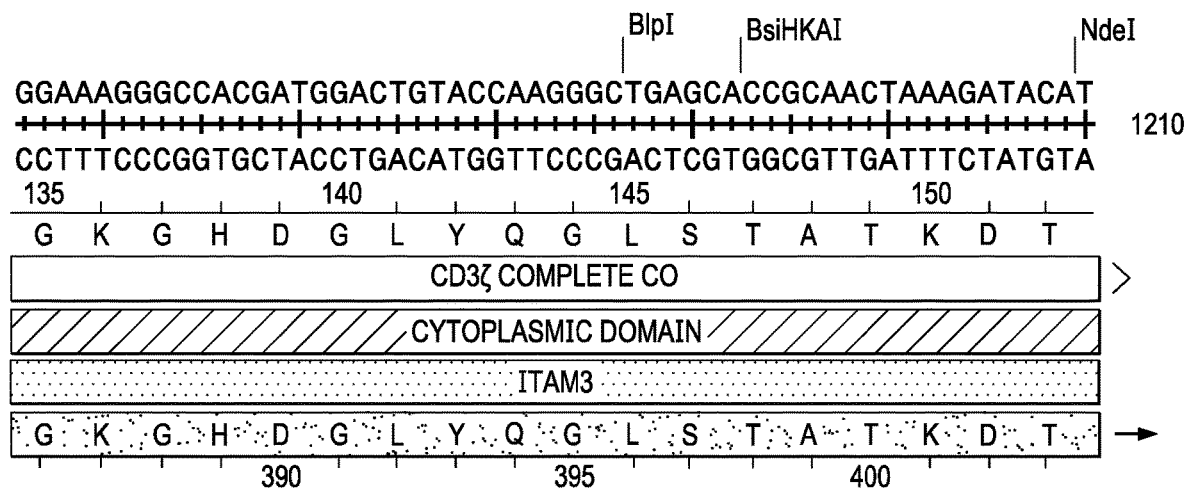
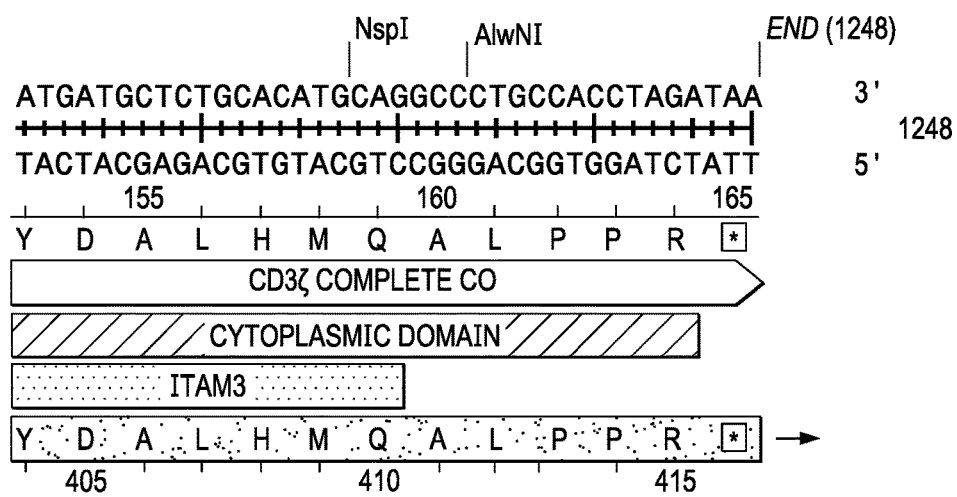

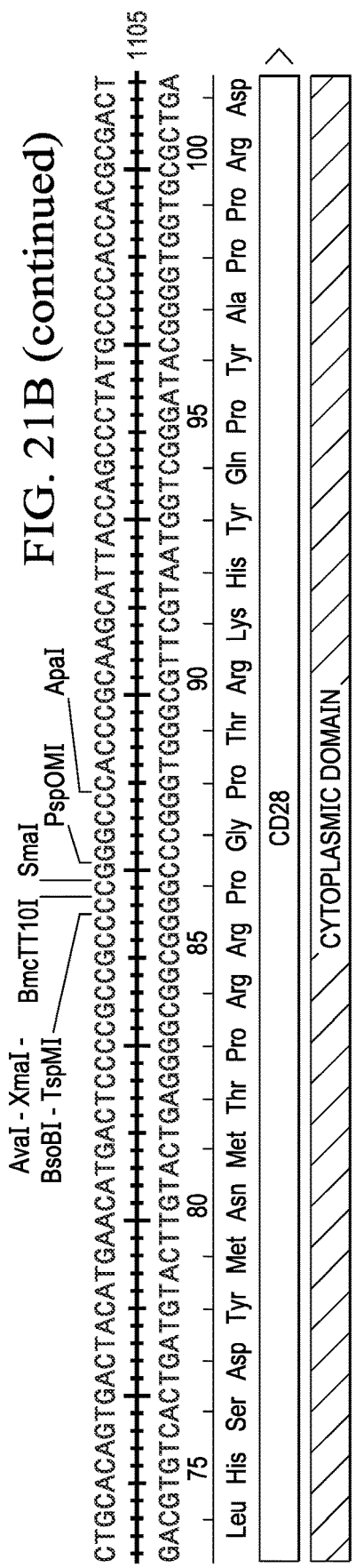
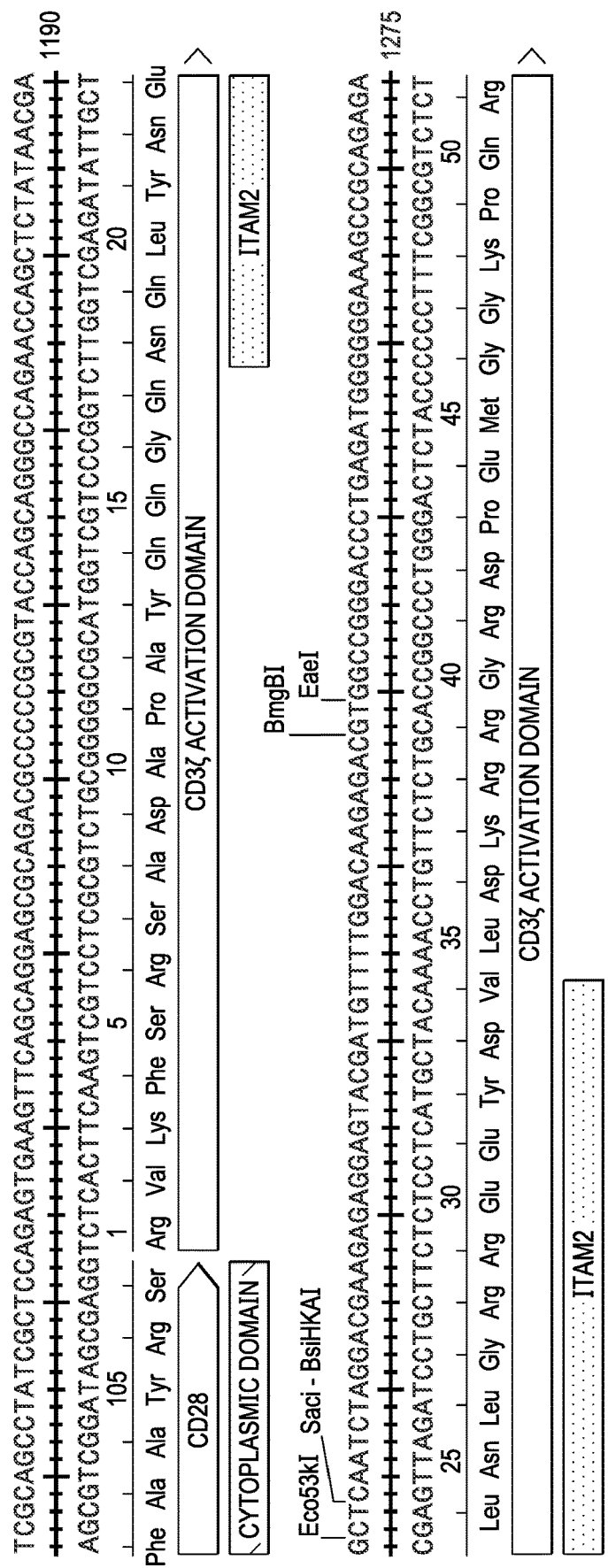
FIG. 21B (continued)

CD19-SPscFvFMC63 (1-801) (267 aa)

| FMC63-VL | G-S SPACER | FMC63-VH |

MWFLTTLLLWVPVDGDIQMTQTTSSLSASLGDRVTISCRASQDISKYLNWYQQKPDGTVKLLIYHTSRLHSGVPSRFSGSGSGTD

| CD64 SIGNAL SEQUENCE | | FMC63-VL |

YSLTISNLEQEDIATYFCQQGNTLPYTFGGGTKLEITSSGGGGSGGGGSGGGGSGGGGSEVKLQESGPGLVAPSQSLSVTCT

| FMC63-VL | G-S SPACER | FMC63-VH |

VSGVSLPDYGVSWIRQPPRKGLEWLGVIWGSETTYYNSALKSRLTIIKDNSKSQVFLKMNSLQTDDTAIYYCAKHYYYGGSYAMD

| FMC63-VH |

YWGGGTSVTVSS
    260   267

| FMC63-VH |

FIG. 24B
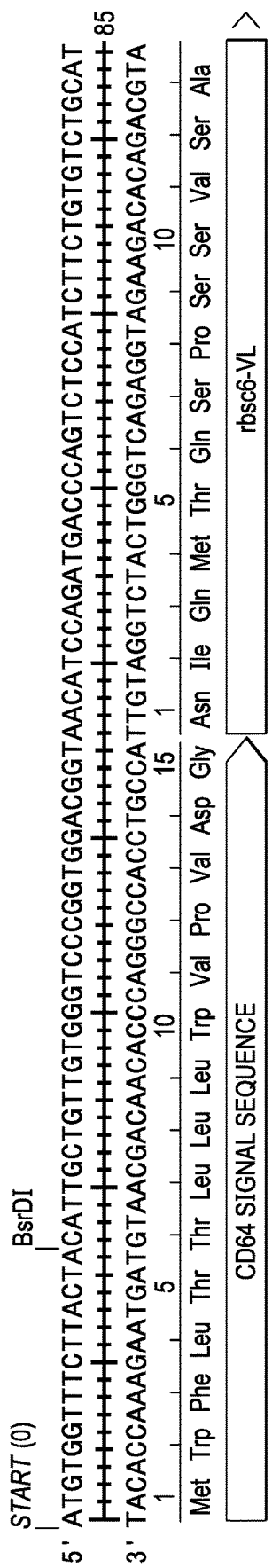
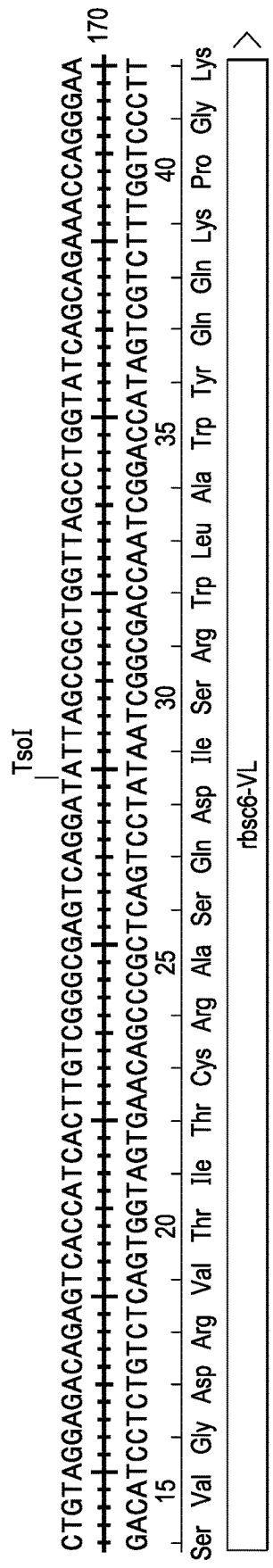
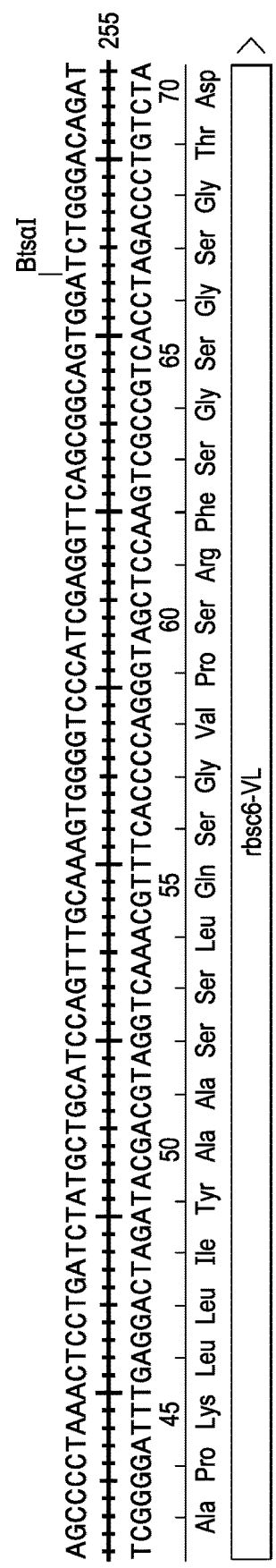

FIG. 24B (continued)

```
ACCTTCAGTAGCTATAGCATGAACTGGGTCCGGCCAGGCTCCAGGGAAGGGGCTGGAGTGGGTTTCATACATTAGTAGTAGTAGTA
              |                |                |                |                |
TGGAAGTCATCGATATCGTATCTTGACCCAGGCGGTCCGAGGTCCCTTCCCCGACCTCACCCAAAGTATGTAATCATCATCATCAT
  Thr Phe Ser Tyr Ser Ser Met Asn Trp Val Arg Gln Ala Pro Gly Lys Gly Leu Glu Trp Val Ser Tyr Ile Ser Ser Ser Ser
              30              35              40              45              50              55
                                                          rbsc6-VH GTACCATACAGTACGCAGACTCTGTGAAGGGCCGATTCACCATCTCCAGAGACAATGCCAAGAACTCACTGTATCTGCAAATGAA
              |                |                |                |                |
CATGGTATGTCATGCGTCTGAGACACTTCCCGGCTAAGTGGTAGAGGTCTCTGTTACGGTTCTTGAGTGACATAGACGTTTACTT
  Ser Thr Ile Gln Tyr Ala Asp Ser Val Lys Gly Arg Phe Thr Ile Ser Arg Asp Asn Ala Lys Asn Ser Leu Tyr Leu Gln Met Asn
              60              65              70              75              80
                                                          rbsc6-VH
```

FIG. 25B
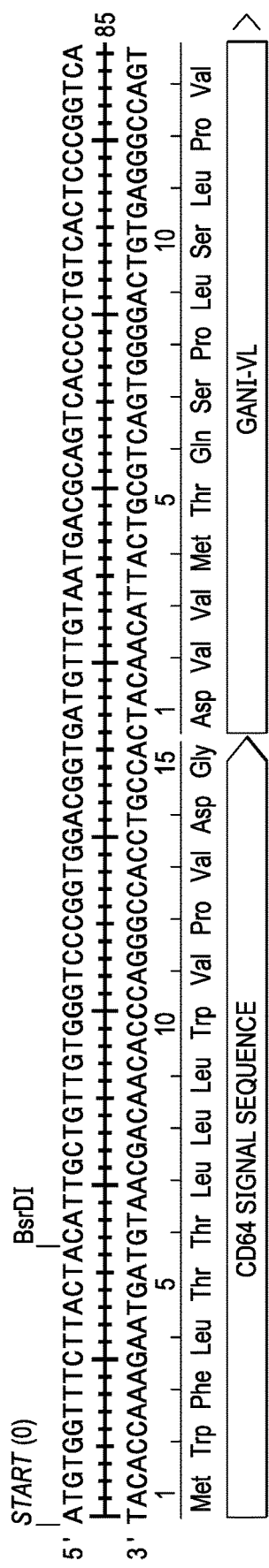
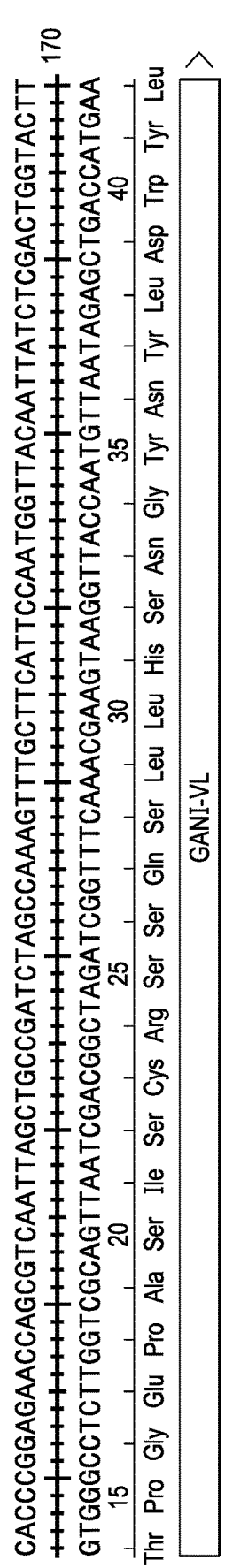
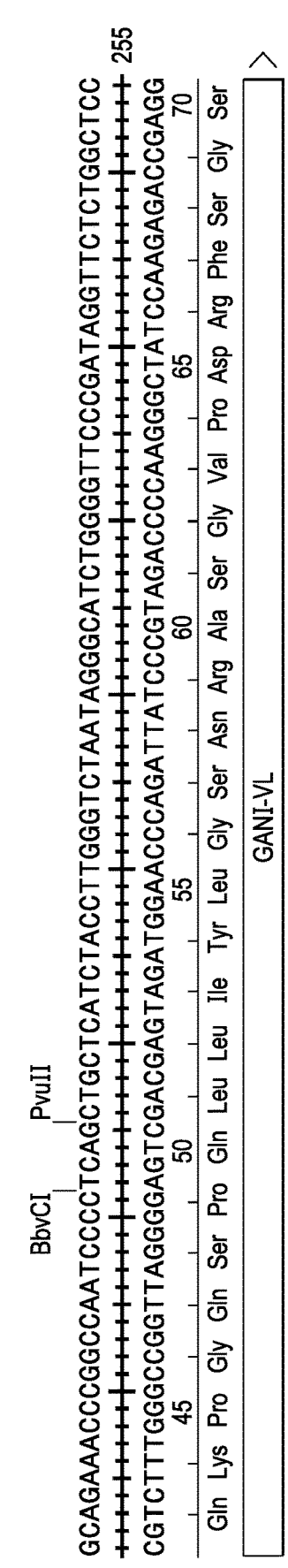

CHIMERIC T CELL RECEPTORS, NUCLEIC ACIDS, AND METHODS OF MAKING AND USING THE SAME

CROSS-REFERENCE TO RELATED PATENT APPLICATIONS

This patent application claims the benefit under 35 U.S.C. § 119(e) of U.S. Provisional Patent Application No. 63/059,560 filed on 31 Jul. 2020. The entire contents of U.S. 63/059,560 is incorporated by reference.

FIELD

The field of the invention relates to chimeric receptor genes that encode chimeric T cell receptors (TCRs), which provide antibody-type specificity to immune cells that are transformed with said genes, and methods of using the same, for the treatment of diseases such as cancer.

BACKGROUND

The background description includes information that may be useful in understanding the compositions and methods described herein. It is not an admission that any of the information provided herein is prior art or relevant to the compositions and methods, or that any publication specifically or implicitly referenced is prior art.

In recent years, immunotherapy has emerged as a therapeutic option for the treatment of cancer. A variety of monoclonal antibodies have been approved by regulatory agencies and are approved for use in the treatment of various types of cancers. Additional approaches are under investigation including cancer vaccines and adjuvants, chimeric antigen receptors (CAR) T-cell therapies, immune checkpoint inhibitors, and combinations thereof.

However, there is still a need to provide new compositions and methods that specifically target tumor cells for treatment, including solid and blood-based malignancies. Accordingly, there is still a need to provide improved compositions and methods of CAR T-cells with improved properties over their predecessors.

SUMMARY

The methods and techniques provided herein are directed to various systems and methods of developing and administering targeted immune therapy, as well as nucleic acids encoding the same.

In one aspect, a pharmaceutical composition comprising a CAR scaffold and an antigen binding domain in a single chimeric species is provided. In some aspects, the CAR scaffold may comprise a CD28 costimulatory signaling region and a CD3ζ activation domain. The CD28 costimulatory signaling region may comprise an ectodomain, a transmembrane domain, and a cytoplasmic domain. In some aspects, the cytoplasmic domain may include a CD28 co-activation domain. In other aspects, the CD3ζ activation domain may comprise at least two immunoreceptor tyrosine-based activation motifs (ITAMs). In some aspects, the CAR scaffold may be codon-optimized for improved expression in mammalian cell lines and/or for improved function upon transfection into natural killer (NK) or other types of immune cells. In further aspects, the antigen binding domain may comprise a VL and VH domain linked by a spacer. A CD64 leader sequence may be attached to the antigen binding domain, e.g., at the N-terminus of the antigen binding domain.

The compositions provided herein include chimeric TCRs and nucleic acids encoding chimeric TCRs. Methods of making and of administering the chimeric TCRs are also provided.

The compositions provided herein may be provided to any suitable cell, including NK cells, helper T cells, suppressor T cells, cytotoxic T cells, lymphokine-activated T cells, and any other immune cell capable of expressing a chimeric receptor. Suitable NK cells include but are not limited to high-affinity natural killer cells (haNKs), tumor activated natural killer cells (taNKs), and activated natural killer cells (aNKs).

In some aspects, the antigen binding domain may comprise an scFv, which includes a VL domain connected to a VH domain by a spacer. The scFv may include VH and VL domains from any suitable monoclonal antibody, including but not limited to a monoclonal antibody that has been approved by or is under investigation by a regulatory agency, e.g., cetuximab, ganitumab, etc.

In other aspects, the antigen binding domain and scaffold may be provided without a signaling domain, such that contact between the CAR scaffold expressing NK cell and the antigen expressing cell stimulates lysis of the antigen expressing cell.

In other aspects, the antigen binding domain may comprise an antibody fragment, including but not limited to a scFv, a di-scFv, a Fab, a Fab', a F(ab')2, a sdAb, or complementary determining regions (CDRs). In still other aspects, the antigen binding domain may comprise an aptamer, an affimer, a peptide, a protein, a protein scaffold, a small molecule, etc.

In still other aspects, the antigen binding domain may comprise a protein binding domain, including but not limited to FK506-binding protein 5 (FKBP5). Any suitable binding protein, which binds to an antigen on the surface of a target cell, are suitable for use with the CAR scaffolds provided herein.

The antibody fragment may be human, humanized, synthetic, or chimeric.

In other aspects, the present subject matter may also include DNA vectors comprising the nucleic acids disclosed herein, and host cells for expressing the DNA vectors. Nucleotides encoding the antigen binding domain and CAR scaffold may be inserted into any suitable expression vector, examples of which are known in the art. Host cells may include but are not limited to, a mammalian cell, an insect cell, a eukaryotic cell, a prokaryotic cell, a yeast cell, an animal cell, or a human cell. The host cell may also include, but is not limited to, a CHO cell, a NSO cell, a SP2-O cell, or a J558 cell.

Further contemplated are methods of making and expressing constructs comprising the antigen binding domain and CAR scaffold. In some aspects, the method includes: (a) introducing into a host cell a DNA encoding an antigen binding domain coupled to a CAR scaffold; and (b) culturing the host cell in media under conditions sufficient to express the antigen binding domain and CAR scaffold.

According to present techniques, a method for treating cancer in a subject is contemplated. The method may comprise administering to said subject a therapeutically effective amount of a pharmaceutical composition comprising the antigen binding domain coupled to a CAR scaffold. As used herein, "therapeutically effective amount" refers to administration of a pharmaceutical composition according to a dosage amount and/or a dosage regimen sufficient to treat a specific disease. One of ordinary skill in the art will appreciate that a therapeutically effective amount or dose may depend on a variety of factors, including the type of tumor or cancer, the route of administration of the therapeutic composition, the characteristics of the patient, the extent to which the tumor or cancer has metastasized, and/or the overall health of the patient. Effective doses may also be extrapolated from dose-response curves derived from in vitro or animal model test systems.

In some embodiments, the cancer is selected from but not limited to the group consisting of brain, breast, cervical, colon, gastric, lung, beta-cell lymphoma, melanoma, multiple myeloma, mesothelioma, ovarian, prostate, pancreatic, renal, thyroid, urothelial/bladder carcinoma, and hematological malignancies, e.g., acute myelogenous leukemia (AML), chronic lymphocytic leukemia (CLL), and Hodgkin's lymphoma. The techniques presented herein are applicable to any type of tumor, including but not limited to, primary tumors, secondary tumors, recurrent tumors, and derivative tumors.

In some aspects, administration occurs once, twice, or three times per week. As used herein, "administration" refers to the administration of the pharmaceutical composition to a patient in need thereof. In other aspects, the pharmaceutical composition may be administered by any suitable route, including but not limited to, bronchial, enteral, interdermal, intra-arterial, intradermal, intragastric, intramedullary, intramuscular, intranasal, intrathecal, intravenous, intraventricular, mucosal, nasal, oral, rectal, subcutaneous, sublingual, topical, tracheal, transdermal, vaginal, and vitrael.

Various uses of the aforementioned compositions are also contemplated herein. Various embodiments of the aforementioned compositions may also be administered to a patient in need thereof. Various objects, features, aspects and advantages of the compositions will become more apparent from the following detailed description of preferred embodiments.

BRIEF DESCRIPTION OF THE DRAWINGS

FIG. 2A shows a CAR construct comprising a single chain antibody fragment coupled to an extracellular CD8 hinge region. The hinge region is connected to a CD28 transmembrane domain that is linked to an intracellular signaling domain, in this case, a FcεRIγ signaling domain (instead of a CD28-CD3ζ construct as shown in FIG. 1). This CAR construct has shown cytotoxicity/ADCC in comparative studies.

FIG. 2B shows an illustration of a tricistronic construct, which may be inserted into a vector, such as a pNEUKv1 vector. This construct comprises a nucleotide sequence encoding (in order) a CD19CAR domain, a P2A sequence, an optional linker, a CD16 (158V) domain, an IRES sequence, and an ERIL-2 domain. The tricistronic construct incorporates expression of a high affinity variant of the Fc receptor (CD16-158V) and allows growth activity in the absence of exogenous IL-2.

FIGS. 3A-3B show additional illustrations of a CD28-CD3ζ construct according to aspects provided herein. FIG. 3A shows a detailed functional organization of an antigen binding domain coupled to a CD28-CD3ζ scaffold. The antigen binding domain comprises a FMC63-$V_L$ domain—a GS spacer—a FMC63-$V_H$ domain (also referred to as 19slh28ζ). The antigen binding domain and CAR scaffold may be inserted into any suitable vector, and may comprise about 1464 bp. In this figure, the locations of the CDRs (CDR1, CDR2, CDR3 for the heavy and light chains are shown).

FIG. 3B shows another illustration of the 19slh28ζ (p123) construct, which is similar to FIG. 1 and includes FMC63-VL and FMC63-VH domains, linked by a $SG_x$ spacer. The various domains of the CAR scaffold, including the CD28 and CD3ζ activation domains, are shown. Control vectors (not shown) may be used for functional comparison as described herein.

FIG. 4 shows nucleotide sequences for a human codon optimized DNA sequence (CAR19slh28ζ (αCD19-CD28/CD3ζ)). Nucleotide sequences encoding various domains are shown, including a nucleotide sequence that encodes a CD64 leader sequence (SEQ ID NO.: 1), nucleotide sequences that encode variable regions (SEQ ID NOs.: 2,4), a nucleotide sequence that encodes a G-S spacer (SEQ ID NO.: 3), and a nucleotide sequence that encodes ectodomain, transmembrane and signaling domains (SEQ ID NO.: 5). As shown previously, SEQ ID NOs.: 1-5 may be linked together to form a full length CAR construct that encodes the antigen binding domain.

SEQ ID NO.: 5 represents the CAR scaffold for FIGS. 4-17, unless indicated otherwise. Further, FIGS. 4-17 correspond to nucleotide sequences that have been codon optimized for expression in human cell lines, in some cases, resulting in an improvement in expression levels of the CAR scaffold construct up to 25% above a non-codon optimized construct. Thus, one or more of the nucleotide sequences encoding the VH, VL and/or CD28/CD3ζ domains may be codon optimized.

FIG. 5 shows another representation of the nucleotide sequence of FIG. 4 but limited to the sequences encoding the antigen binding domain. Various domains are shown, including a nucleotide sequence that encodes a CD64 leader sequence (SEQ ID NO.: 1), nucleotide sequences that encode variable regions (SEQ ID NOs.: 2, 4), and a nucleotide sequence that encodes a G-S spacer (SEQ ID NO.: 3). The sequences are linked together (leader—variable region—spacer—variable region) to form, upon expression, a scFv sequence. These sequences have been codon optimized for expression in human cells.

FIG. 6 shows an amino acid sequence (SEQ ID NO.: 6), corresponding to the nucleotide sequence of (FIG. 5) for a FMC63-derived binding domain in a scFv format. The first underlined portion is the CD64 leader sequence, followed by a variable region (FMC63-VL), a second underlined portion representing a G-S spacer, followed by a variable region (FMC63-VH).

Figure 1:
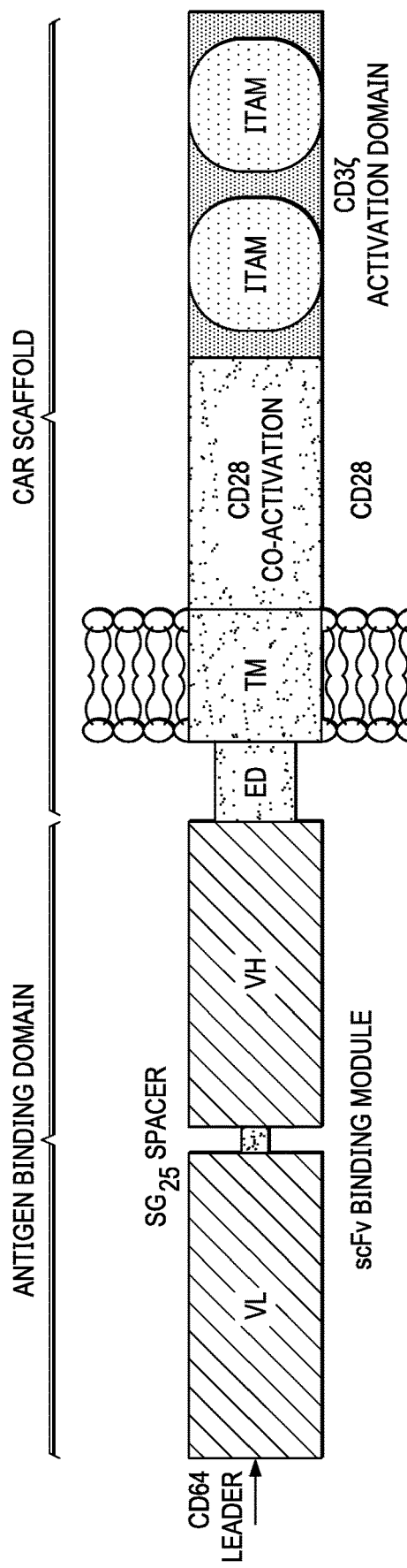
FIG. 1 is an illustration showing various domains of the antigen binding domain and CAR scaffold, according to examples provided herein. The antigen binding domain includes a CD64 leader sequence attached to the N-terminal of a scFv binding molecule, wherein the VL and VH domains are connected to each other via a spacer. The scFv domain is coupled to a CAR scaffold, comprising a CD28 domain and an activation domain. The CD28 domain comprises an extracellular domain, a transmembrane domain, a CD28 co-activation domain, and is coupled to a CD3ζ activation domain comprising at least two ITAM regions.
Figures 2A, 2B:
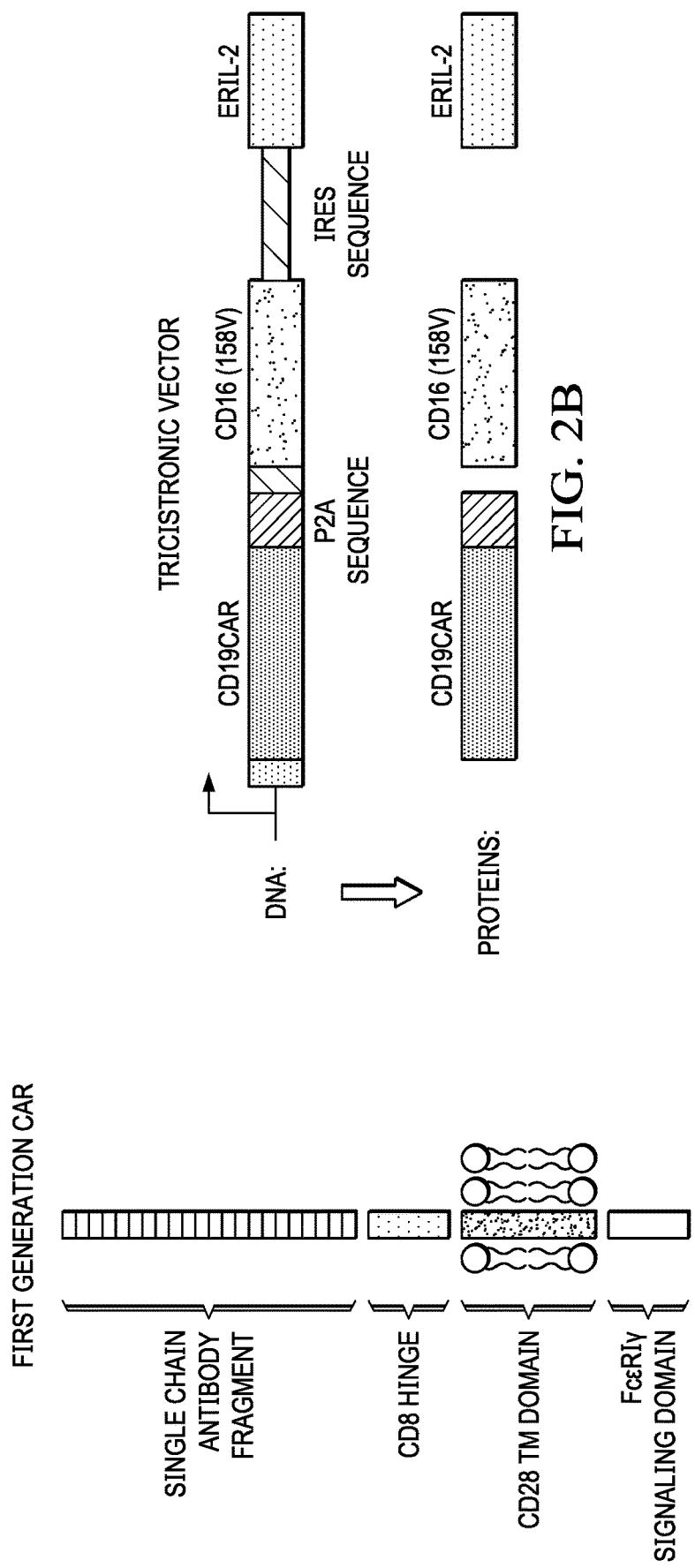
FIGS. 2A-2B are illustrations showing alternative configurations of CAR-T receptors, for comparison to the CAR scaffolds provided herein.

FIGS. 7A-7B show experimental data comparing specific cell lysis amounts of the constructs in FIGS. 1 and 2B. These constructs represent anti-CD19 CARs that bind to CD19, a B-lineage specific transmembrane glycoprotein expressed in more than 95% of B-cell malignancies. As this protein is a cell-surface protein, it is an ideal target for novel CAR based immunotherapies. These anti-CD19 CARs may target cytotoxic cells to the malignant cells.

FIG. 7A shows specific lysis percentages based on a ratio of effector to target cells in sup-B15 cells. Both the anti-CD19 scFv tricistronic construct and the anti-CD19 scFv CD28CD3ζ construct showed higher cell lysis percentages than the control. The tricistronic construct appeared to have somewhat higher cell lysis percentages than the CD28-CD3ζ construct. These differences may be attributed in part due to expression levels of the antigen binding domain, which may vary based on cell type. FIG. 7B shows specific lysis percentages based on a ratio of effector to target cells in Ramos cells. Both the anti-CD19 scFv tricistronic construct and the anti-CD19 scFv CD28-CD3ζ construct showed higher cell lysis percentages than the control. The tricistronic construct and the CD28-CD3ζ construct showed comparable (within 10%) lysis percentages.

FIG. 8A shows an illustration of an anti-αPD-L1 (SHIE2) scFv construct. Various domains are shown, including a CD64 leader domain, heavy and light chain variable regions, as well as a linker.

FIG. 8B shows the corresponding nucleotide sequences encoding the domains of FIG. 8A, including nucleotide sequences that encode a leader sequence (SEQ ID NO.: 1), anti-αPD-L1 light and heavy chains (SEQ ID NOs.: 7, 9), and a linker (SEQ ID NO.: 8). This nucleotide sequence (leader variable region linker variable region) has been codon optimized for expression in human cells.

FIG. 9A shows an illustration of an anti-αPD-L1 (RBSC6) scFv construct that is human codon optimized. Various domains are shown, including a CD64 leader sequence and heavy and light chain variable regions (RBSC6-VL and RBSC6-VH) connected by a linker/spacer. The variable regions are linked together to form a scFv sequence.

FIG. 9B shows nucleotide sequences encoding the anti-αPD-L1 (RBSC6) scFv construct of FIG. 9A, including nucleotide encoding a CD64 leader sequence (SEQ ID NO.: 1), a variable region (RBSC6-VL) (SEQ ID NO.: 10), a linker (SEQ ID NO.: 11), and another variable region (RBSC6-VH) (SEQ ID NO.: 12). This nucleotide sequence (leader—variable region—spacer—variable region) has been codon optimized for expression in human cells.

Figure 10:
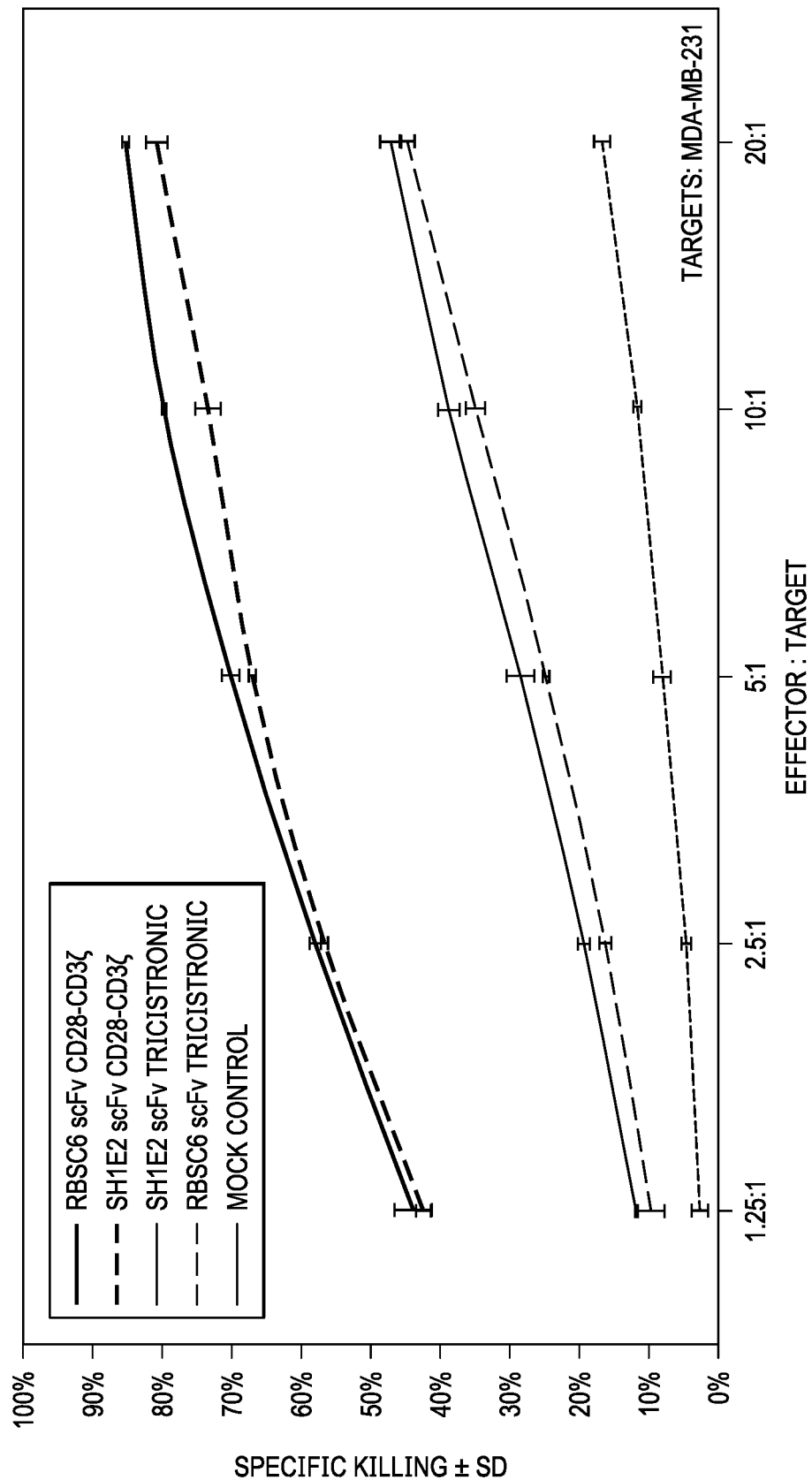

FIG. 10 shows experimental data comparing specific cell lysis percentages of the expressed constructs of FIGS. 8A-8B and 9A-9B. These constructs represent anti-PD-L1 CARs. PD-L1, a transmembrane glycoprotein, is expressed in different types of cancer cells and is an ideal target for CAR-based immunotherapies. Anti-PD-L1 antibodies target PD-L1 on the surface of cancer cells to trigger cell killing of the malignant cells. FIG. 10 shows specific lysis percentages of the anti-PD-L1 CARs based on a ratio of effector to target cells in MDA-MB-231cells. Both the RBSC6 scFv tricistronic construct and the SH1E2 scFv tricistronic construct showed higher cell lysis percentages than the control. Both the SH1E2 scFv CD28-CD3ζ construct and the RBSC6 scFv CD28-CD3ζ construct showed a higher cell lysis percentages than the tricistronic constructs.

FIG. 11A shows an illustration of an αIGF1R (ganitumab) scFv construct that is human codon optimized. Various domains are shown, including a CD64 leader sequence and heavy and light chain variable regions (Gani-VL and Gani-VH) connected by a G-S spacer. The variable regions are linked together via the spacer to form a scFv sequence.

FIG. 11B shows the corresponding nucleotide sequences of the domains of the construct of FIG. 11A. Nucleotide sequences encoding the leader sequence (SEQ ID NO.: 1), ganitumab light chain (SEQ ID NO.: 13), linker (SEQ ID NO.: 30), and ganitumab heavy chain (SEQ ID NO.: 14) are shown. This sequence (leader—variable region—spacer—variable region) has been codon optimized for expression in human cells.

FIG. 12A shows an illustration of an αEGFR (cetuximab) scFv construct. Various domains are shown, including a CD64 leader sequence and heavy and light chain variable regions connected by a G-S spacer that to form a scFv sequence.

FIG. 12B shows the corresponding nucleotide sequences of the domains of the αEGFR scFv construct of FIG. 12A. Nucleotide sequences encoding the leader (SEQ ID NO.: 1), anti-αEGFR light chain (SEQ ID NO.: 15), G-S spacer (SEQ ID NO.: 3), and anti-αEGFR heavy chain (SEQ ID NO.: 16) are shown. This sequence (leader—variable region—spacer—variable region) has been codon optimized for expression in human cells.

Figure 13A:
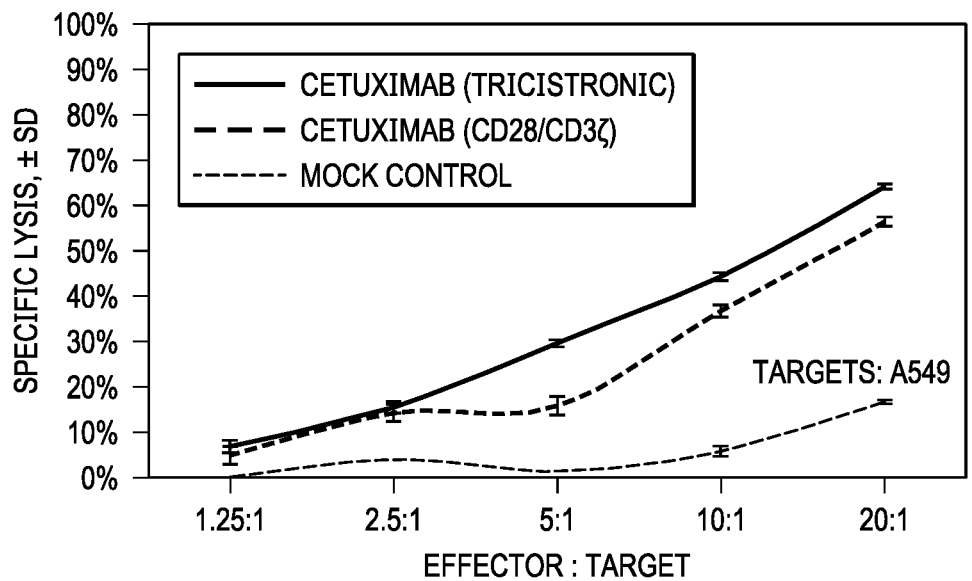
Figure 13B:
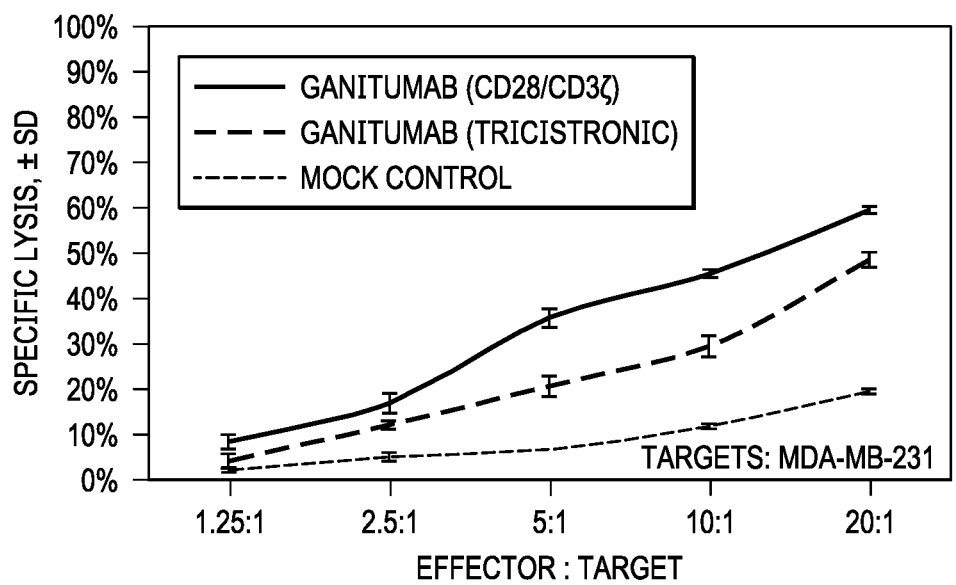

FIGS. 13A-13B show experimental data comparing specific cell lysis percentages of the constructs of FIGS. 11A-11B and 12A-12B. These constructs represent anti-IGFR-1 or anti-EGFR CARs. IGFR-1 and EGFR are transmembrane glycoproteins, expressed in different types of cancer cells, and are ideal targets for CAR-based immunotherapies. FIG. 13A shows specific lysis percentages based on a ratio of effector to target cells in A549 cells. Both the anti-EGFR scFv tricistronic construct and the anti-EGFR scFv CD28/CD3ζ construct showed higher cell lysis percentages than the control. The anti-EGFR scFv CD28-CD3ζ construct showed generally higher lysis percentages than the anti-EGFR tricistronic construct.

FIG. 13B shows specific lysis percentages based on a ratio of effector to target cells in MDA-MB-231 cells. Both the anti-IGFR-1 scFv CD28-CD3ζ construct and the anti-IGFR-1 scFv tricistronic construct showed higher cell lysis percentages than the control. The anti-IGFR-1 scFv CD28-CD3ζ construct showed somewhat higher lysis percentages than the anti-IGFR-1 scFv tricistronic construct.

FIG. 14A shows an illustration of a FRP5 scFv construct that is human codon optimized. Various domains are shown, including a CD64 leader sequence and heavy and light chain variable regions connected by a G-S spacer/linker. The variable regions are linked together to form a scFv sequence. The antigen binding domain may bind to HER2.

FIG. 14B shows the corresponding nucleotide sequences of the domains of the αERBB2 (FRP5) scFv construct of FIG. 14A. Nucleotide sequences encoding the leader (SEQ ID NO.: 1), (αFRP5-VH) FRP5 heavy chain (SEQ ID NO.: 17), linker (SEQ ID NO.: 3), and (αFRP5-VL) FRP5 light chain (SEQ ID NO.: 18) are shown. This sequence (leader variable region spacer variable region) has been optimized for expression in human cells.

FIG. 15A shows an illustration of a trastuzumab scFv construct that is human codon optimized. Various domains are shown, including a CD64 leader sequence and heavy and light chain variable regions connected by a G-S spacer to form a scFv sequence.

FIG. 15B shows the corresponding nucleotide sequences of the domains of the construct of FIG. 15A. Nucleotide sequences encoding the CD64 leader (SEQ ID NO.: 1), trastuzumab-VH (SEQ ID NO.: 19), G-S spacer (SEQ ID NO.: 3), and trastuzumab-VL (SEQ ID NO.: 20) are provided. This sequence (leader—variable region—spacer—variable region) has been optimized for expression in human cells.

FIG. 16 shows experimental data comparing specific cell lysis percentages of the constructs of FIGS. 14A-14B and 15A-15B. The FRP5 CARs and trastuzumab CARs both bind to HER2(αERBB2). FIG. 16 shows specific lysis percentages based on a ratio of effector to target cells in SK-OV3 cells. Both the αERBB2/FRP5 scFv tricistronic construct and the αERBB2/FRP5 scFv CD28-CD3ζ construct showed higher cell lysis percentages than the control.

FIG. 17 shows nucleotide sequences encoding a CAR scaffold (SEQ ID NO.: 5) comprising a CD28 co-stimulatory segment from CD28 and an activation domain of CD3ζ with the two final immunoreceptor tyrosine-based activation motif (ITAMs)). The antigen binding domain is followed by the CD28-derived hinge (ectodomain), transmembrane and coactivating cytoplasmic domains followed by a distal activating domain from CD3ζ. Nucleotide sequence (SEQ ID NO.: 5) may be translated to generate amino acid sequence (SEQ ID NO.: 21).

Figure 18A:
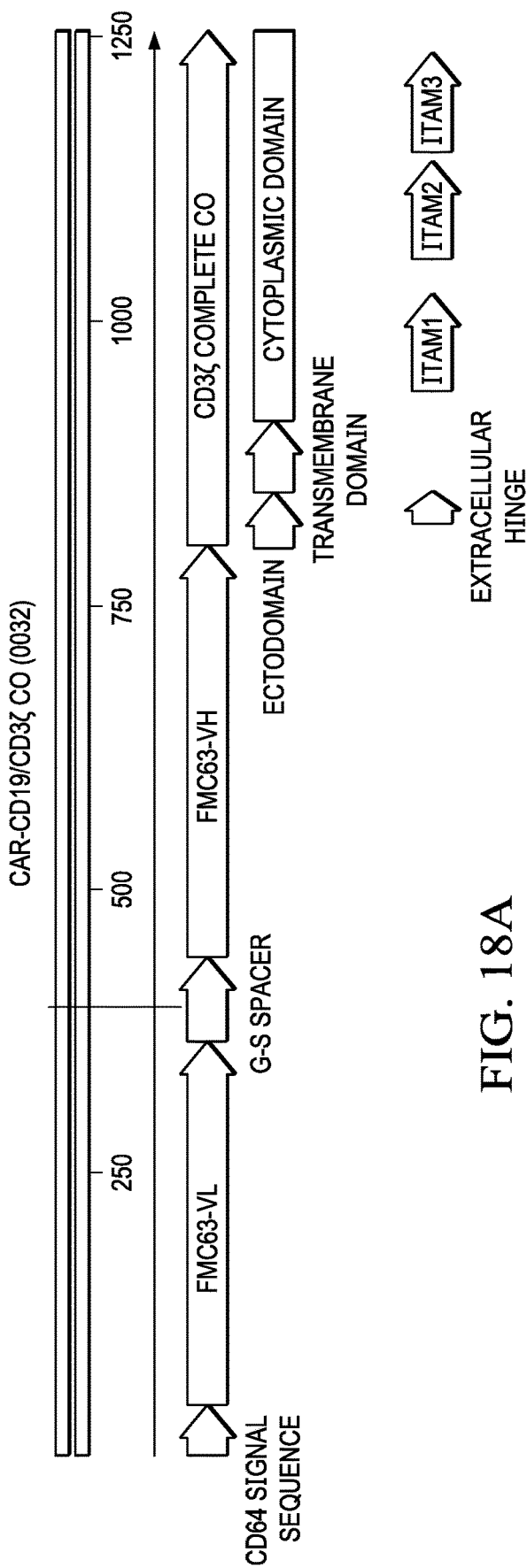
Figure 18B:
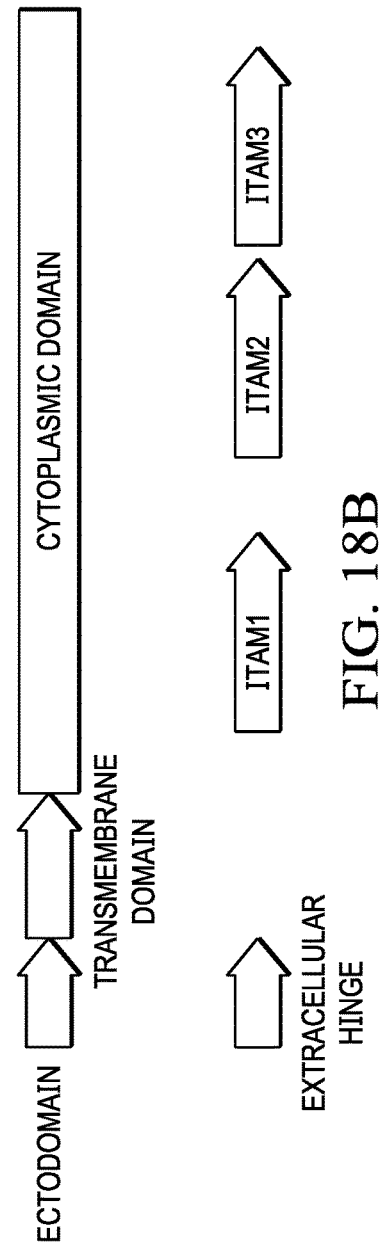

FIGS. 18A-18B show a schematic representation of another CAR construct containing a CD3ζCO activation domain. This construct contains the complete CD3ζ gene, including an ectodomain (hinge), a transmembrane domain, and a cytoplasmic domain (e.g., including 3×ITAMS). This construct has been codon optimized (CO).

FIG. 18C shows a nucleotide sequence that has been codon optimized for human expression, corresponding to the domains of FIGS. 18A-18B. Codon optimization improves expression (e.g., higher levels of the construct), which may result in improved efficacy (killing) once transfected into NK cells (e.g., taNKs)). Nucleotide sequence (SEQ ID NO.: 22) may be translated to generate amino acid sequence (SEQ ID NO.: 23).

FIGS. 18D and 18E show codon optimized nucleotides encoding the scFv-CD3ζ (SEQ ID NO.: 22) and scFv-CD28/CD3ζ (SEQ ID NO.: 5) scaffolds. FIG. 18D shows nucleotides encoding the ectodomain (SEQ ID NO.: 24), transmembrane domain (SEQ ID NO.: 25), and cytoplasmic domain (SEQ ID NO.: 26) for the scFv-CD3ζ domain (SEQ ID NO.: 22). FIG. 18E shows nucleotide sequences encoding the ectodomain (SEQ ID NO.: 27), transmembrane domain (SEQ ID NO.: 28), and cytoplasmic domain (SEQ ID NO.: 29) for the scFv-CD28/CD3ζ domain (SEQ ID NO.: 5).

Figure 19:
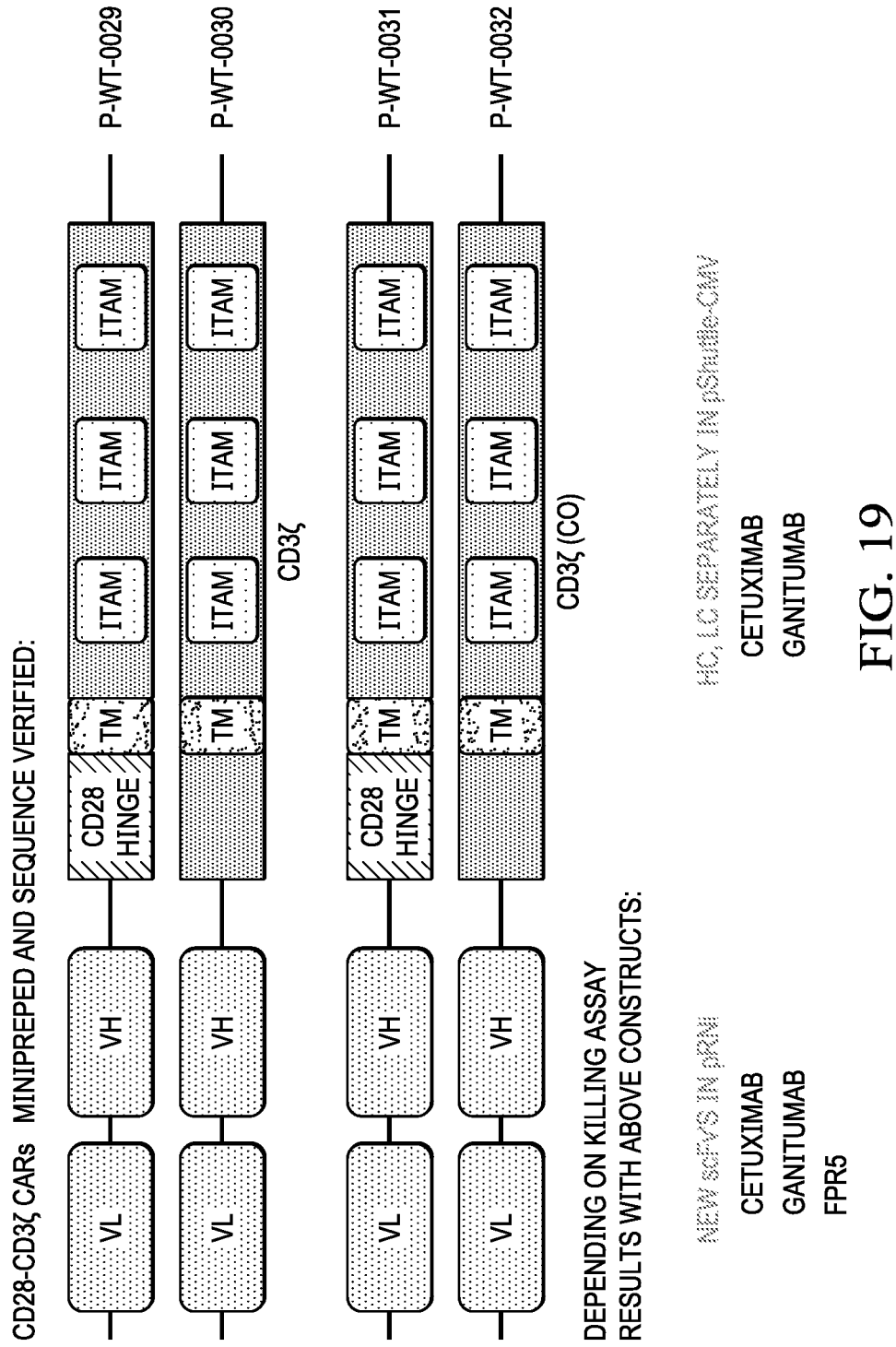

FIG. 19 shows multiple schematic representations of constructs according to the techniques provided herein. The activation domain comprises a transmembrane component and a CD3ζ with three ITAMs, and may be codon optimized (CO) (P-WT-0031 and P-WT-0032) or may not be codon optimized (P-WT-0029 and P-WT-0030). In some cases, a CD28 hinge domain may be present (P-WT-0029 and P-WT-0031). Heavy and light chain domains may be obtained from any suitable monoclonal antibody (e.g., cetuximab, ganitumab, etc.). Any suitable expression vector may be used, e.g., pRNi, pShuttle-CMV, etc. Constructs may include single vector constructs such as scFvs. Alternatively, constructs may include pShuttle-CMV vectors that allow for expression of HC and LC chains separately and formation of the antigen binding domain in vivo.

The P-WT-0029 and 0030 scaffolds include native T cell structures. P-WT-0031 corresponds to a scaffold comprising a CD28 hinge+CD3ζ, and P-WT-0032 corresponds to a full CD3ζ scaffold. Any of these scaffolds may be incorporated into NK cells.

Figure 20A:
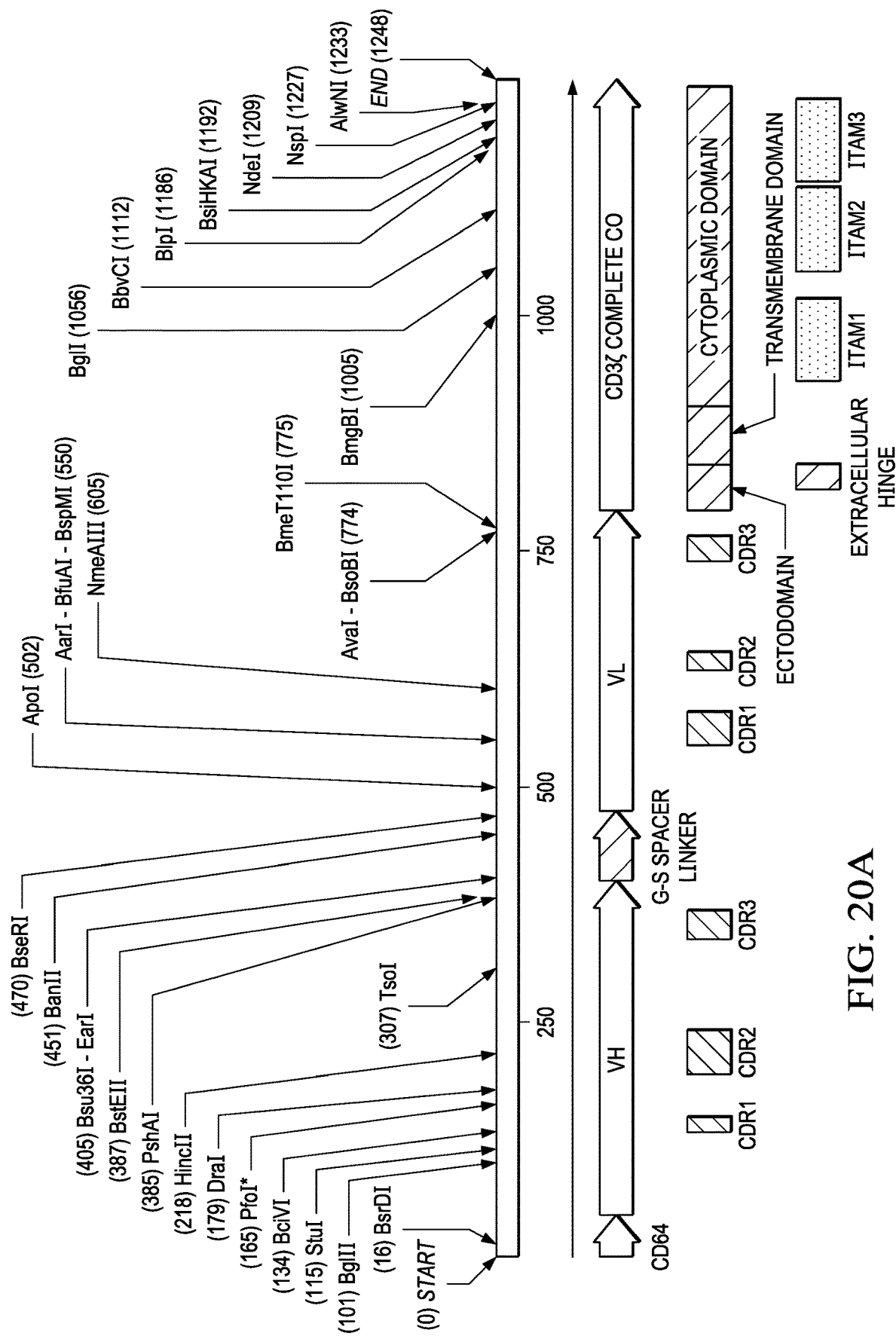

FIG. 20A shows a schematic illustration of the construction, orientation, and restriction sites a construct according to present techniques. Restriction sites are shown, along with relevant domains (CD64-VH domain-G-S spacer/linker-VL domain-CD3ζ complete CO).

Figure 20B:
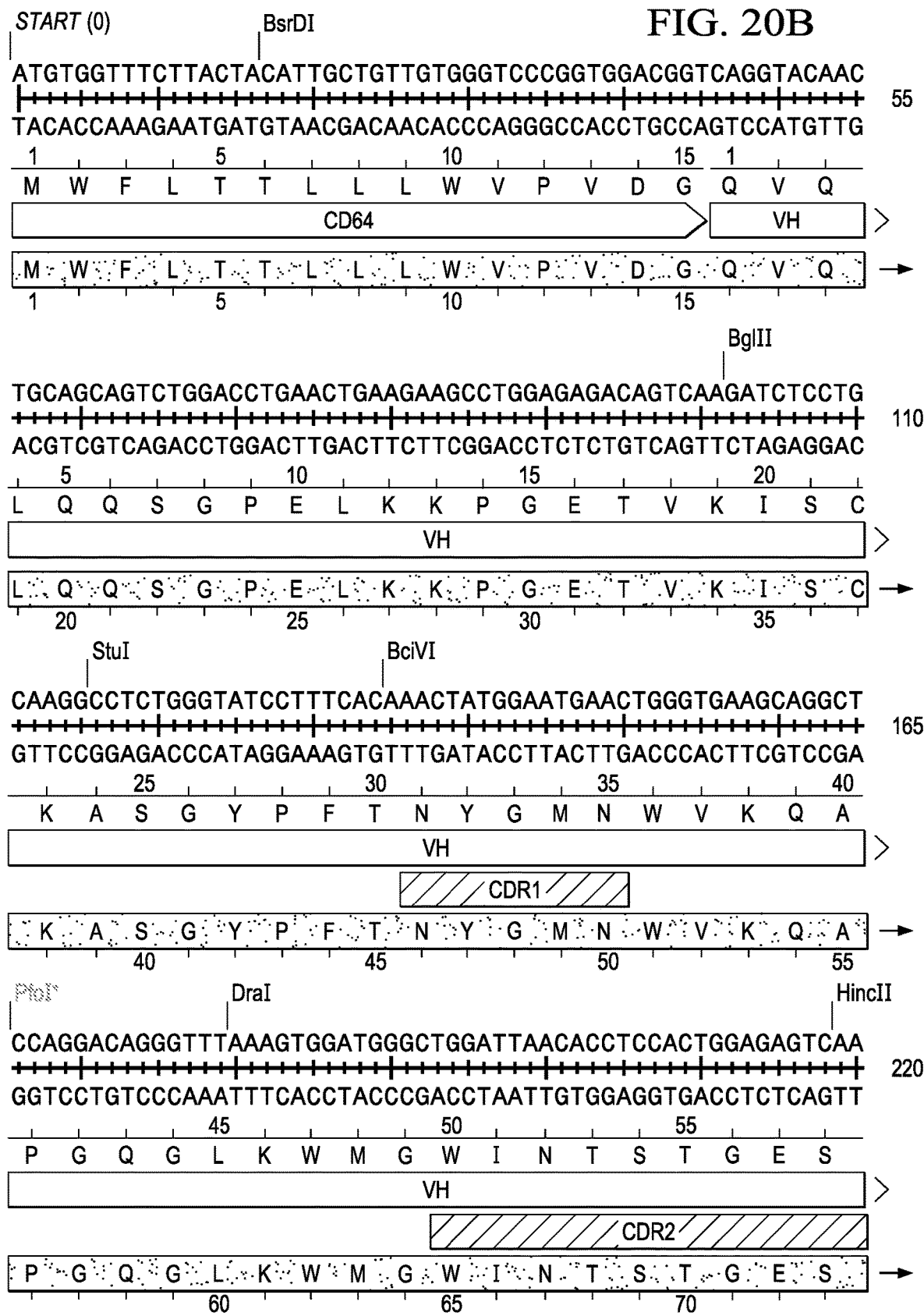
Figure 20B:
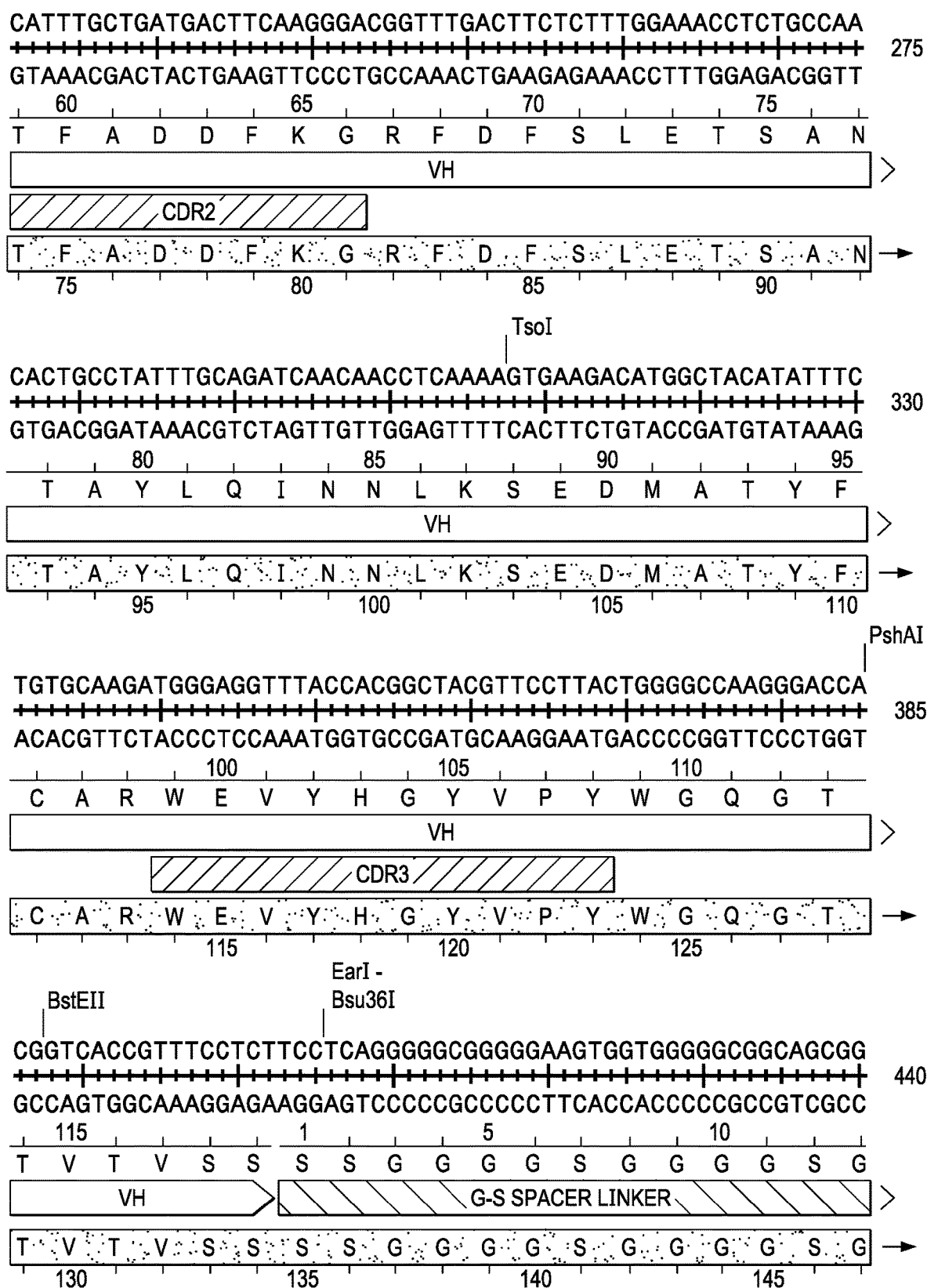
Figure 20B:
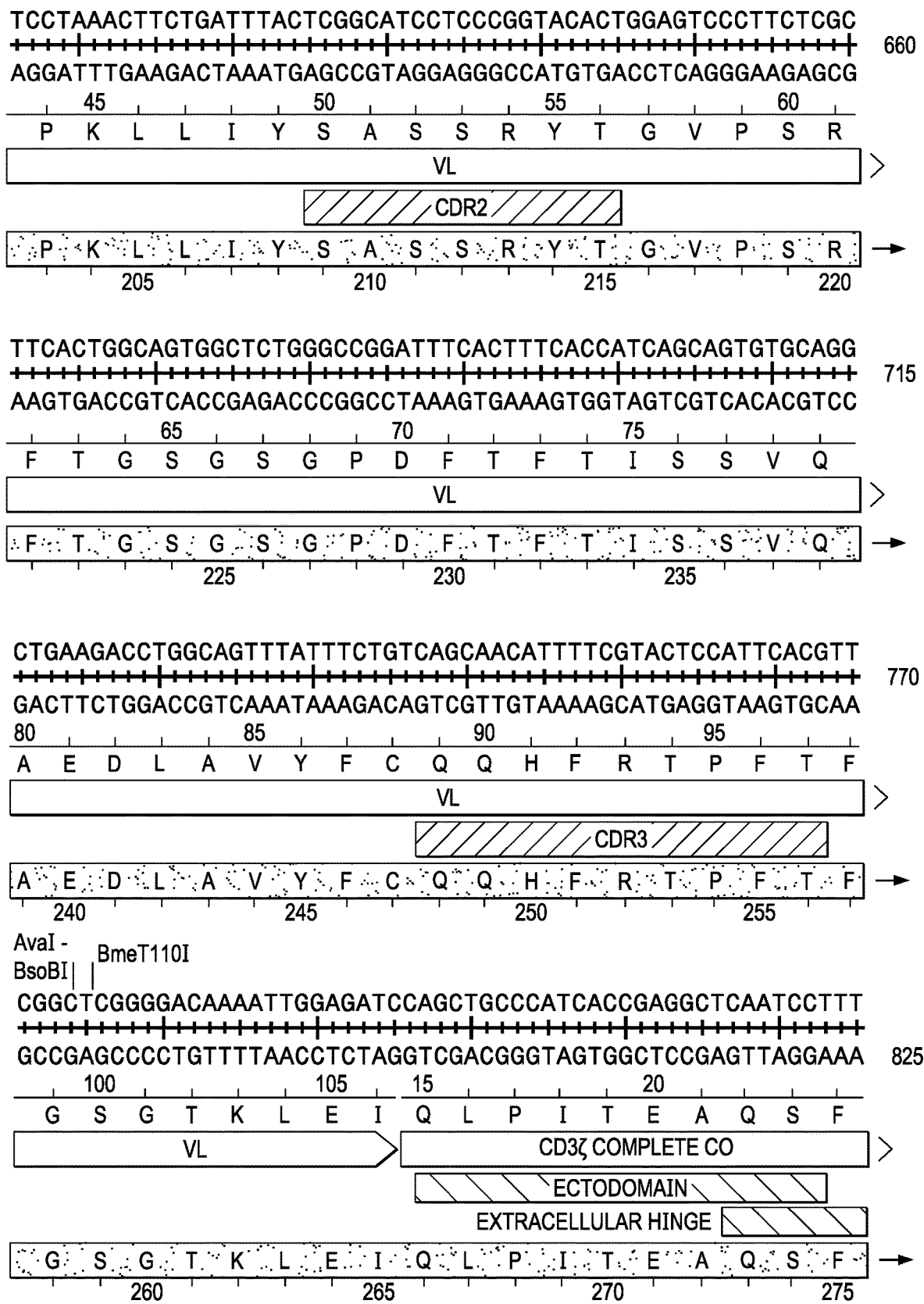
Figure 20B:
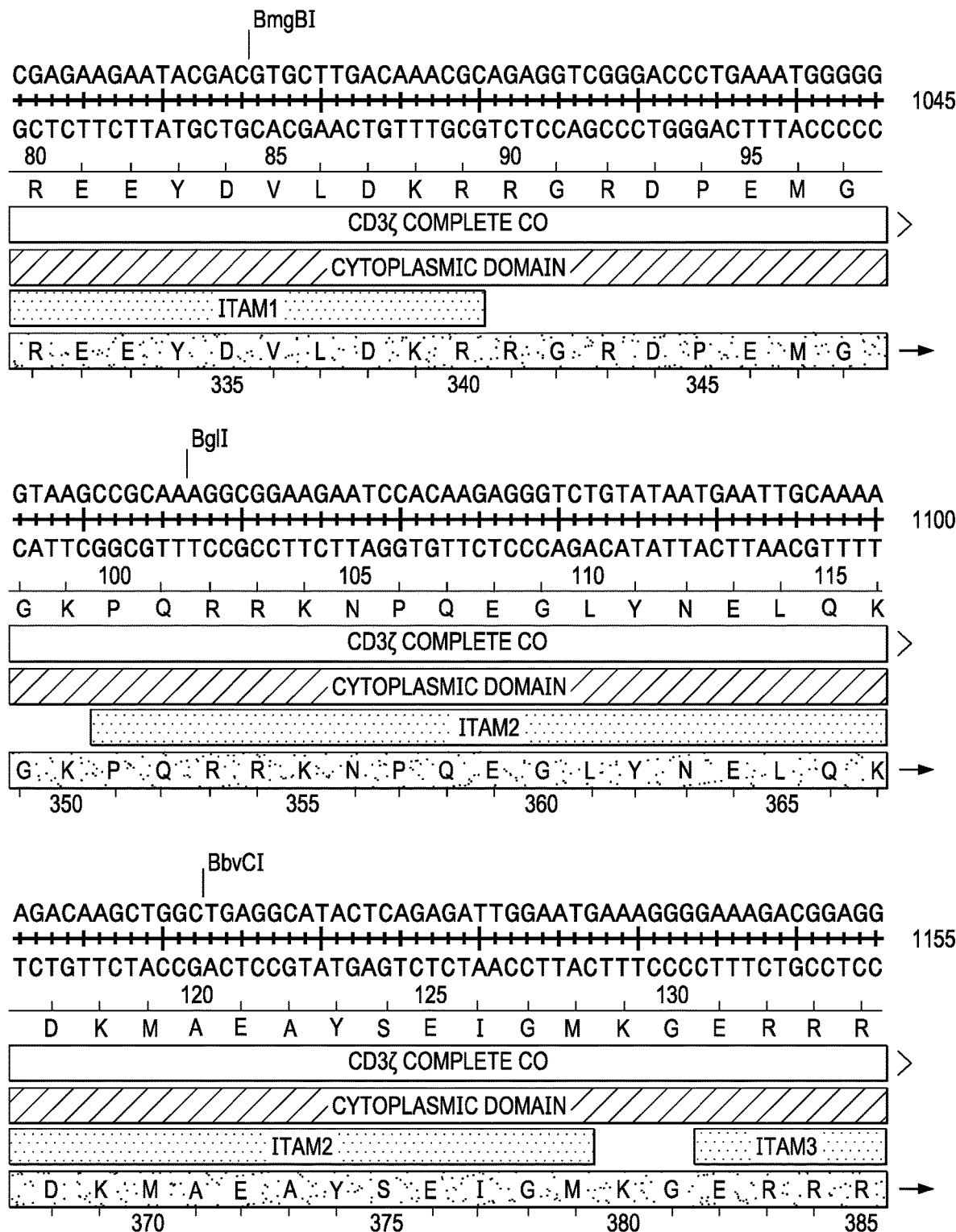

FIG. 20B shows a sequence alignment of the nucleotide sequence (SEQ ID NO: 31), amino acid sequence (SEQ ID NO: 32), CDRs, and domains of the construct illustrated in FIG. 20.

Figure 21A:
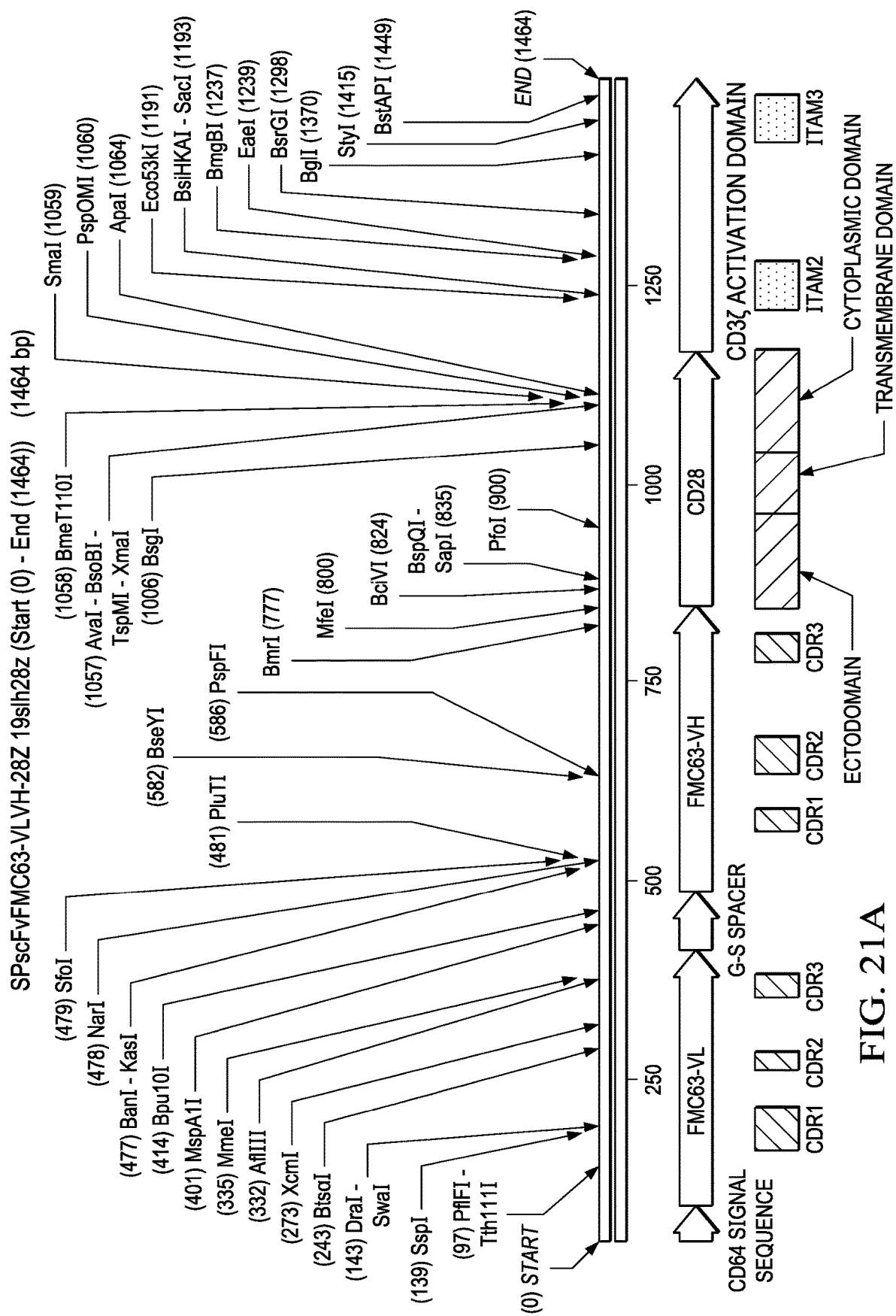
Figure 21B:
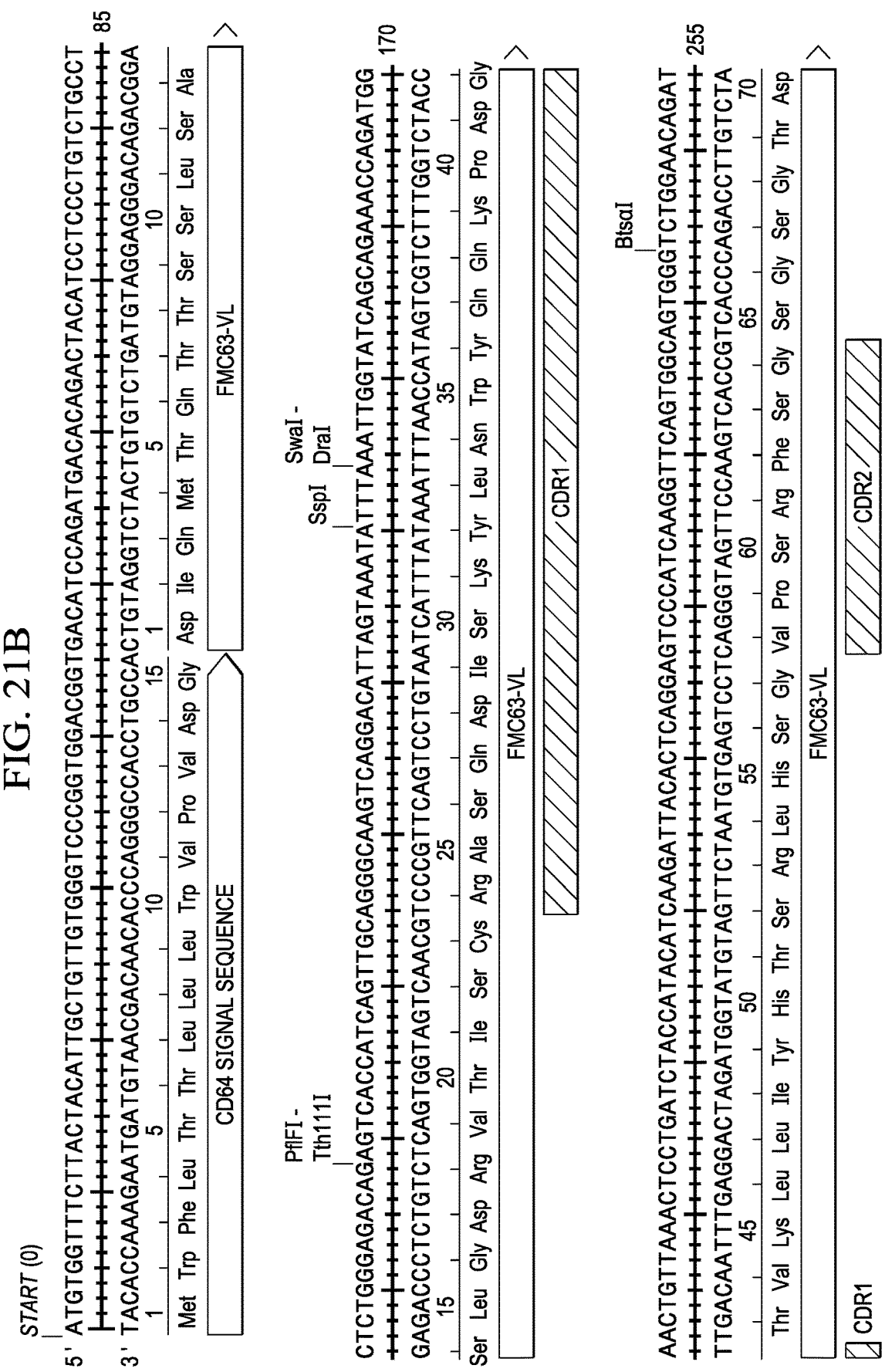
Figure 21B:
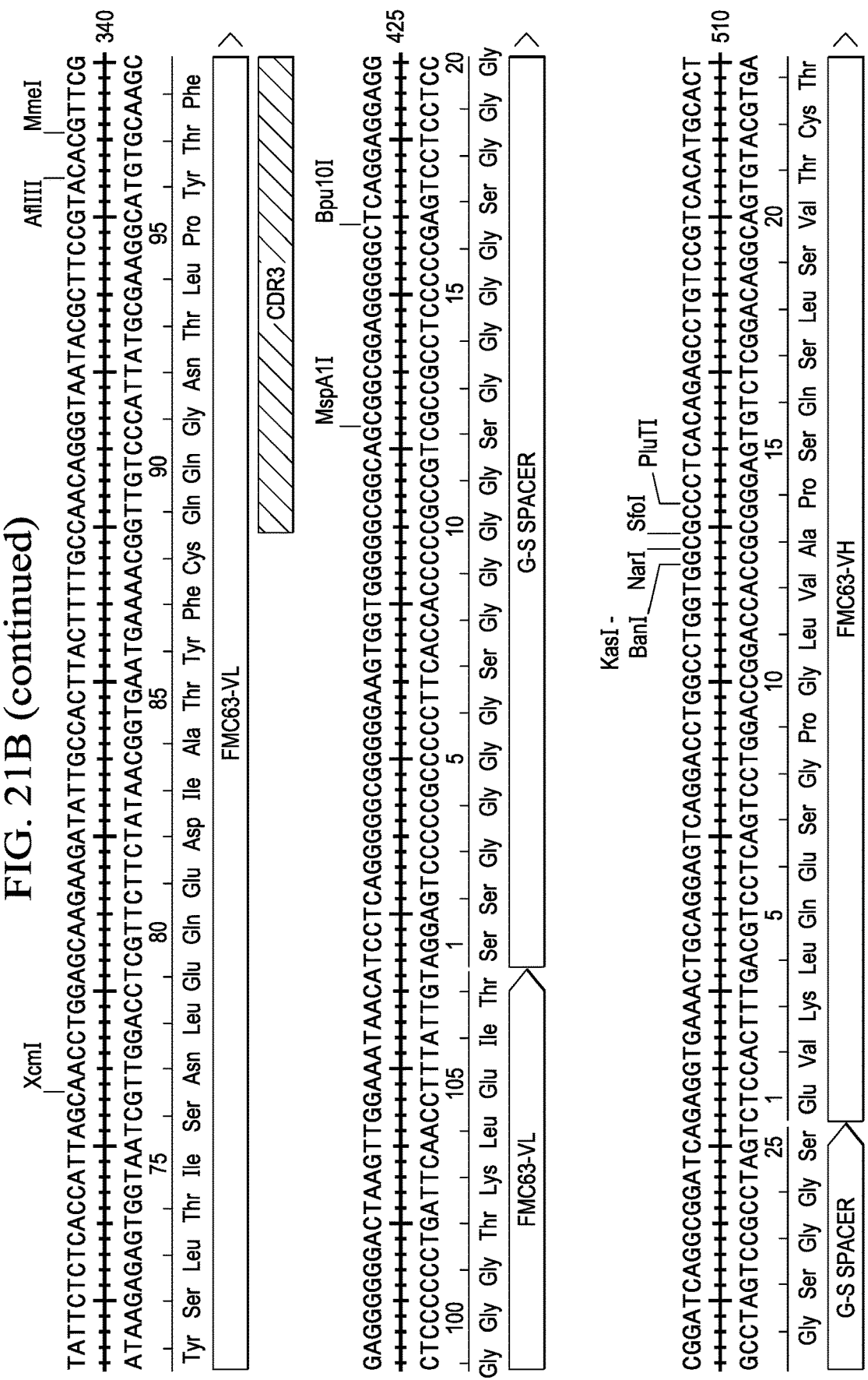
Figure 21B:
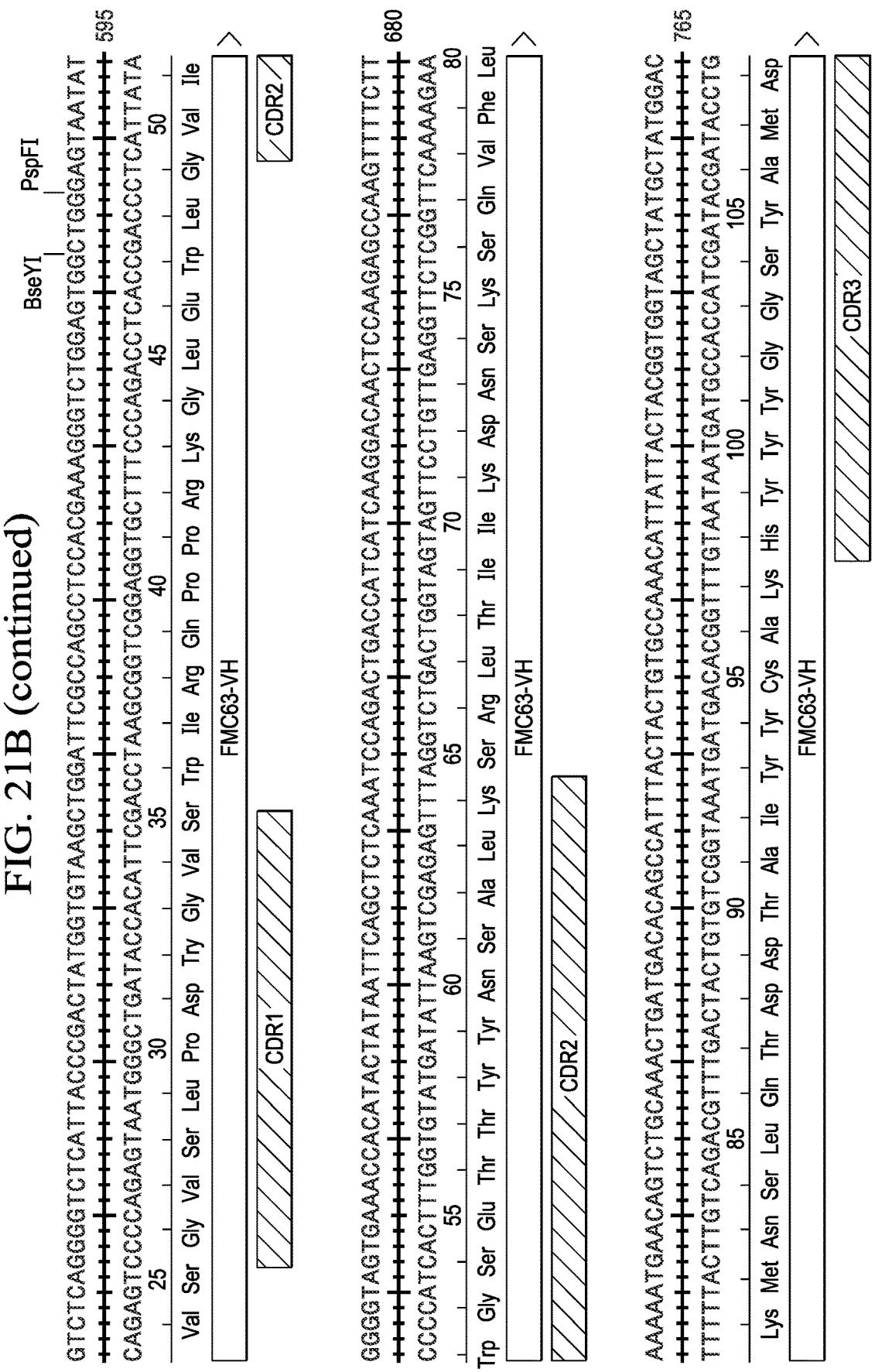
Figure 21B:
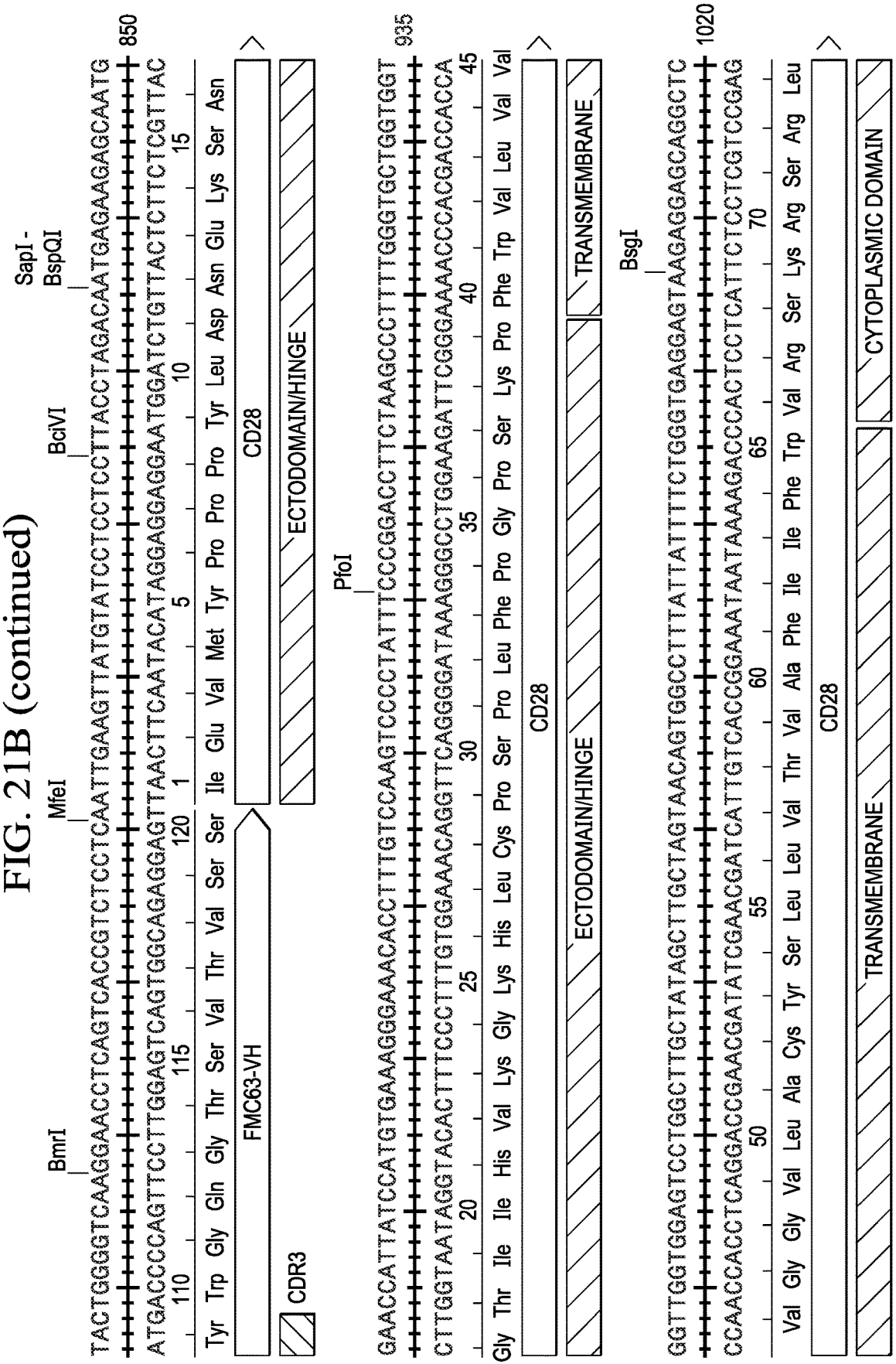
Figure 21B:
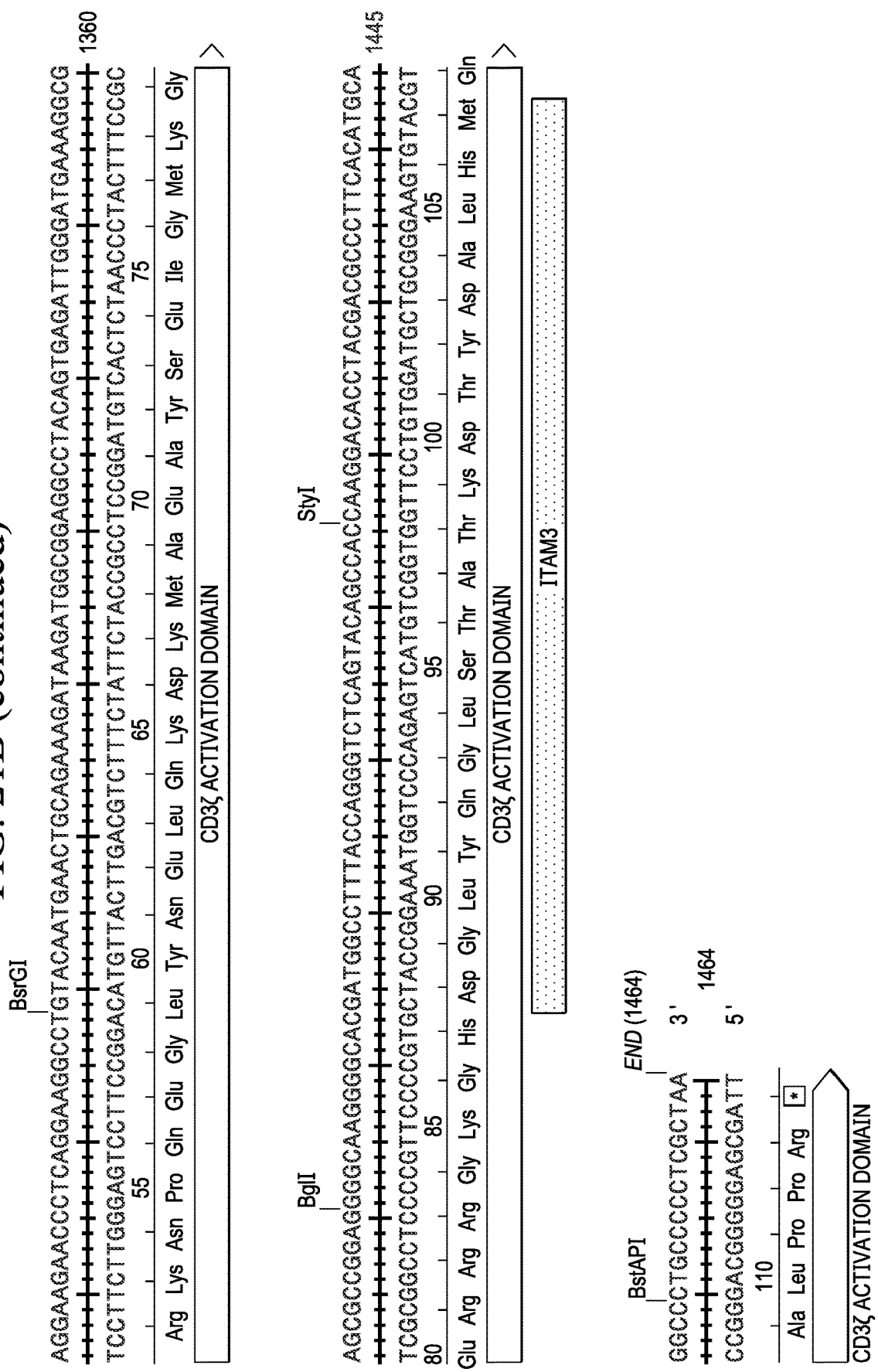

FIG. 21A shows the construction, orientation, and restriction sites of SPScFvFM63-VLVH-28Z 19 slh28ζ. FIG. 21B shows the sequence alignment, restriction sites, nucleotide sequence, and amino acid sequence of SPScFvFM63-VLVH-28Z 19 slh28ζ. The nucleotide sequence corresponds to, sequentially, SEQ ID NOs: 1-5 corresponding to CD64 signal sequence, FMC63-VL (also described as FMC63 light chain variable region), G-S spacer, FMC63-VH (also described as FMC63 heavy chain variable region), and collectively CD28 and CD3ζ activation domain (also described as the ectodomain, transmembrane, and signaling domains), respectively. The amino acid sequence corresponds to SEQ ID NO: 6, corresponding to CD19-SP-ScFvFMC63, and SEQ ID NO: 21, corresponding to CAR-CD19-CD28/CD3ζ.

FIG. 22A shows the construction and orientation of CD19-SPScFvFMC63, corresponding to a CD64 signal sequence, FMC63-VL, G-S spacer, and FMC63-VH, respectively. FIG. 22B shows the amino acid sequence of CD19-SPScFvFMC63 (SEQ ID NO: 6).

Figure 23A:
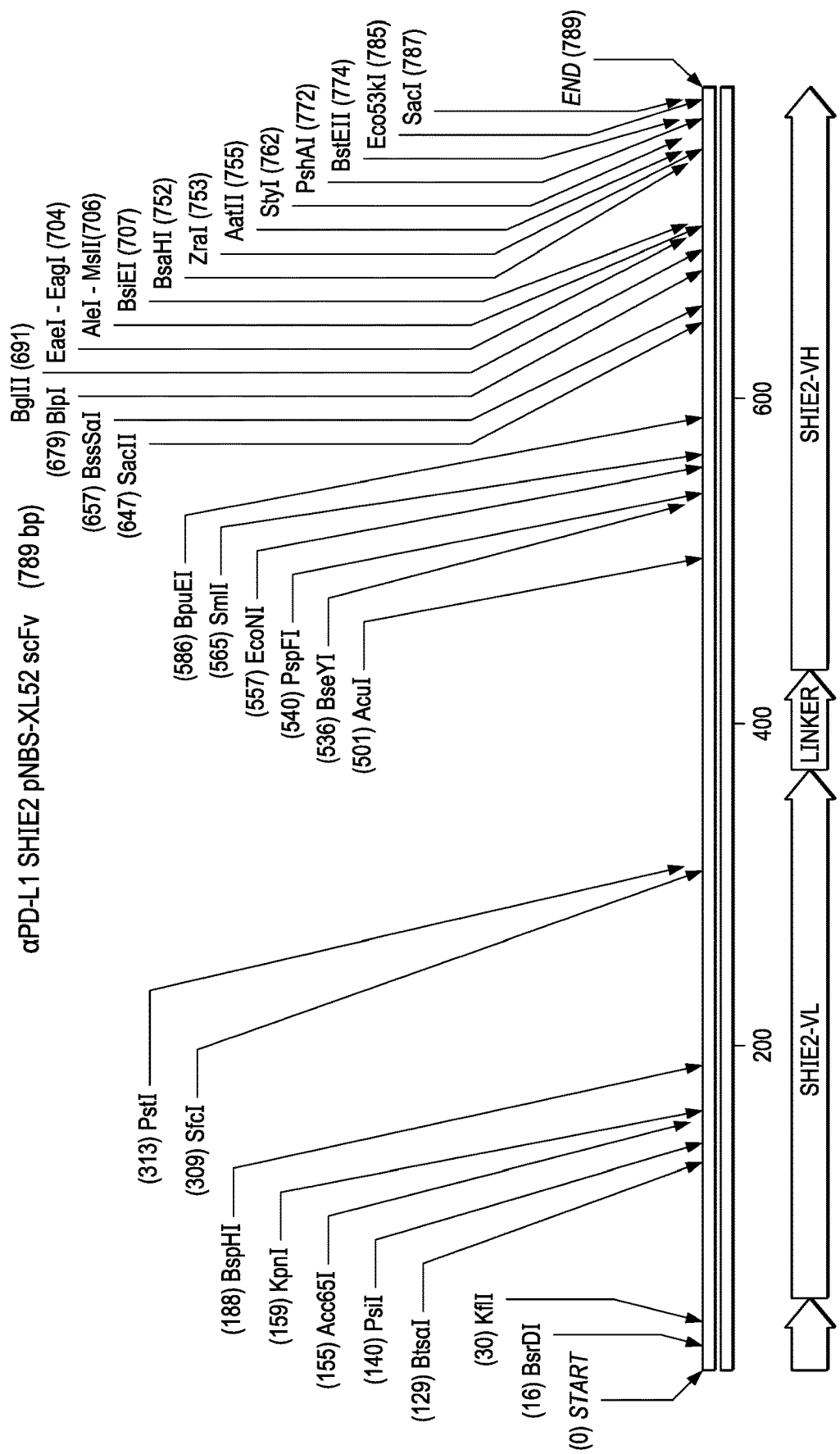
Figure 23B:
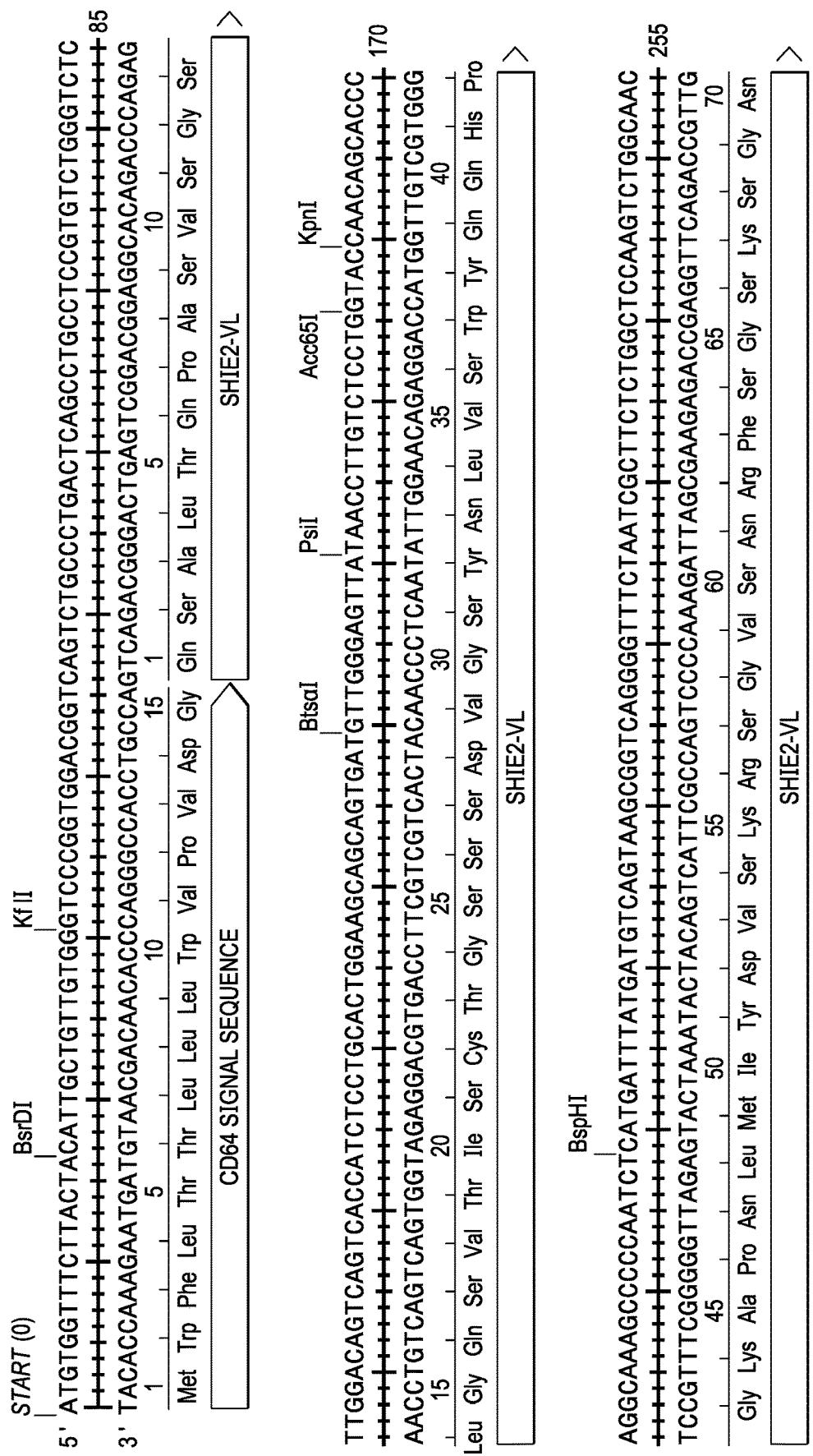
Figure 23B:
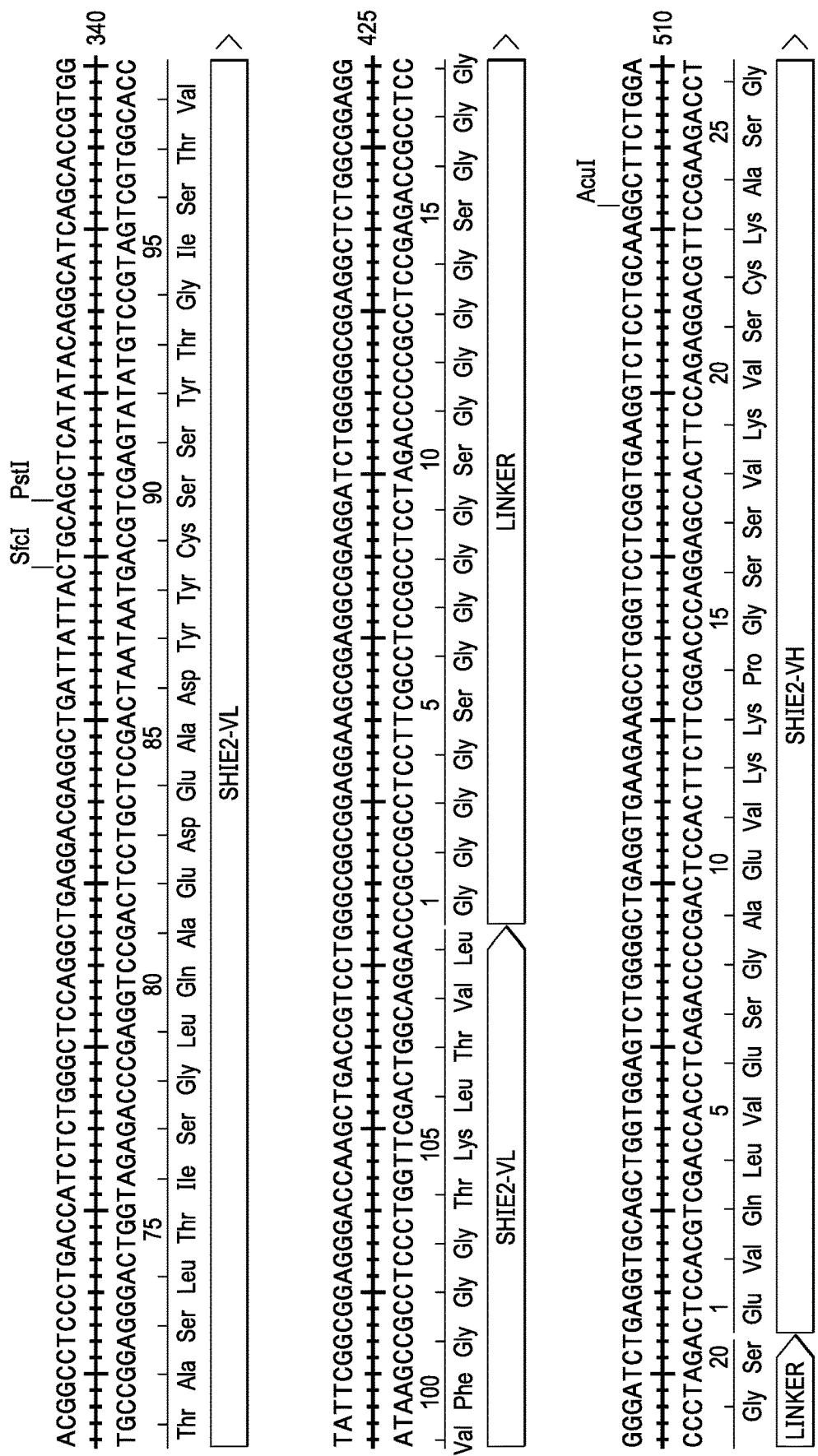
Figure 23B:
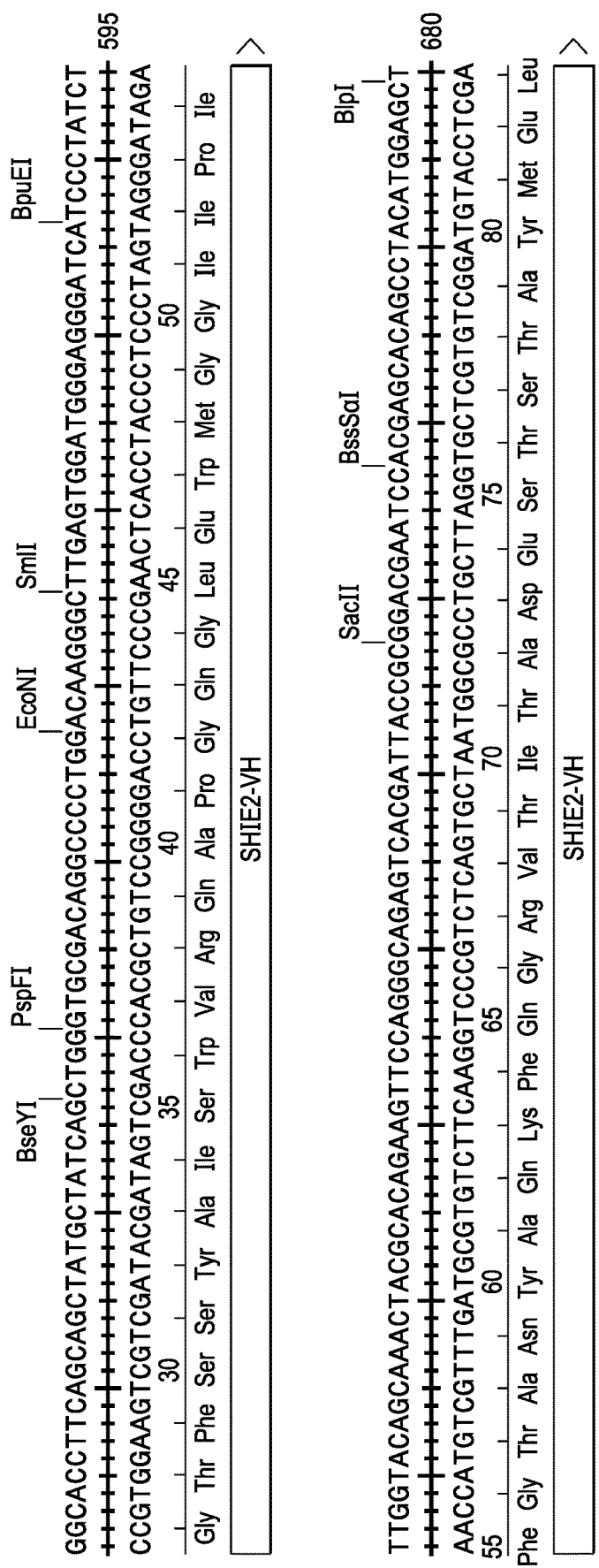
Figure 23B:
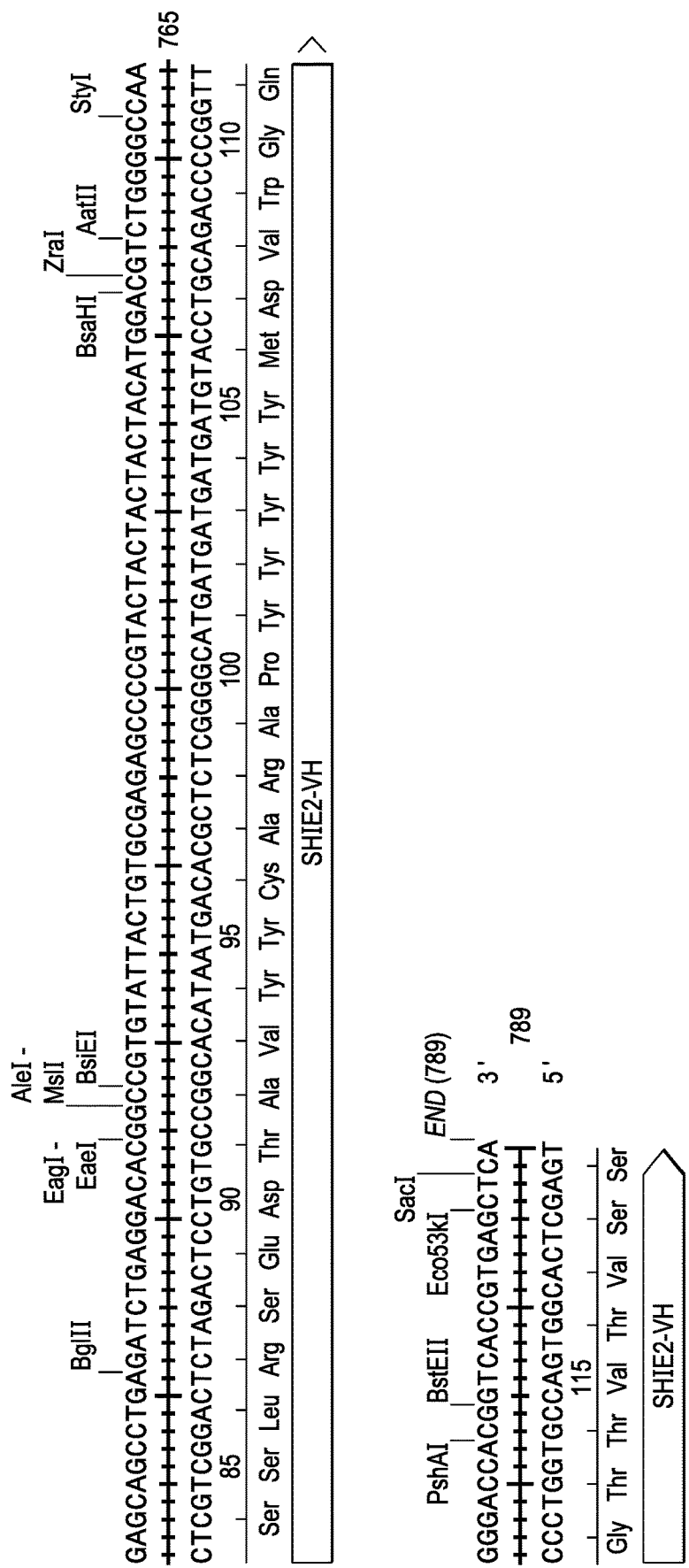

FIG. 23A shows the construction, orientation, and restriction sites of αPD-L1 SHIE2 pNBS-XL52 ScFv. FIG. 23B shows the sequence alignment, restriction sites, nucleotide sequence, and amino acid sequence of αPD-L1 SHIE2 pNBS-XL52 ScFv. The nucleotide sequence corresponds to, sequentially, SEQ ID NOs: 1, 7, 8, and 9, corresponding to CD64 signal sequence, SHIE2 VL (also described as SHIE2 light chain variable region), linker, and SHIE2 VH (also described as SHIE2 heavy chain variable region), respectively. The amino acid sequence corresponds to, sequentially, SEQ ID NOs: 38 and 33-35 corresponding to CD64, SHIE2 VL, linker, and SHIE2 VH, respectively.

Figure 24A:
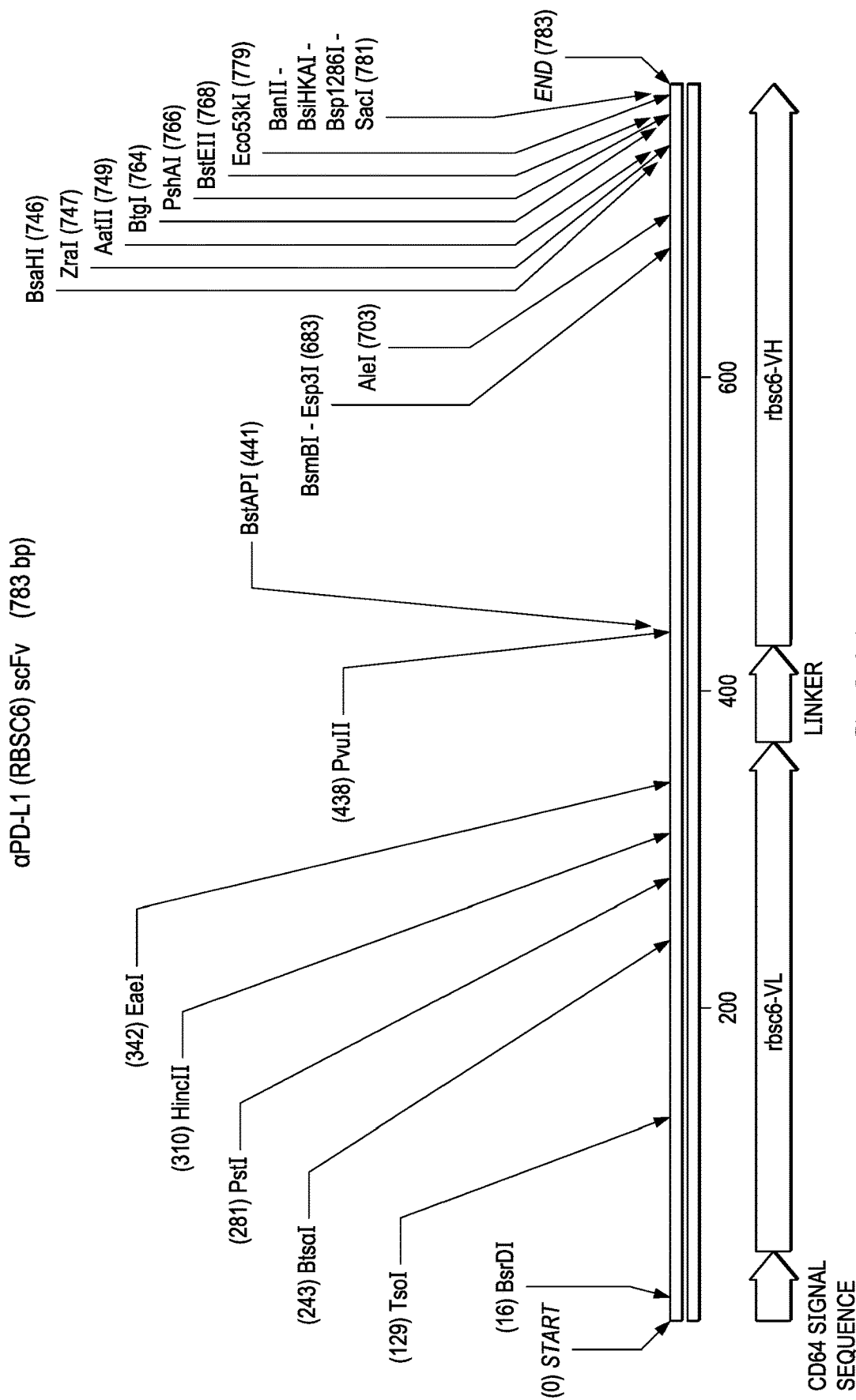
Figure 24B:
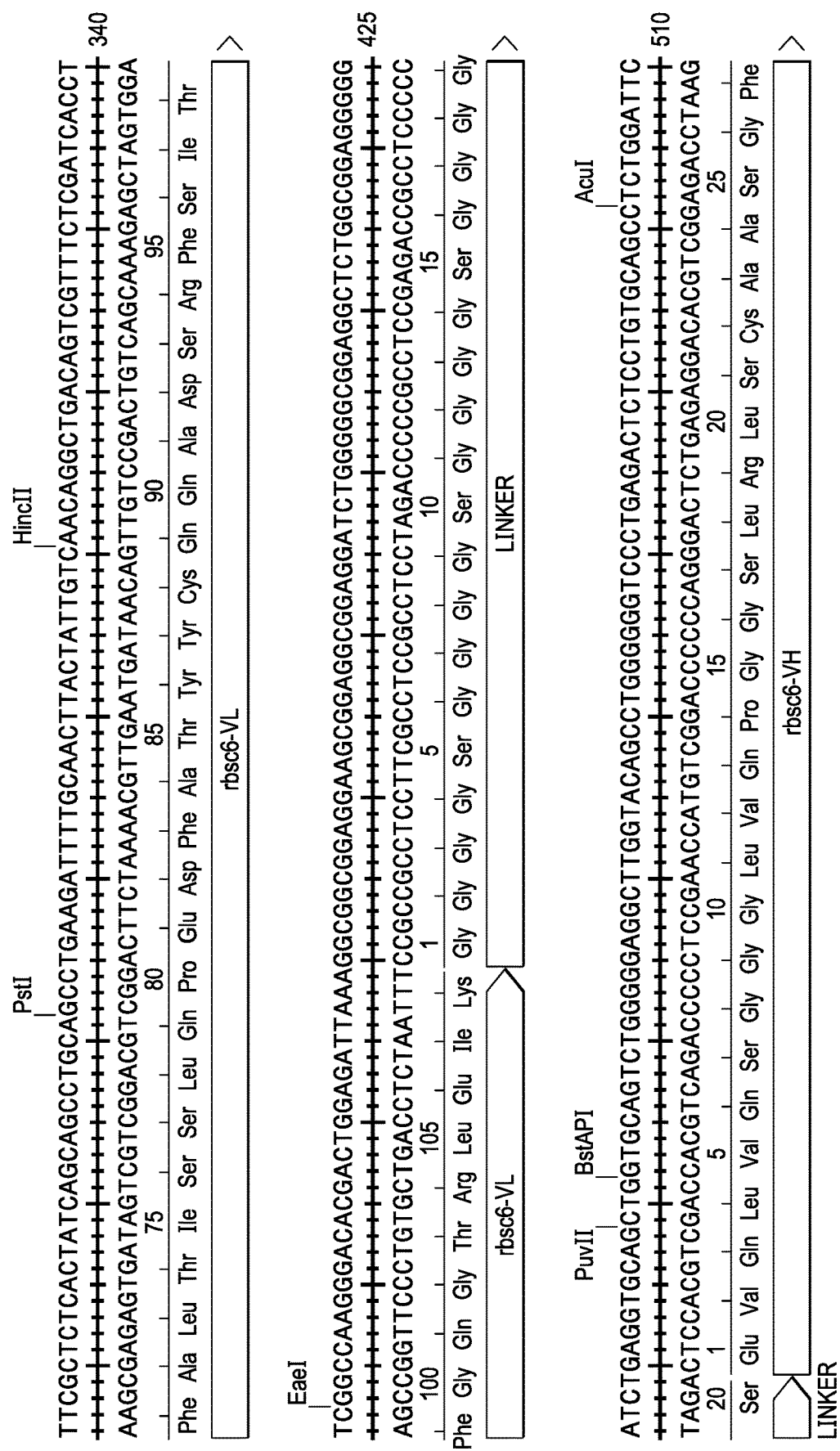
Figure 24B:
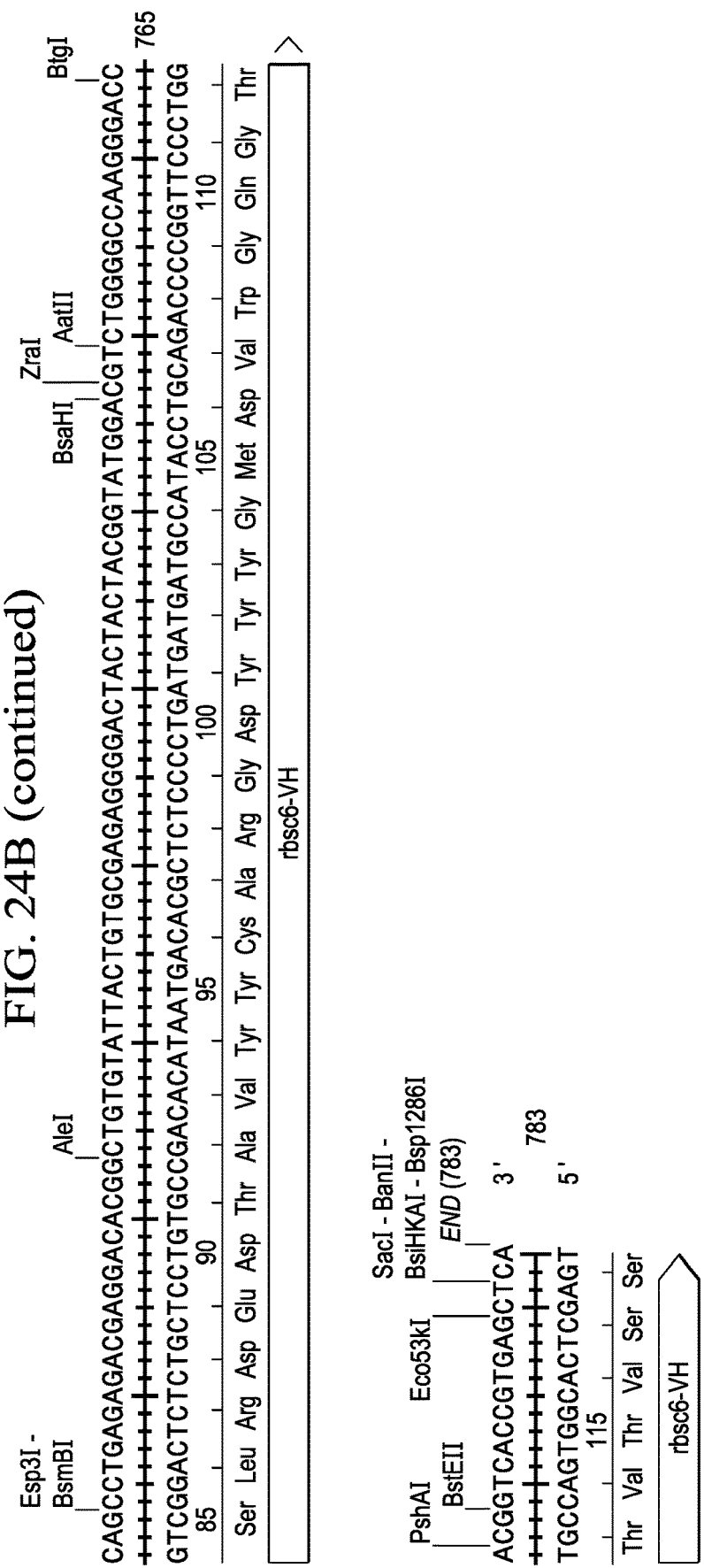

FIG. 24A shows the construction, orientation, and restriction sites of αPD-L1 (RBSC6) ScFv, corresponding to a CD64 signal sequence, RBSC6 VL, linker, and RBSC6 VH, respectively. FIG. 24B shows the sequence alignment, restriction sites, nucleotide sequence, and amino acid sequence of αPD-L1 (RBSC6) ScFv. The nucleotide sequence corresponds to, sequentially, SEQ ID NOs: 1, 10, 8, and 12, corresponding to CD64 signal sequence, RBSC6 VL (also described as RBSC6 light chain variable region), linker, and RBSC6 VH (also described as RBSC6 heavy chain variable region), respectively. The amino acid sequence corresponds to, sequentially, SEQ ID NOs: 38, 36, 34, and 37 corresponding to CD64, RBSC6 VL, linker, and RBSC6 VH, respectively.

Figure 25A:
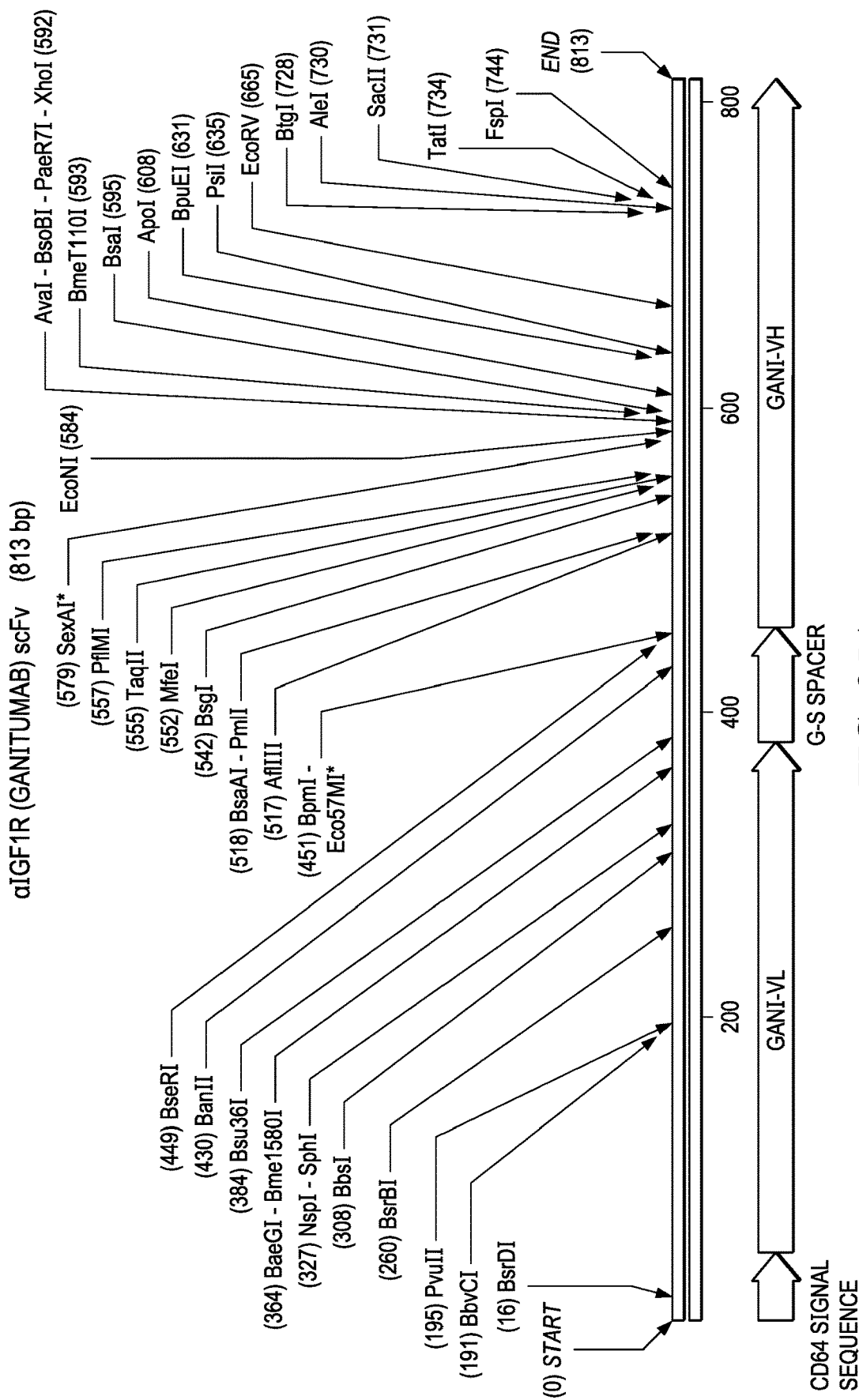
Figure 25B:
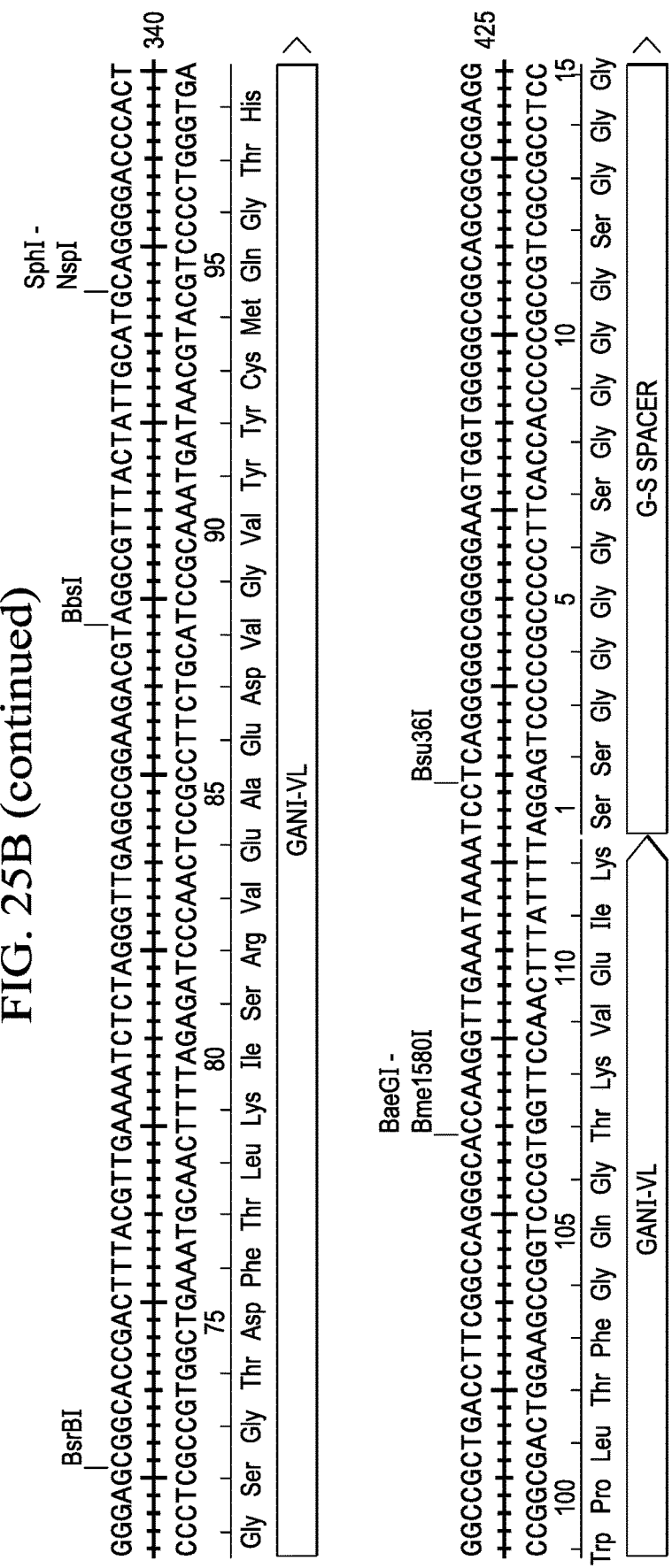
Figure 25B:
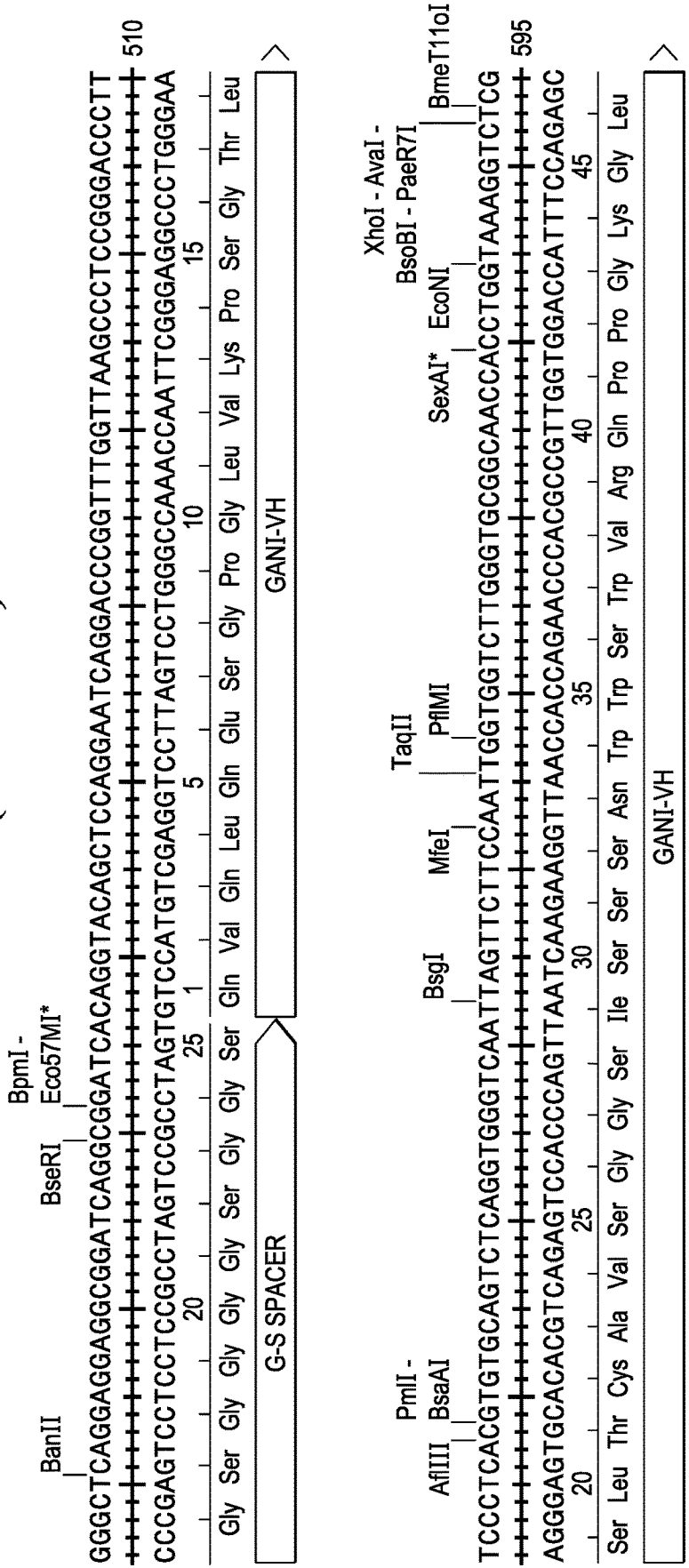
Figure 25B:
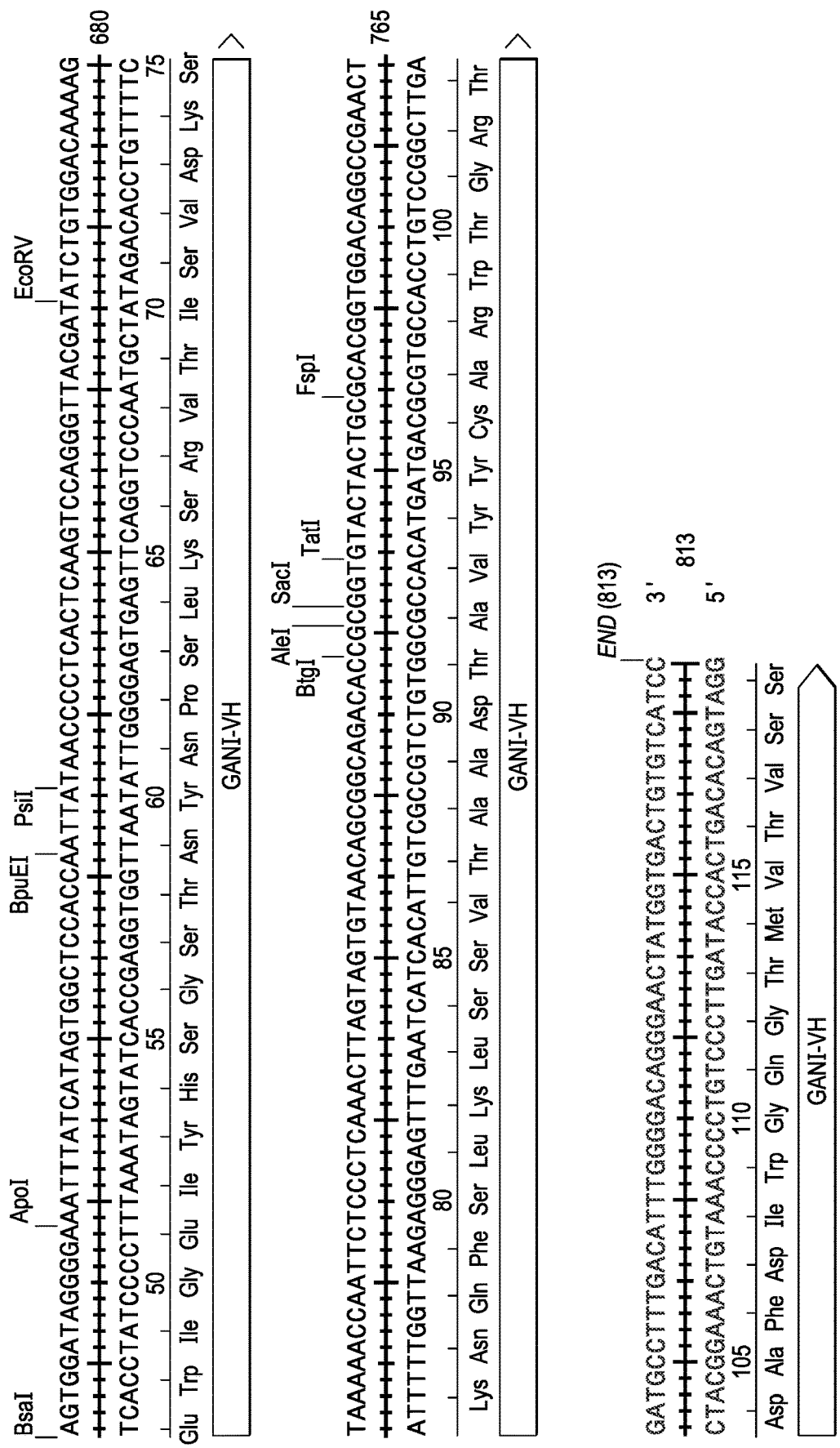

FIG. 25A shows the construction, orientation, and restriction sites of αIGF1R (Ganitumab) ScFv, corresponding to a CD64 signal sequence, Gani VL, G-S spacer, and Gani VH, respectively. FIG. 25B shows the sequence alignment, restriction sites, nucleotide sequence, and amino acid sequence of αIGF1R (Ganitumab) ScFv. The nucleotide sequence corresponds to, sequentially, SEQ ID NOs: 1, 13, 3, and 14, corresponding to CD64 signal sequence, Gani VL (also described as Ganitumab light chain variable region), G-S spacer, and Gani VH (also described as Ganitumab heavy chain variable region), respectively. The amino acid sequence corresponds to, sequentially, SEQ ID NOs: 38, 40, 39, and 41 corresponding to CD64, Gani VL, G-S spacer, and Gani VH, respectively.

Figure 26A:
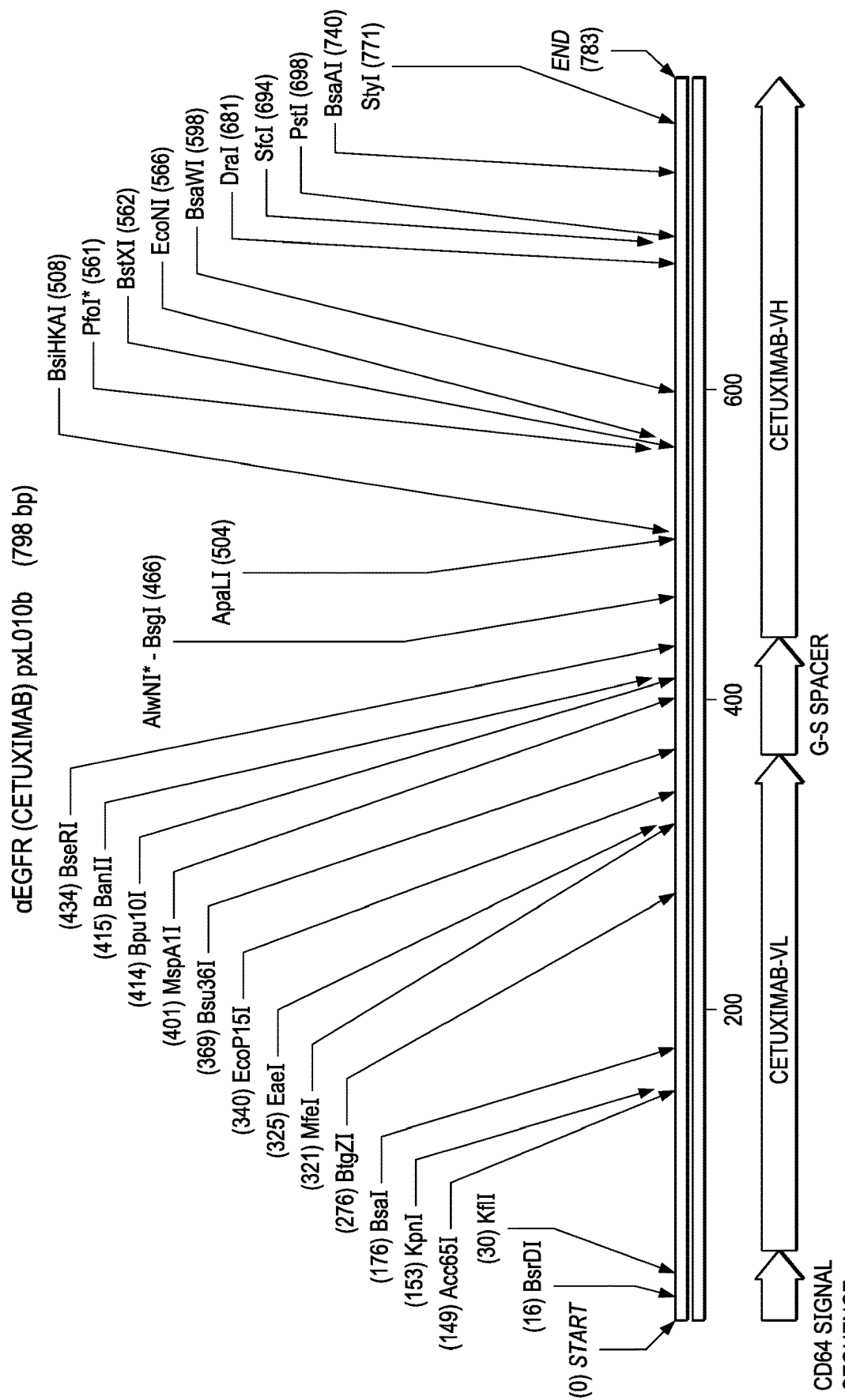
Figure 26B:
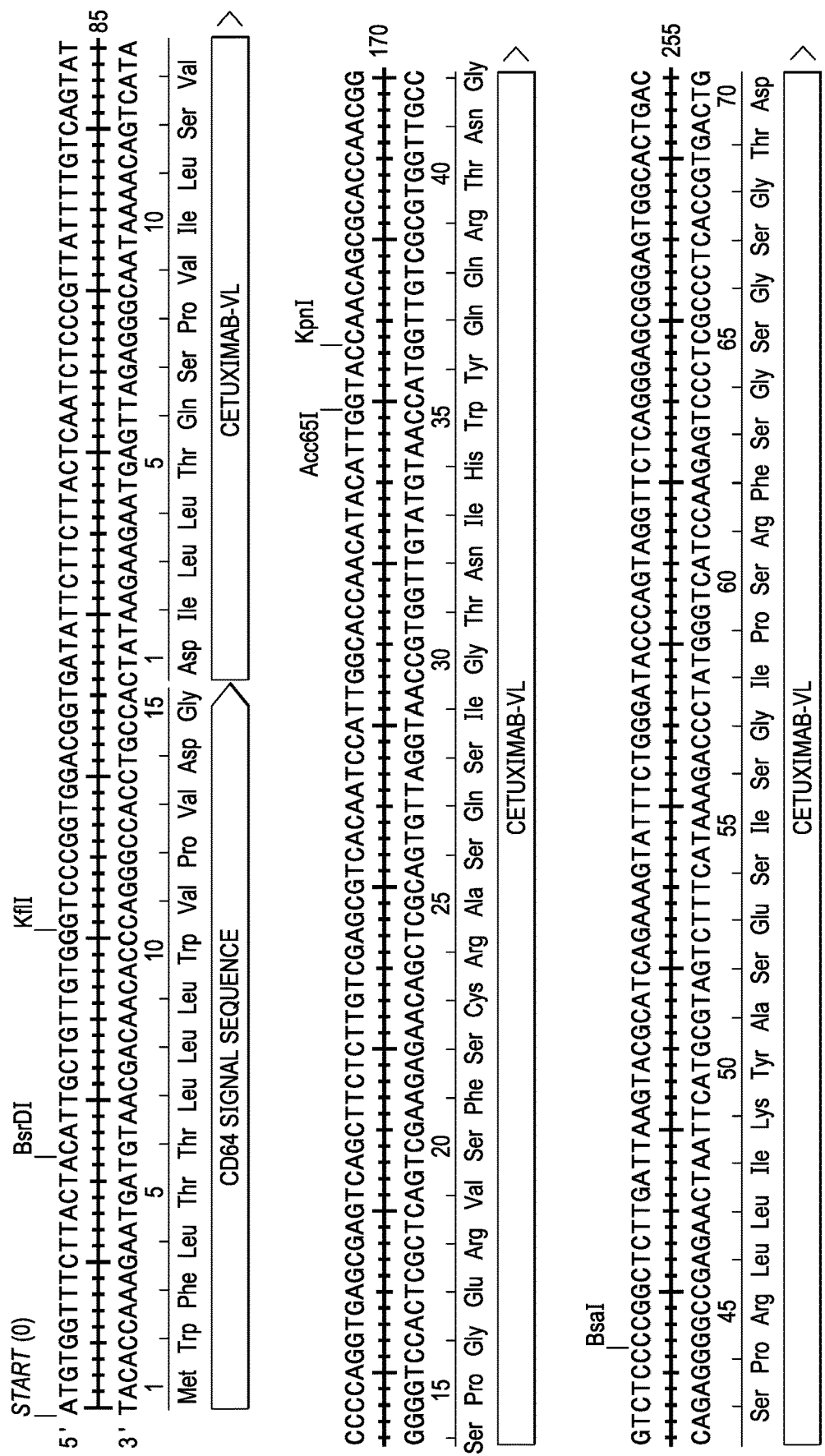
Figure 26B:
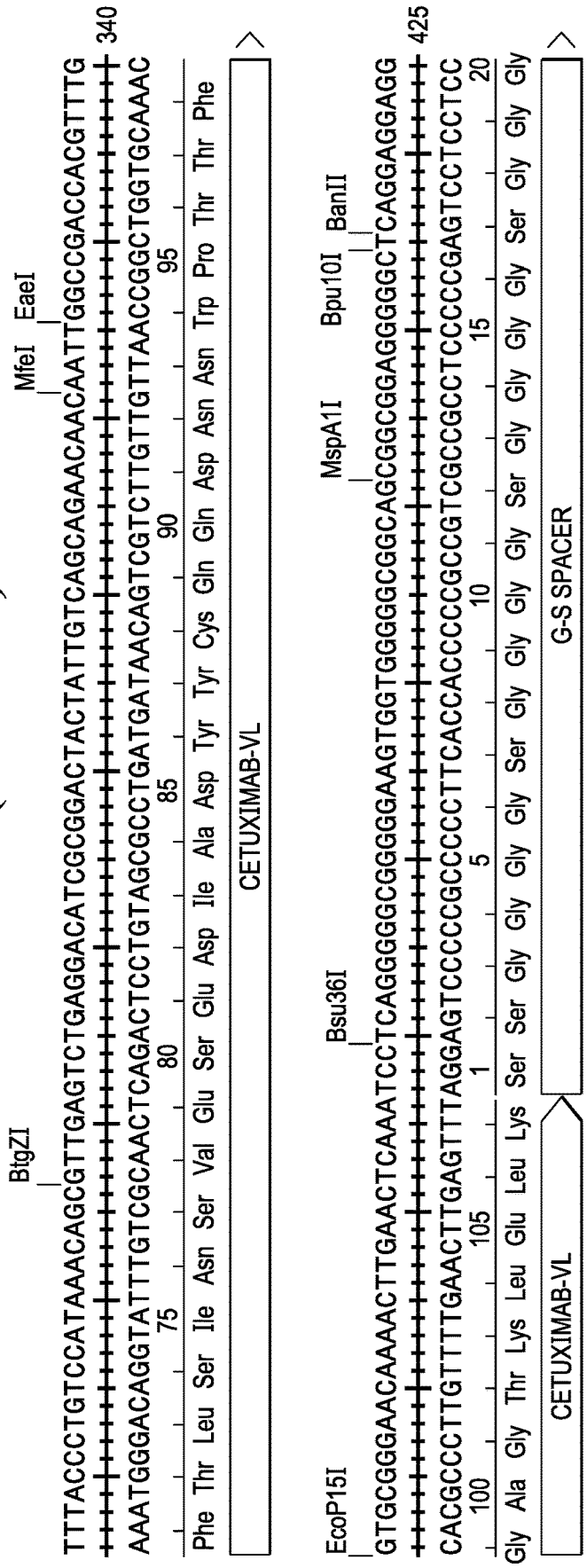
Figure 26B:
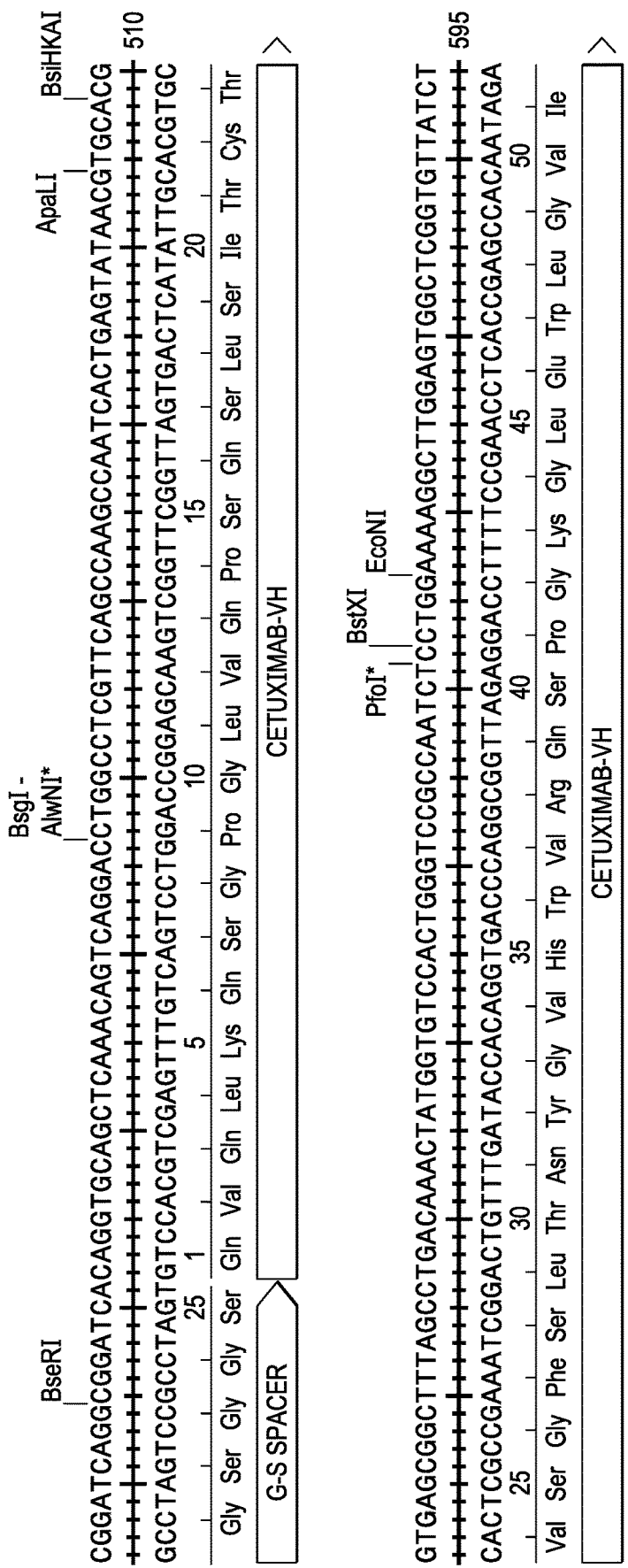
Figure 26B:
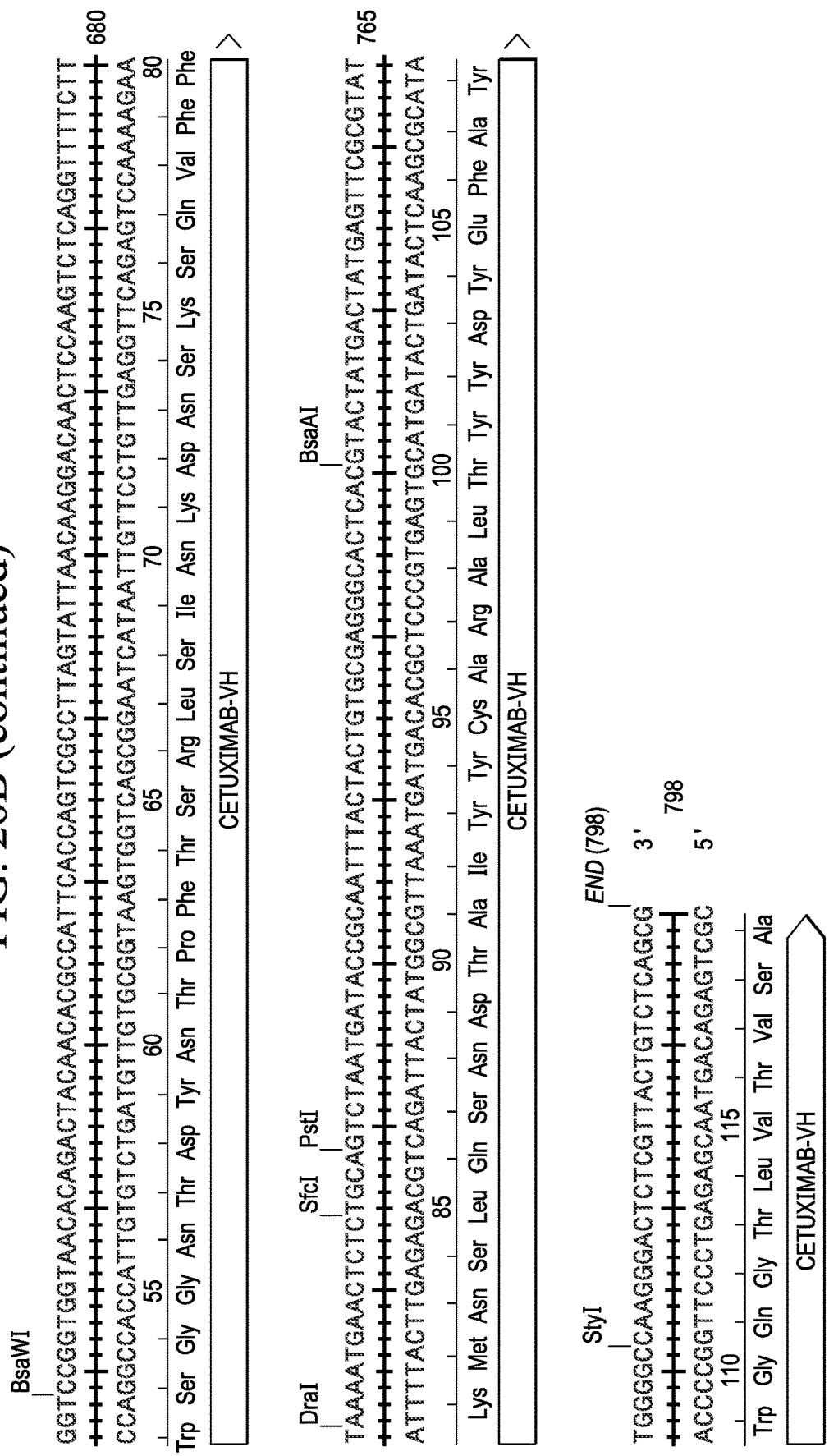

FIG. 26A shows the construction, orientation, and restriction sites of αEGFR (Cetuximab) pXL101b, corresponding to a CD64 signal sequence, Cetuximab VL, G-S spacer, and Cetuximab VH, respectively. FIG. 26B shows the sequence alignment, restriction sites, nucleotide sequence, and amino acid sequence of αEGFR (Cetuximab) pXL101b. The nucleotide sequence corresponds to, sequentially, SEQ ID NOs: 1, 15, 3, and 16, corresponding to CD64 signal sequence, Cetuximab VL (also described as Cetuximab light chain variable region), G-S spacer, and Cetuximab VH (also described as Ganitumab heavy chain variable region), respectively. The amino acid sequence corresponds to, sequentially, SEQ ID NOs: 38, 42, 39, and 43 corresponding to CD64, Cetuximab VL, G-S spacer, and Cetuximab VH, respectively.

Figure 27A:
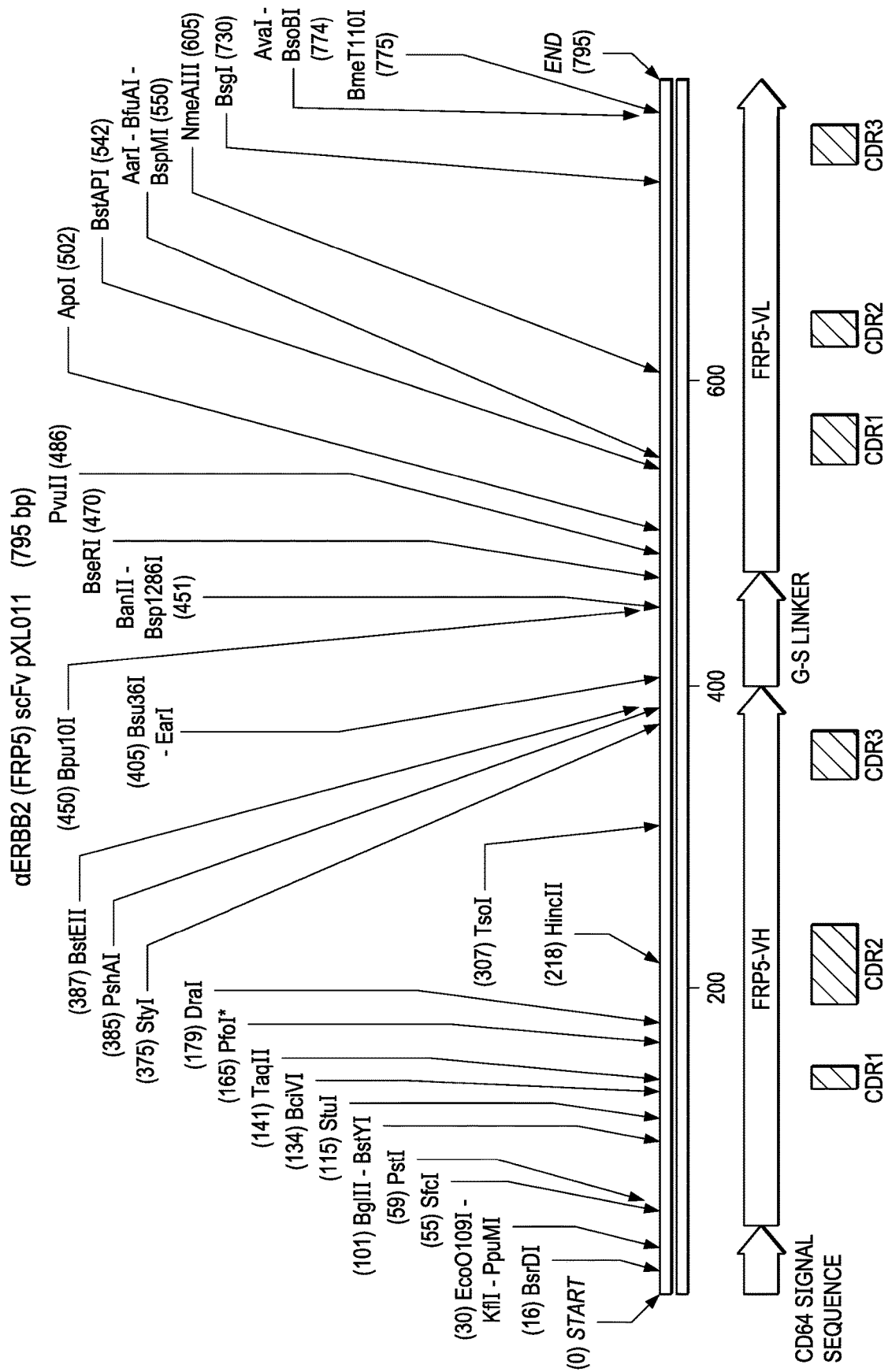
Figure 27B:
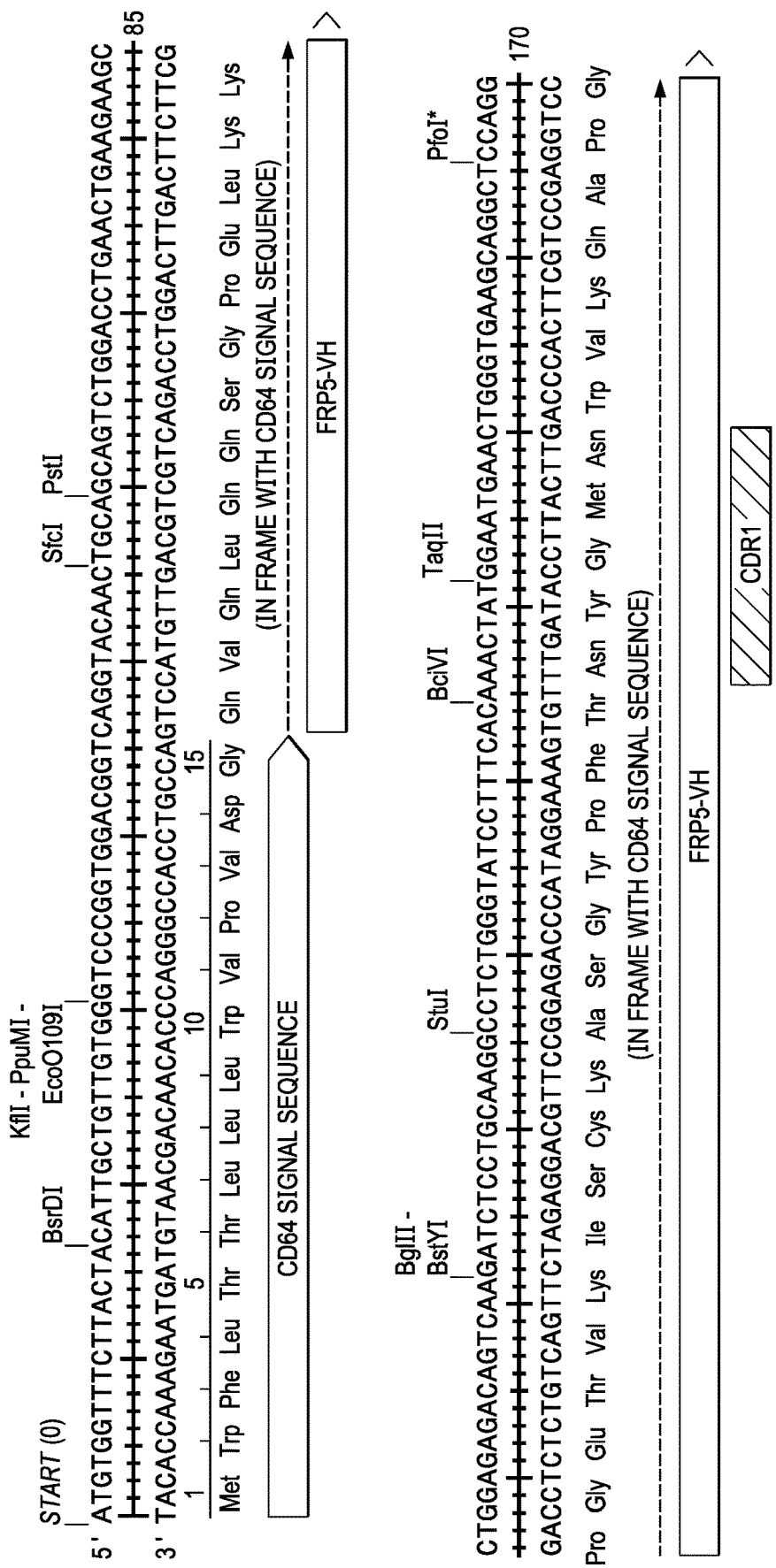
Figure 27B:
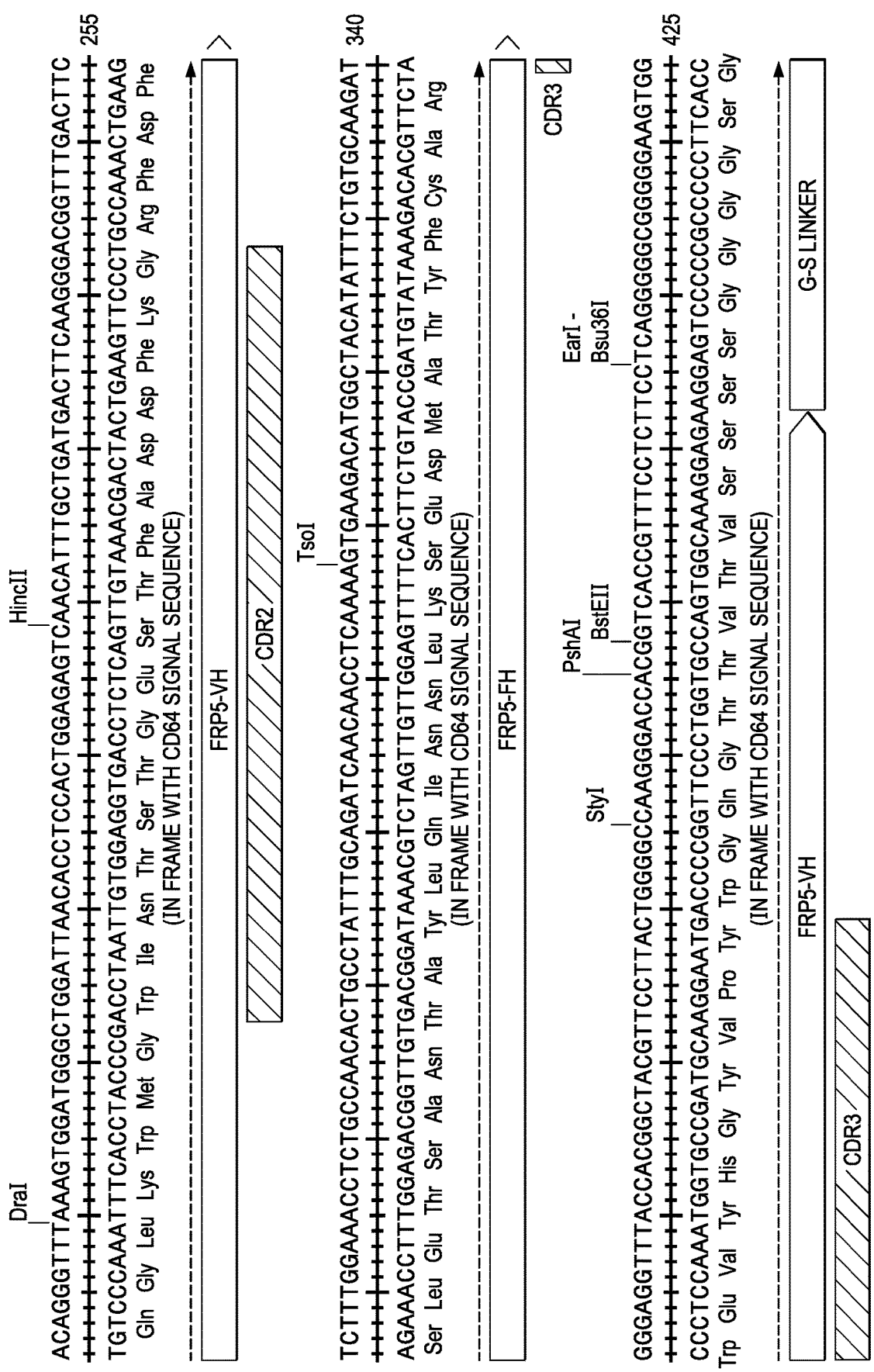
Figure 27B:
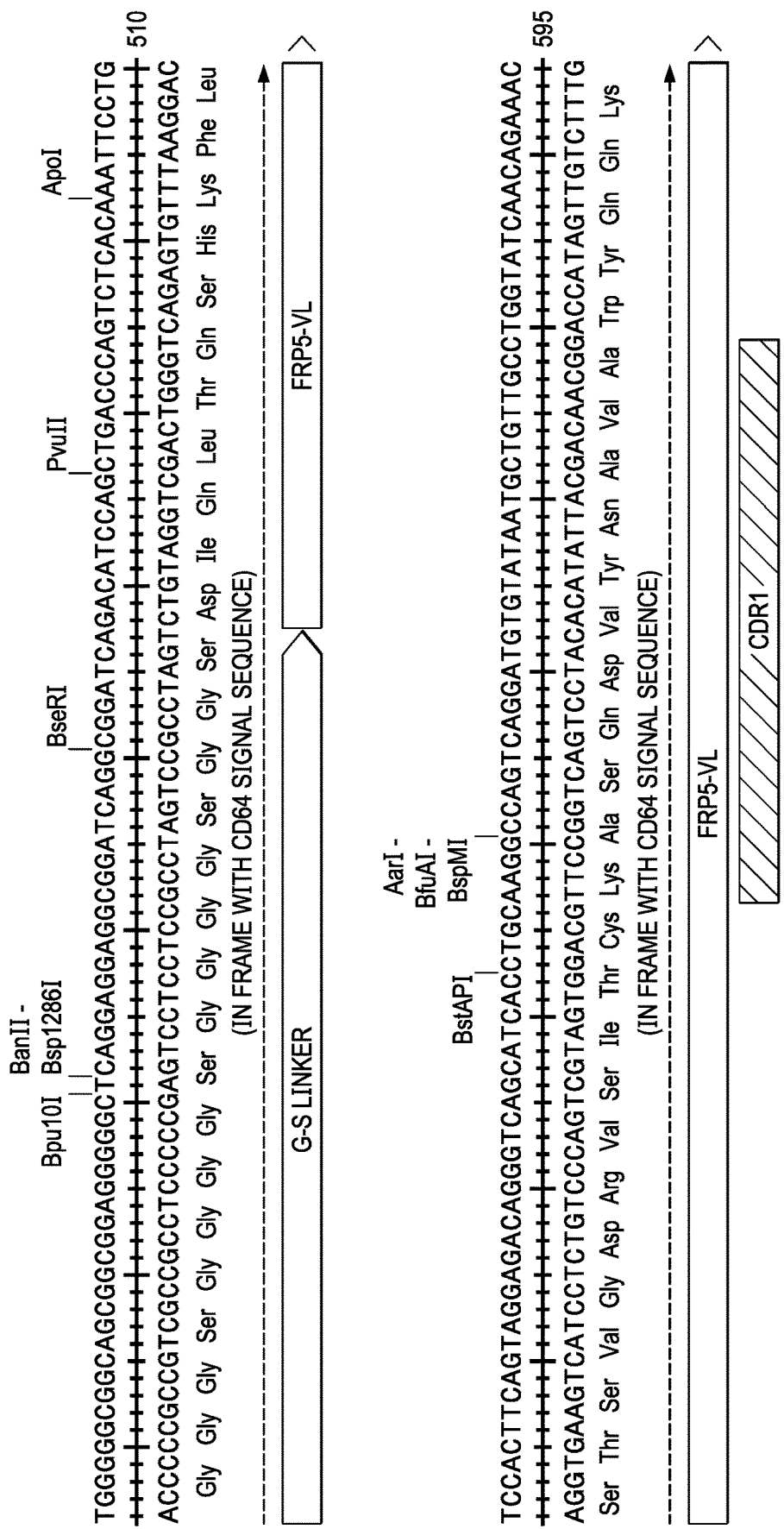
Figure 27B:
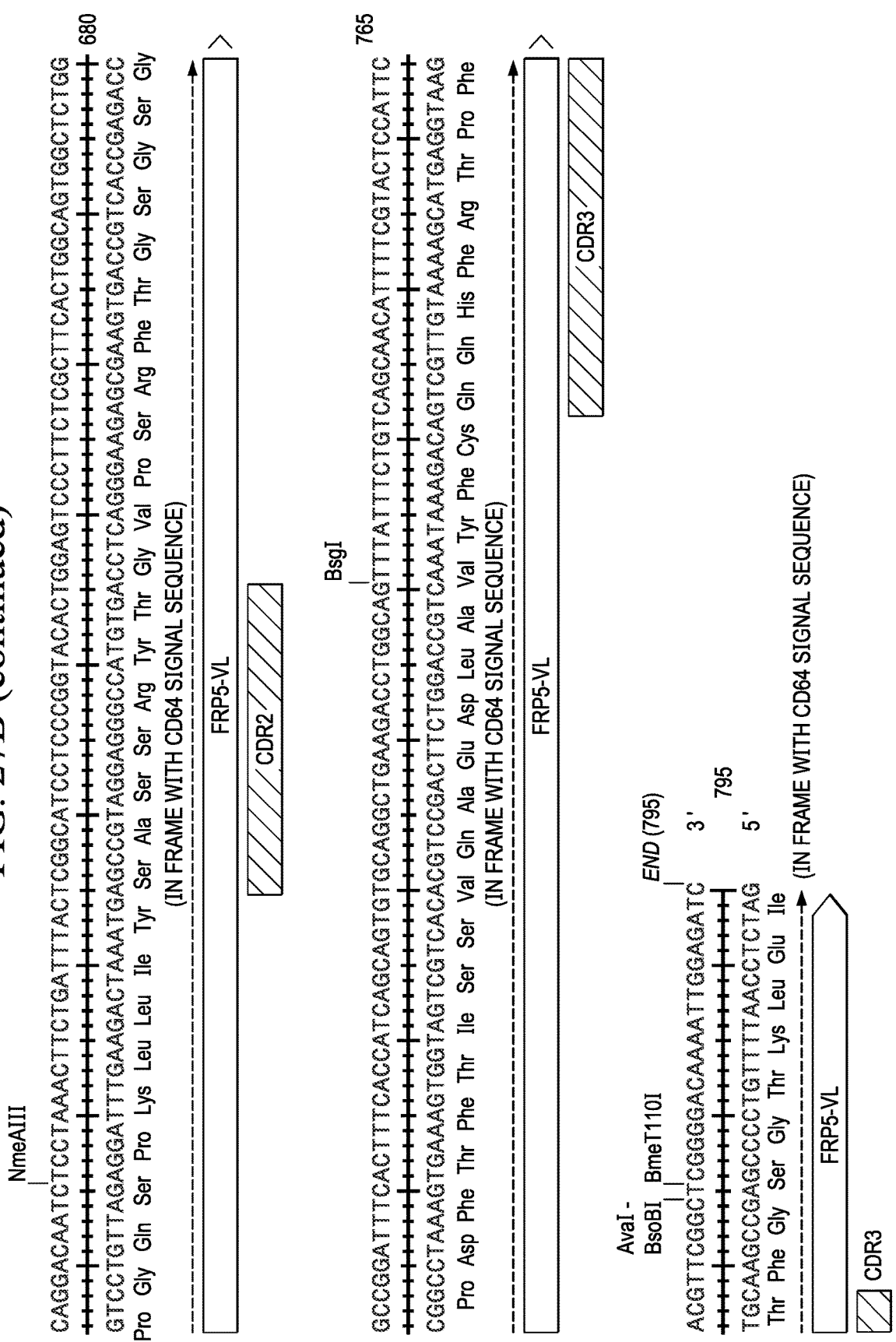

FIG. 27A shows the construction, orientation, and restriction sites of αERBB2 (FRP5) ScFv pXL011, corresponding to a CD64 signal sequence, FRP5 VH, G-S linker, and FRP5 VL, respectively. FIG. 27B shows the sequence alignment, restriction sites, nucleotide sequence, and amino acid sequence of αERBB2 (FRP5) ScFv pXL011. The nucleotide sequence corresponds to, sequentially, SEQ ID NOs: 1, 17, 3, and 18, corresponding to CD64 signal sequence, FRP5 VH (also described as FRP5 heavy chain variable region), G-S linker, and FRP5 VL (also described as FRP5 light chain variable region), respectively. The amino acid sequence corresponds to, sequentially, SEQ ID NOs: 38, 44, 39, and 45 corresponding to CD64, FRP5 VL, G-S linker, and FRP5 VH, respectively.

Figure 28A:
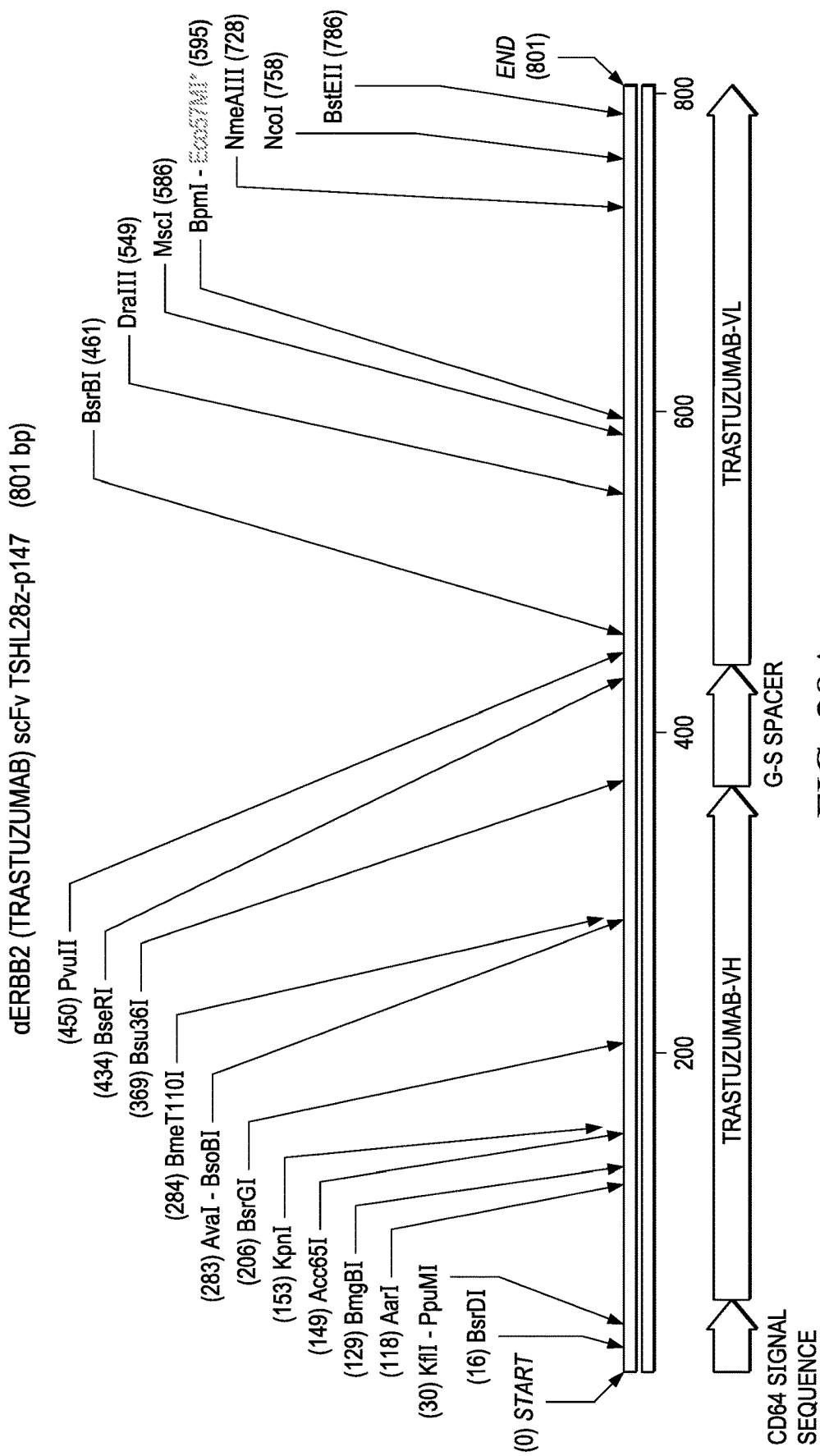
Figure 28B:
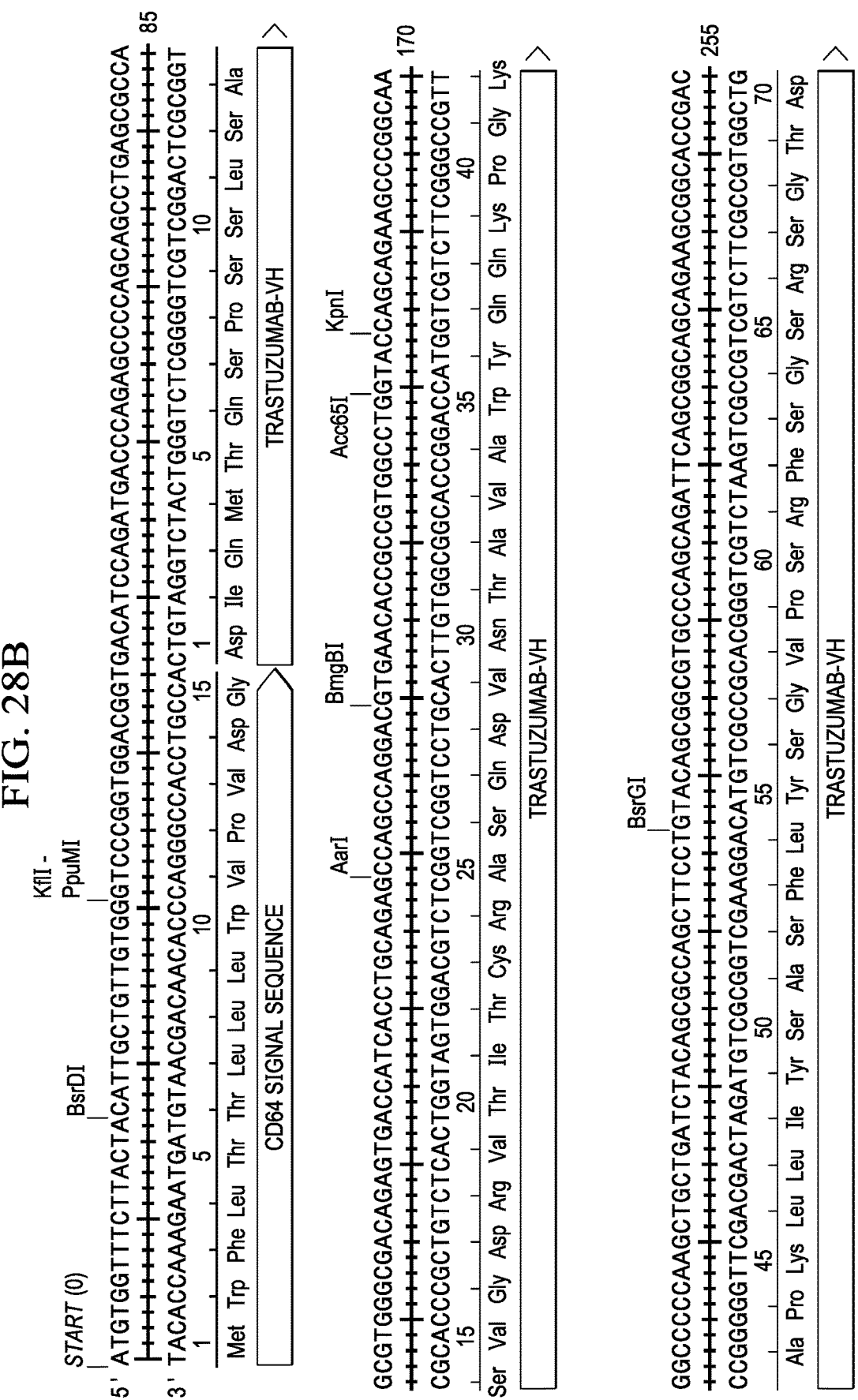
Figure 28B:
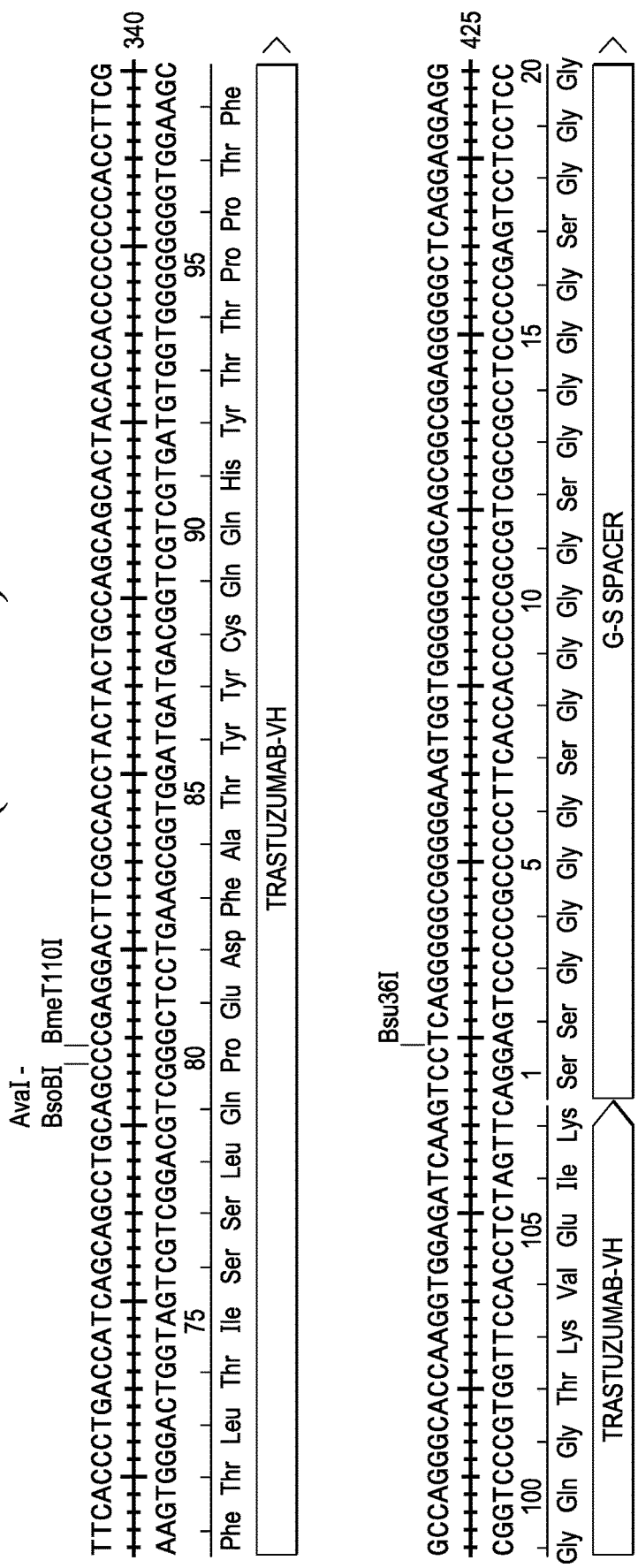
Figure 28B:
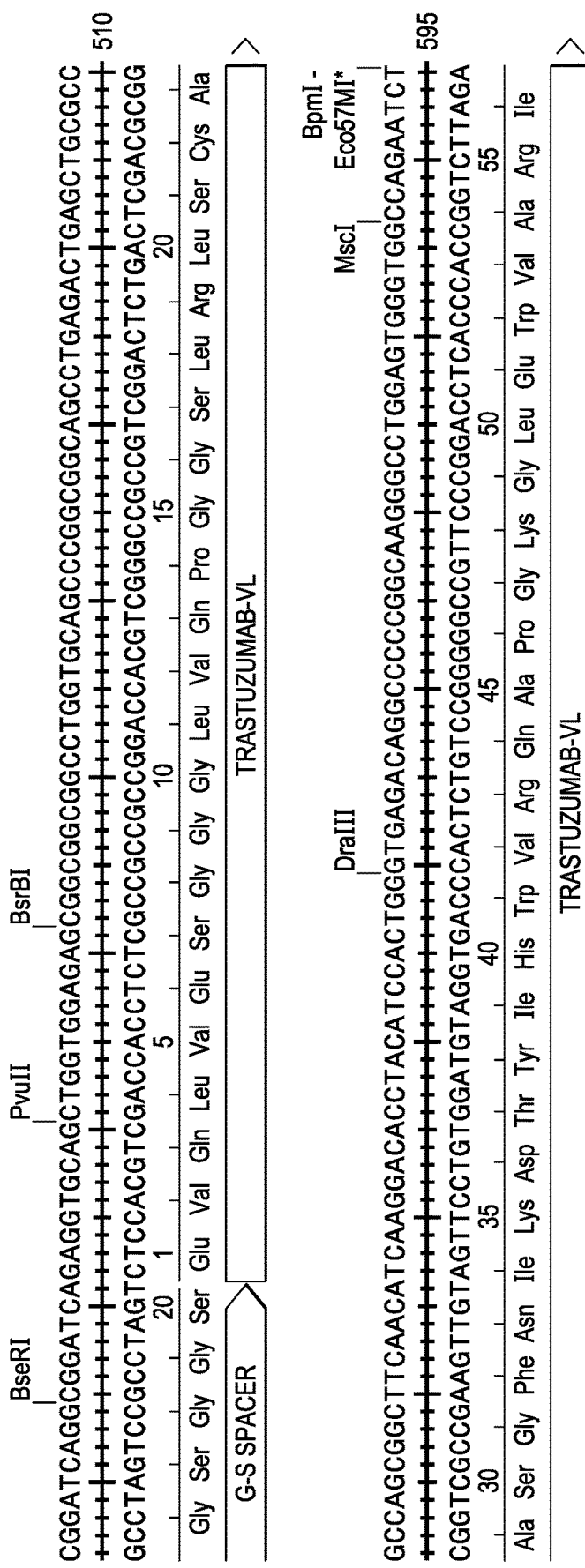
Figure 28B:
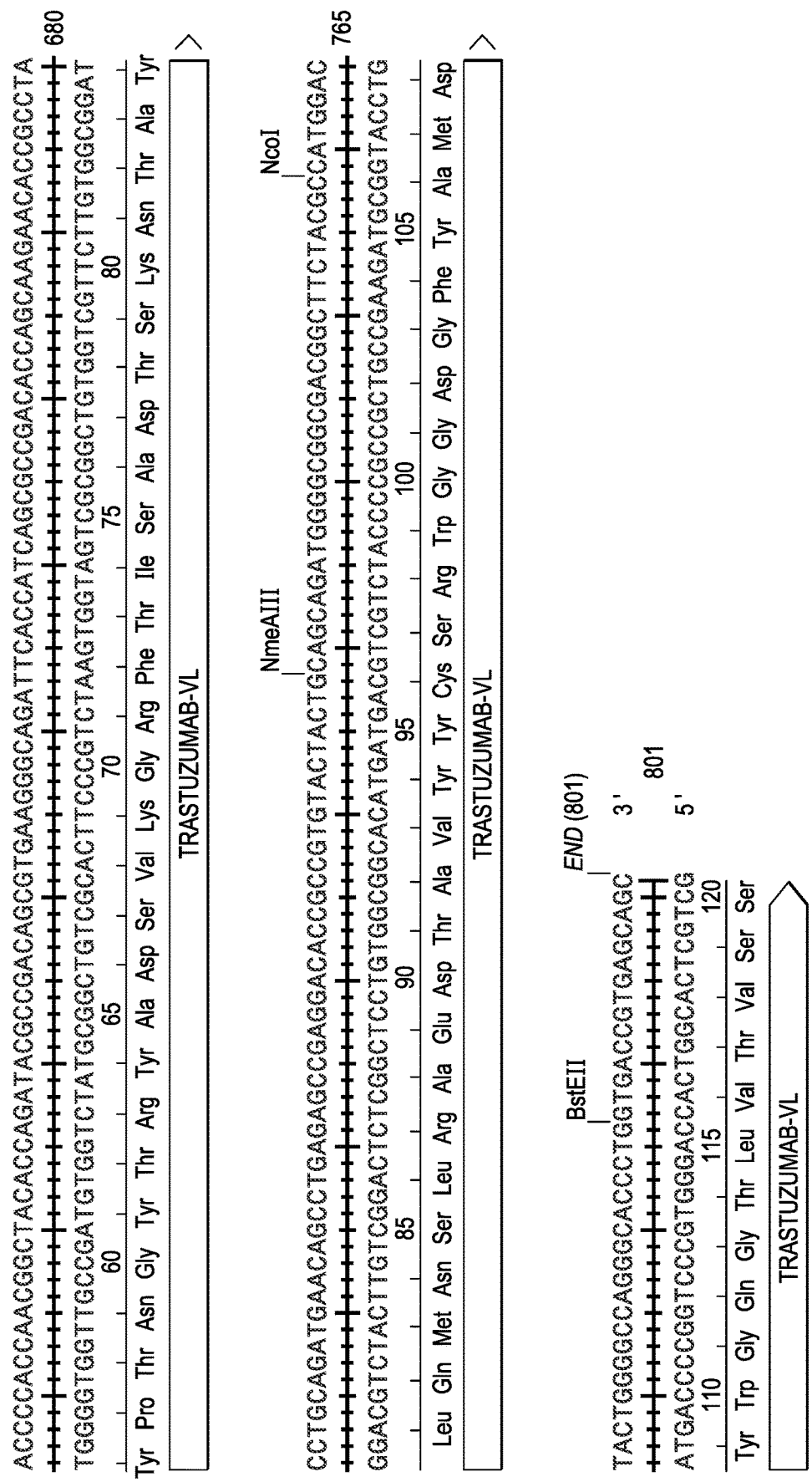

FIG. 28A shows the construction, orientation, and restriction sites of αERBB2 (Trastuzumab) ScFv TSHL28z-p147, corresponding to a CD64 signal sequence, Trastuzumab VH, G-S spacer, and Trastuzumab VL, respectively. FIG. 28B shows the sequence alignment, restriction sites, nucleotide sequence, and amino acid sequence of αERBB2 (FRP5) ScFv pXL011. The nucleotide sequence corresponds to, sequentially, SEQ ID NOs: 1, 19, 3, and 20, corresponding to CD64 signal sequence, Trastuzumab VH (also described as Trastuzumab heavy chain variable region), G-S spacer, and Trastuzumab VL (also described as Trastuzumab light chain variable region), respectively. The amino acid sequence corresponds to, sequentially, SEQ ID NOs: 38, 46, 39, and 47 corresponding to CD64, Trastuzumab VL, G-S spacer, and Trastuzumab VH, respectively.

DETAILED DESCRIPTION

An antigen binding domain (e.g., a single-chain Fv domain (scFv)) may be fused to a CAR scaffold, wherein said scFv gene comprises a VL domain linked to a VH domain via a flexible linker (e.g., $SG_{25}$ spacer), wherein the CAR scaffold encodes an extracellular domain, a transmembrane domain, and a cytoplasmic domain capable of activation of an immune cell (e.g., such as a lymphocyte cell or a cytotoxic cell). The resultant construct provides antibody or antibody-like specificity to the immune cell due to the antigen binding domain (e.g., an scFv), and the ability to activate the immune cell due to the gene segment comprising the cytoplasmic domain. These techniques may be implemented in T cells, mast cells, and NK cells as well as other suitable cell types.

According to present embodiments, CAR scaffolds and codon-optimized versions of CAR scaffolds are provided for expression of said constructs in immune or other cytotoxic cells, including NK cells, wherein the CAR scaffold is coupled to an antigen binding molecule. In some aspects, these CAR scaffolds are codon optimized for expression in immune or other cytotoxic cells for improved efficacy.

In some aspects, the CAR scaffold may comprise a CD28 domain coupled to a CD3ζ domain or the complete CD3ζ domain, which is joined to the scFv. For example, the sequence may comprise a leader sequence coupled to an scFv domain coupled to a CAR scaffold, wherein the scFv comprises: VL domain—spacer—VH domain or VH domain—spacer—VL domain.

In some aspects, the spacer may be a SG spacer (e.g., $SG_{25}$), however, the spacer may comprise any arrangement of amino acids providing sufficient flexibility within the scFv to allow the scFv to bind to its intended target.

In still other embodiments, the leader sequence may be a CD64 leader signal sequence. The CD64 signal sequence may comprise a signal peptide directing transport of the scFv-activation domain to the surface of the cell (e.g., immune or cytotoxic cell).

In some embodiments, the antigen binding molecule may be attached directly or through a linker to the activation region (e.g., this may be accomplished by recombinant expression of a nucleotide encoding the antigen binding molecule, an optional spacer, and a sequence encoding the activation domain). The recombinant expression system may be transfected into a host cell, wherein the fusion protein is expressed, constitutively or inductively.

The antigen binding domain may comprise a leader sequence, a variable region, a linker, and another variable region. The nucleotide sequences encoding these domains may be codon optimized for expression in a particular cell line, leading to higher expression levels of the CAR-based construct and improved efficacy over the non-codon optimized counterparts. It is noted that codon optimization does not alter the polypeptide sequence, but may change codon frequency to optimize expression in host organisms.

Any suitable antigen binding molecule may be attached to the tail activation domain. In some aspects, the antigen binding molecule may comprise a VH and VL domain. The VH and VL domain may be obtained from any suitable monoclonal antibody.

In some aspects, antigen binding molecules may include scFvs, antibodies, aptamers (short sequences of DNA, RNA, or Xeno nucleic acid (XNA) nucleotides), peptides, proteins, protein scaffolds, fusion proteins, or any other suitable molecule that may be engineered to specifically bind to target antigens. In some embodiments, protein scaffolds are related to or derived from peptide aptamers.

In other aspects, the nucleic acid sequence encoding the CD28 domain may comprise a nucleic acid encoding, partially or entirely, the CD28 ectodomain, the CD28 transmembrane domain, and the CD28 cytoplasmic domain.

In still other aspects, CD28 domain may be coupled to the CD3ζ activation domain. The nucleic acid sequence encoding the CD3ζ activation domain may encode at least two ITAMs, at least three ITAMs, etc.

Exemplary sequences are provided as follows. In one aspect, a CAR-19slh28ζ scaffold may comprise a tail end activation domain, such as SEQ ID NO.: 21. This sequence, SEQ ID NO.:21, comprises various domains, including an ectodomain (encoded by SEQ ID NO.: 27), a transmembrane domain (encoded by SEQ ID NO.: 28), and a cytoplasmic domain (encoded by SEQ ID NO.: 29).

In another aspect, the CAR scaffold contains a CD3ζ domain that is codon optimized, such as SEQ ID NO.: 23. This sequence, SEQ ID NO.: 23, also comprises various domains, including an ectodomain (encoded by SEQ ID NO.: 24), a transmembrane domain (encoded by SEQ ID NO.: 25), and a cytoplasmic domain (encoded by SEQ ID NO.: 26). Codon optimization may improve expression and thereby improve activity/efficacy of the CAR-based therapeutic composition in its target host cell (e.g., NK cells).

In other aspects, either of the CAR scaffolds (encoded by SEQ ID NO.: 5 or SEQ ID NO.: 22) may be attached to an antigen binding domain comprising a CD64 leader signal sequence (encoded by SEQ ID NO.: 1), a variable heavy (VH) or variable light (VL) chain (see figures for various VH and VL domains), and a GS spacer (encoded by SEQ ID NO.: 3, SEQ ID NO.: 10, SEQ ID NO.: 13, or SEQ ID NO.: 30), wherein the GS spacer joins the VH and VL domains.

In some aspects, sequences having 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over the full sequence or a specified region of the sequence (e.g., nucleotide sequences encoding VH and/or VL domains, CAR scaffold, etc.) are contemplated to fall within the scope of the embodiments provided herein.

Percent identity refers to a specified percentage of amino acid residues or nucleotides that are the same, when compared and aligned for maximum correspondence, over the entire length of the sequence or over a designated region of the sequence. A region may comprise at least 50 nucleotides, at least 100 nucleotides, at least 200 nucleotides, or more. A region may comprise at least 10 amino acids, at least 20 amino acids, at least 50 amino acids, or more.

As used herein, "antigen binding domain" refers to a molecule that specifically binds to an antigen on a cell surface (e.g., a malignant or cancer cell). The antigen binding domain includes but is not limited to single-chain Fvs (scFvs) and other antibody fragments as well as affimers, aptamers, peptides, proteins, small molecules, etc. Other antibody fragments include but are not limited to $F(ab')_2$, $Fab_2$, Fab', Fab, Fv, scFv-Fc, VhH, disulfide-linked Fvs (sdFv), etc. or any active fragment thereof, i.e. antibody fragments or other molecules that immunospecifically bind to an antigen (e.g., EGFR, IGFR-1, FRP5, PD-L1, etc.) or a variant thereof.

It is also understood that any one or more of the CDRs of any antibody fragment may be grafted onto the antigen binding domains described herein. The heavy chains and light chains have a general structure of relatively conserved framework regions (FR) joined by three hyper variable regions or CDRs (CDR1, CDR2, CDR3). The CDRs from the heavy and the light chains, which are aligned by the framework regions, enable binding to the antigen. One of skill in the art would be able to ascertain the CDRs based on known techniques.

The VH and VL domains may be derived from any suitable antibody, including but not limited to monoclonal antibodies, polyclonal antibodies, human antibodies, humanized antibodies, murine antibodies, conjugated antibodies (e.g., to a chemotherapeutic agent, to a radionuclide, to another protein, etc.), synthetic antibodies, bispecific antibodies, chimeric antibodies, single chain antibodies, antibody fragments produced by a Fab expression library, antibody fragments produced by mRNA display or phage display, and monovalent immunoglobulins (e.g., IgG).

Antibodies or fragments thereof may be generated using any suitable technique known in the art, including hybridoma technology, generation of phage displayed scFvs, generation of mRNA displayed scFvs or peptides, or isolation and screening of antisera, chemical synthesis, or through the use of recombinant expression systems.

Antibody fragments (e.g., scFvs) may be screened for binding to a suitable antigen according to techniques known in the art. Affinity maturation may be employed to improve the affinity of a scFv for its desired target. Therapeutic compositions that are administered to a patient include complexes comprising the antibody fragments (e.g., scFvs, etc.) described herein and are usually human or humanized.

Antibody fragments (e.g., scFvs) may be of any origin including but not limited to human, murine (e.g., mouse and rat), donkey, rabbit, goat, guinea pig, bird, camel, horse, or chicken. For therapeutic purposes, antibodies that are human or that have been humanized are preferred.

Any methodology known in the art for screening large combinatorial libraries to identify antibody fragments that bind to an antigen may be applied, including but not limited to phage display, yeast surface display, ribosome display, or mRNA display, or any combination thereof (see, Harlow et al., Antibodies: A Laboratory Manual, Cold Spring Harbor Laboratory Press, 2nd ed. 1988; Hammerling et al., Monoclonal Antibodies and T-Cell Hybridomas (1981) 563-681; WO 98/31700).

As used herein, "specifically binds" typically refers to non-covalent interactions between a target entity (e.g., a cell) and the antigen binding domain, and usually refers to the presence of such an interaction with a particular structural feature (e.g., such as an antigenic determinant on the cell surface) of the target entity with the antigen binding domain. As understood by one of skill in the art, an interaction is considered to be specific if it occurs in the presence of other alternative interactions.

As used herein, "composition" or "pharmaceutical composition" refers to a formulation comprising a therapeutic cell that is delivered to a patient comprising the CAR scaffold coupled to an antigen binding domain and may include one or more additional ingredients (e.g., buffers, excipients, stabilizers, diluents, emulsifiers, preservatives, etc.).

As used herein, and unless the context dictates otherwise, the term "linked to" or "linked with" is intended to include both direct coupling (in which two elements that are coupled to each other contact each other) and indirect coupling (in which at least one additional element is located between the two elements).

In other embodiments, assays may be performed to determine the effectiveness of the compositions. For such detection, an assay that includes the steps of culturing tumor cells under conditions suitable for growth and in a tumor microenvironment, contacting the cells with the CAR-based therapeutic as described herein, and then evaluating whether the CAR-based therapeutic reduces or inhibits the size of the mass may be used.

Components of the compositions disclosed herein can be organized in nearly any manner provided that functional activity for which the complex was designed is maintained. Additionally, the complexes described herein may include one or more tags, e.g., to facilitate modification, identification and/or purification of the components of the complex.

Linkers/Spacers

Linker sequences may be used to link the VH and VL domains of the scFvs, while maintaining desired functional activity of the VH and VL domains. As used herein and unless otherwise noted, the terms "linker sequence," "linker," "spacer," and "G-S spacer" are interchangeable and refer to sequences that connect the VH and VL domains. Where a particular linker sequence is contemplated, it will be associated with a corresponding SEQ ID NO. The linker sequence should allow effective positioning of the VH and VL domains to allow functional activity including binding to their respective antigenic targets.

The linker is preferably encoded by a nucleotide sequence resulting in a peptide that can effectively position the VH and VL domains or other antibody fragment for recognition of its intended target.

In some aspects, the linker sequence is flexible so as to not constrain the VH and VL domains in an undesirable conformation. In some embodiments, the linker comprises amino acids with small side chains, e.g., glycine, alanine and serine, to provide for flexibility. Preferably about 80 or 90 percent or greater of the linker sequence comprises such residues. Exemplary nucleotide sequences encoding linkers are provided in the specification (SEQ ID NO.: 3, SEQ ID NO.: 10, SEQ ID NO.: 13, and SEQ ID NO.: 30), although any suitable linker sequence may be used with the embodiments provided herein. Different linker sequences can be used including any number of flexible linker designs that have been used successfully to join antibody variable regions together, see Whitlow, M. et al., (1991) Methods: A Companion to Methods in Enzymology 2:97-105. Suitable linker sequences can be identified empirically, or determined by computer modeling techniques.

The compositions described herein may be administered in combination with any anti-cancer therapy, including but not limited to, chemotherapeutic agents (such methods are known to the skilled artisan and described in Remington's Pharmaceutical Sciences by E. W. Martin), surgery, radiation therapy, and/or chemotherapy.

Recombinant Expression Systems

Methods for introducing a polynucleotide into a host cell for expression are well known in the art, and include but are not limited to, integration of the foreign nucleotide sequence into the genome of the cell, vector-based methods wherein the foreign polynucleotide sequence is not integrated into the genome of the cell, and virus-mediated methods.

The sequence of interest (SOI), in this case, the nucleotide sequence encoding the antigen binding domain and the CAR scaffold may be recombinantly expressed in a host cell by inserting the nucleotide sequence into a suitable vector for expression in a mammalian cell and transfecting the vector into the host mammalian cell.

Vectors include DNA molecules into which a genetic insert has been introduced, allowing replication and expression of the insert in a host cell. Vectors include plasmids, viral vectors, cosmids, and artificial chromosomes. Expression vectors typically comprise an origin of replication (ORI), a multicloning site comprising various restriction sites into which an insert can be cloned, and one or more selectable markers (e.g., ampicillin or tetracycline, etc.) for selection. Additionally, the vector can include one or more transcription units, with a transcription unit including a promoter, a polyA signal sequence, and a transcription termination sequence. In some embodiments, the promoter is a mammalian promoter. In other embodiments, the promoter is a viral promoter. In still other embodiments, the promoter is associated with the gene of interest. Promoters can be constitutive or inducible. If induced, a chemical such as IPTG is added to the cell culture in order for the system to recombinantly express the desired protein.

Viral promoters include but are not limited to promoters from adenovirus (such as Adenovirus 2 or 5), cytomegalovirus (CMV), herpes simplex virus (thymidine kinase promoter), retroviral promoters (e.g., MoMLV or RSV LTR), ubiquitin C (UBC), EF1α, PGK, CAGG, and simian virus 40 (SV40). Many other viral promoters are suitable, and all such viral promoters are contemplated herein.

These techniques utilize, unless otherwise indicated, conventional techniques of cell biology, cell culture, molecular biology, virology, microbiology, recombinant DNA, and immunology, all of which are within the skill of an ordinary artisan. Such techniques are explained more fully in the literature. For a description of the functional components of expression vectors, including specific examples of promoters, enhancers, terminal signals, splicing signals, polyA signals, etc., reference is made to the following laboratory manuals that describe standard techniques of molecular biology, and are known by one of skill in the art (see, e.g., Green and Sambrook eds., Molecular Cloning: A Laboratory Manual, 4$^{th}$ edition, Cold Spring Harbor Laboratory, Cold Spring Harbor, N.Y., 2012; Ausubel et al., Current Protocols in Molecular Biology, 3$^{rd}$ ed. 1995; Bothwell et al. Methods for Cloning and Analysis of Eukaryotic Genes, Jones and Bartlett Publ. 1990; Wu, Grossman, Moldave eds. Recombinant DNA Methodology, Academic Press 1989; Adams ed., Cell Culture for Biochemists, Elsevier/North-Holland Biomedical Press, 1990; Butler ed., Mammalian Cell Biotechnology, IRL Press, 1991; Griffiths, et al., recombinant DNA technology in eukaryotes, in An Introduction to Genetic Analysis (2000), New York.

Examples of mammalian expression vectors include but are not limited to adenoviral vectors, adeno-associated vectors, baculovirus vectors, coronavirus, herpes simplex vectors, lentiviruses, pCMV series of plasmid vectors, pSV series of plasmid vectors, retroviral vectors, vaccinia, etc. Various vectors suitable for mammalian expression are derived from viruses, there are many such suitable vectors for expression in mammalian cells and all are contemplated herein.

In embodiments in which integration of the SOI into the host cell genome is desired, lentiviral expression systems may be selected. In embodiments in which integration into the host genome is not desirable, adenovirus expression systems or adeno-associated viruses expression systems may be selected.

Various methods are known in the art for transfection of mammalian expression vectors into host cells for expression, including viral transfection, lipofection, electroporation, calcium phosphate co-precipitation, rubidium chloride or polycation (such as DEAE-dextran)-mediated transfection, protoplast fusion and microinjection, see, e.g., Sambrook et al., for a description of such techniques. Preferably, the transfection method will provide an optimal transfection frequency and expression of the construct in the particular host cell line. Optimization may be performed using well-known techniques in the art.

In some embodiments, bacterial host cells are utilized to propagate mammalian expression vectors for preparation of DNA stocks for subcloning or for introduction into host cells. In other embodiments, bacterial host cells are utilized to produce large quantities of the protein encoded by the SOI (e.g., complexes). Bacterial host cells include but are not limited to *E. coli*. Yeast host cells include but are not limited to *Pichia pastoris*.

Suitable expression vectors for bacterial cells include but are not limited to bacterial expression vectors (e.g., *E. coli* expression vectors such as pGEX and pET series). In still other embodiments, suitable expression vectors include but are not limited to yeast expression vectors (e.g., pPIC series). In still other embodiments, cell-free systems containing the components needed for transcription and translation are provided.

In preferred embodiments, adenoviral expression systems are used. In such systems, an insert comprising a nucleotide encoding the SOI may be cloned into a shuttle vector. The shuttle vector and adenovirus backbone vector (e.g., commercially available systems such as RAPAd® Adenoviral Expression System from Cell Biolabs), are both linearized and are cotransfected into 293 cells to generate a viral stock solution in about 2-3 weeks. The viral stock solution may then be used to transfect target host cells with the nucleotide encoding the SOI(s).

In some embodiments, the transfected cells may be cultured under conditions to express the recombinant protein. In some embodiments, the cells may be subjected to suspension culture. In other embodiments, the cells may be subject to tissue culture. In still other embodiments, expression of the recombinant protein may be induced. In still other embodiments, expression of the recombinant protein may be constitutively expressed.

In some embodiments, the SOI is co-expressed with co-stimulatory molecules, such as cytokines. Immune stimulatory cytokines are added to promote or trigger an immune response. Cytokines include but are not limited to IL2, IL4, IL7, IL11, IL15, IL21, TNF-alpha, IFN-gamma, etc.

Use with Cytotoxic Cells

Genetically engineered cells may express the constructs provided herein (antigen binding domain coupled to CAR scaffold). These cells can be administered to the patient to recognize and eliminate tumorigenic and/or cancerous cells. Immune response assays may be performed to validate whether or not the engineered cells have activity against the tumor or cancer cell.

NK cells are deemed particularly suitable for use herein, especially where the NK cells are autologous NK cells, obtained from the same individual from which the tumor is obtained.

Alternatively, NK cells may also be grown from monoclonal sources, such as NK-92 or NK-92 derivatives, in which the cells are modified to have a reduced or abolished expression of at least one killer cell immunoglobulin-like receptor (KIR) to render such cells constitutively activated. Such modified cells may be prepared using protocols well known in the art.

Of course, it should also be appreciated that multiple different cell populations may be prepared that have different combinations or sub-combinations of Fc receptors and signaling moieties to so even further increase the anticipated therapeutic effect. For example, two different populations of NK cells may be administered where the first type of Fc receptor is CD16a and where the cell overexpresses Fcγ-signaling subunits, and where the second type of Fc receptor is CD32a and where the cell overexpresses Fcγ-signaling subunits. In another example, two different populations of cells may be administered where the first cell is an NK cell with expressing CD16a and overexpressing Fcγ-signaling subunits, and where the second cell is an CD8+ T-cell expressing CD16a and overexpressing Fcγ-signaling subunits. Regardless of the source of the cell, it is generally contemplated that the cell is a mammalian cell, and especially a human cell.

Additionally, and particularly where the cells are not obtained from the mammal that is to receive the subsequently modified cells, it is contemplated that the cells are rendered less immunogenic to the mammal (e.g., via HLA grafting or deletion of MHC complexes).

In yet another example, suitable NK cells for administration may be (or may be derived from) previously established therapeutic cell lines, which are well known in the art. For example, suitable cell lines include aNK cells, haNK cells, taNK cells, NK-92 cells (e.g., commercially available from Nantkwest, 9920 Jefferson Blvd. Culver City, CA 90232) or TALL 104 cells (e.g., commercially available from ATCC, CRL-11386, 10801 University Boulevard, Manassas, Va. 20110 USA).

In some cases, the administered cells may be allogeneic, and may be rejected by the recipient's immune system. Thus, in some embodiments, allogeneic cytotoxic cells are modified to be resistant to immunosuppressive agents (e.g., inactivating a gene that is a target for an immunosuppressive agent, e.g., a cyclophilin gene member, a CD52, a FKBP receptor, a glucocorticoid receptor, etc.) so that the cytotoxic cell is capable of functioning in the presence of the immune suppressive agent. The cytotoxic cells are administered in conjunction with immunosuppressive agents including but not limited to an immunosuppressive antimetabolite, a calcineurin inhibitor, a corticosteroid, a dihydrofolic acid reductase inhibitor, an inosine monophosphate dehydrogenase inhibitor, an interleukin-2 ot-chain blocker, or a rapamycin target.

NK cells express a variety of activating receptors, including NKG2D, Ly49 (some are activating, most are inhibitory), KIR (both activating and inhibitory), CD94-NKG2C, and CD94-NKG2E, and inhibitory receptors including Ly49 and KIR. These receptors recognize cellular stress ligands as well as MHC class I and related molecules. (see, Pegram et al., Immunology and Cell Biology (2011) 89:216-224)

Immune Activation

Once the CAR-based therapeutic (e.g., an antigen binding domain coupled to a CAR scaffold) binds to the antigen expressed by the cancer cell, the cytotoxic cell can trigger destruction of the cancer cell. While it is generally contemplated that all cytotoxic cells are deemed suitable for use herein, especially preferred cytotoxic cells include NK cells, activated NK cells, high affinity NK cells, CD8+ T-cells, and CD4+ T-cells that have been modified to recombinantly express the CAR-based therapeutic, any of which may be of different origins.

However, it should be appreciated that in other aspects, the cytotoxic cell may also be a macrophage, a monocyte, a neutrophil cell, a basophile, or eosinophil cell. Therefore, and viewed from a different perspective, the cells contemplated herein may effect cytotoxic action via phagocytosis, pore formation, induction of antibody-dependent cell-mediated cytotoxicity (ADCC), by triggering TNF or fas mediated killing pathways, etc.

Cytotoxic cells may release various types of cytotoxic granules (e.g., granulysin, perforin, granzymes) as part of this process. A variety of assays are available for monitoring cell-mediated cytotoxicity, including flow cytometric assays, e.g., based on presence of lytic granules such as perforin, granzymes, or production of TNF family members, e.g., TNF-α, FasL or TRAIL (Zaritskaya 2010, Clay, T. et al., Clin. Cancer Res. (2001) &:1127-1135).

In one embodiment, a bodily fluid is obtained, wherein the bodily fluid comprises cellular components, e.g., tumorigenic or cancer cells displaying an antigen to which the CAR scaffold expressing cells described herein bind to, and cytotoxic cells expressing the antigen binding moiety are contacted with the cells. Assays are then performed to detect immune responses, e.g., indicating that an ADCC response or an ADCP response has been triggered by the patient's own immune cells.

Assays for detecting an immune response are known in the art and are described herein. For example, assays for detecting such a response may detect a release of cytotoxic granules (e.g., granulysin, perforin, granzymes), or phagocytosis, or receptor-ligand mediated cytolysis (e.g., as mediated by the Fas/APO pathway). A variety of flow cytometric assays are available for monitoring cell-mediated cytotoxicity, e.g., based on presence of lytic granules such as perforin, granzymes, or production of TNF family members, e.g., TNF-α, FasL or TRAIL (Zaritskaya 2010, Clay, T. et al., Clin. Cancer Res. (2001) &:1127-1135).

In other embodiments, immune stimulatory cytokines are administered to a patient in combination with the host cell (expressing a CAR-based therapeutic (e.g., an antigen binding domain coupled to a CAR scaffold)) to promote or trigger an immune response. Cytokines include but are not limited to IL2, IL4, IL7, IL11, IL15, IL21, TNF-alpha, IFN-gamma, etc. In some embodiments, cytokines can reactivate exhausted T cells. In other cases, immune competent cells may be engineered to recombinantly express one or more cytokines.

Techniques to treat cancer include surgery, radiation therapy, chemotherapy, immunosuppressive reagents (e.g., azathioprine, cyclosporin, methotrexate, mycophenolate, etc.), immunotherapy, targeted therapy, hormone therapy, stem cell transplant, or other precision methods. Any of these techniques may be combined with embodiments of the present invention to treat cancer.

It is understood that present invention embodiments may be administered to a patient using appropriate formulations, indications, and dosing regimens suitable by government regulatory authorities such as the Food and Drug Administration (FDA) in the United States.

In some embodiments, a cytotoxic cell expressing a CAR-based therapeutic (e.g., an antigen binding domain coupled to a CAR scaffold) is administered to a patient as a pharmaceutical composition. In another embodiment, a method of treating cancer by administration of the cytotoxic cell to a subject is contemplated. In still another embodiment, a method inhibiting the proliferation or reducing the proliferation of a cell that is expressing the corresponding antigen (to which the antigen binding region binds to) on the surface of its cell by administration of the cytotoxic cell to a subject is contemplated.

In some embodiments, the cytotoxic cell expressing a CAR-based therapeutic (e.g., an antigen binding domain coupled to a CAR scaffold) reduces the amount (e.g., number of cells, size of mass, etc.) by at least 25%, at least 50%, at least 75%, at least 90%, at least 95%, or at least 99% in a subject with cancer associated with expression of the corresponding antigen on the surface of the cells relative to a negative control.

Examples of cancer that are treatable by the cytotoxic cells contemplated herein include any cancer expressing or overexpressing a cancer-associated antigen on its cell surface. Examples of cancer that can be treated with a cytotoxic cell expressing a CAR-based therapeutic (e.g., an antigen binding domain coupled to a CAR scaffold) include but are not limited to breast cancer, colon cancer, leukemia, lung cancer, melanoma, neuroblastoma, pancreatic cancer, pediatric intracranial ependymoma, and prostate cancer.

Pharmaceutical Compositions

Pharmaceutical compositions may comprise cytotoxic cells comprising an antigen binding domain coupled to or linked to a CAR scaffold, as described herein, in combination with one or more pharmaceutically or physiologically acceptable carriers, diluents or excipients. Additionally, pharmaceutical compositions may comprise one or more adjuvants (e.g., aluminum hydroxide), antioxidants, bacteriostats, buffers, carbohydrates, chelating agents such as EDTA or glutathione; coloring, flavoring and/or aromatic substances, emulsifiers, excipients, lubricants, pH buffering agents, preservatives, salts for influencing osmotic pressure, polypeptides (e.g., glycine), proteins, solubilizers, stabilizers, wetting agents, etc., which do not deleteriously react with the active compounds (e.g., antigen binding domain coupled to a CAR scaffold, etc.) or otherwise interfere with their activity. Buffers include but are not limited to neutral buffered saline, phosphate buffered saline, etc. Carbohydrates include but are not limited to dextrans, glucose, mannose, mannitol, sucrose, etc.

Pharmaceutical compositions may be formulated for a particular mode of administration. Modes of administration may include but are not limited to: intraarticular, intradermal, intranasal, intraperitoneal, intrathecally, intratumoral, intravenous, intraventricularly, subcutaneous, transdermal, transmucosal or topical routes.

In preferred embodiments, the cytotoxic cells are administered by intravenous infusion. Such formulations may be prepared according to standard techniques known by one of ordinary skill in the art. For example, a composition that is to be administered intravenously may have one or more ingredients (e.g., a diluent, a suspension buffer, saline or dextrose/water, other components such as cytokines, etc.) prior to infusion in the patient.

Many such techniques for formulating and administering pharmaceutical compositions are known in the art, e.g., U.S. Patent Application Publication No. 2014/0242025, and all such references are incorporated by reference herein in their entirety.

In some embodiments, the cytotoxic cells proliferate in vivo, thereby persisting in the patient for months or even years after administration to provide a sustained mechanism for inhibiting tumor growth or recurrence. In some aspects, the cytotoxic cells persist at least for three months, six months, nine months, twelve months, fifteen months, eighteen months, two years, three years, four years, or five years after administration of the cytotoxic cells to the patient.

Cytotoxic cells may be obtained from any of a variety of sources, (e.g., isolated from a human, from commercially available cytotoxic cells, from a cell repository, etc.). Procedures for ex vivo expansion of NK cells, T cells or other types of cytotoxic cells are known in the art (e.g., Smith et al., Clinical & Translational Immunology (2015) 4: e31). The examples presented herein are not intended to be limited to any particular method of ex vivo expansion of cytotoxic cells.

Pharmaceutical compositions comprising cytotoxic cells, as described herein, may be administered at a dosage of $10^4$ to $10^9$ cells/kg body weight, of $10^5$ to $10^6$ cells/kg body weight, or any integer values within these ranges. Cytotoxic cell compositions may be administered one time or serially (over the course of days or weeks or months) at these dosages. Infusion techniques for cytotoxic cells, such as T cells, are known in the art (see, e.g., Rosenberg et al., New Eng. J. of Med. 319: 1676, 1988).

In other embodiments, the pharmaceutical compositions are administered in a therapeutically effective amount, which is the amount effective for treating the specific indication. Administration may occur as a one-time dose or based on an interval. As used herein, "interval" indicates that the therapeutically effective amount is administered periodically (as distinguished from a one-time dose). The administration interval for a single individual need not occur at a fixed interval, but can vary over time. The term, "in combination with" or "co-administered" indicates that a composition can be administered shortly before, at or about the same time, or shortly after another composition.

It should be apparent to those skilled in the art that many more modifications besides those already described are possible without departing from the concepts herein. The present subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C and N, the text should be interpreted as requiring only one element from the group, not A plus N, or B plus N, etc.

EXAMPLES

Example 1. Generation of Antigen Binding Domain—CAR Scaffold

A variety of techniques are available for generation of the constructs provided herein. These constructs comprise an antibody fragment (e.g., a scFv, one or more CDRs, etc.) fused to a linker, which is fused to a CAR scaffold. Various protocols for generating these constructs are known to one of ordinary skill in the art.

In one embodiment, the nucleotide sequence encoding for a scFv may be obtained according to the techniques presented herein (e.g., phage display, mRNA display, from monoclonal antibodies, etc.). In some cases, the VH and VL domains may be known in the art, and linked together using known techniques to form an scFv. The nucleotide sequence corresponding to the scFv may be coupled to a CAR scaffold. Once the full nucleotide sequence is obtained, it may ligated into a suitable vector. Immune cells are then transfected with the vector, the construct is expressed, and the engineered cells are subjected to the assays disclosed herein.

CAR constructs direct NK cells to a particular target as NK cells without relying on HLA matching (unlike T cells) (see, e.g., Hermanson et al., Front Immunol (2015) 6:195; and Carlsten et al., Front Immunol (2015) 6:266). Various NK cell lines contemplated herein include but are not limited to aNK, HaNK, NK-92, NKG, NKL, NK-YS, TaNK, YT, and YTS cells.

Also contemplated herein is transfection with genes encoding for one or more cytokines, e.g., IL2, IL4, IL7, IL11, IL15, IL21, TNF-alpha, IFN-gamma. In some embodiments, IL-2 and/or IL-15 are transfected to promote in vivo expansion and persistence.

Cytotoxic cells may be genetically modified (i.e., transduced or transfected in vitro) with a vector encoding the constructs disclosed herein. The cytotoxic cell may be administered to a mammalian recipient to provide a therapeutic benefit, namely directing cytotoxic cells to destroy cells expressing the antigen that the antigen binding moiety binds to on their surface, e.g., cancer cells.

The mammalian recipient may be a human and the cytotoxic cell can be autologous with respect to the recipient. Alternatively, the cells can be allogeneic, syngeneic or xenogeneic with respect to the recipient. In some embodiments, allogeneic cells are administered with an immune suppressant.

Example 2. Cell Killing Assays

Killings assays are known in the art, e.g., at U.S. Pat. No. 7,741,465. For example, as provided in the '465 patent, the ability of the transfected cells to mediate specific target cell killing was determined by a $^{51}$Cr release assay.

For example, engineered cells may be transformed with constructs provided herein, and a level of cell lysis measured, based on a $^{51}$Cr release signal when compared to an untransfected control. Transfected cells will generally induce a significantly higher specific $^{51}$Cr release from human tumors or cancer cells than the corresponding control cells.

Example 3. Detection of an Immune Response

The ability of genetically engineered cells to elicit an immune response may be tested. A variety of assays for monitoring cellular immune responses in vivo and in vitro are available (see, e.g., Clay T. et al., Clin. Cancer Res. (2001) p 1127-1135).

In some embodiments, cytotoxic cells expressing the constructs provided herein (antigen binding domain coupled to a CAR scaffold) can be tested to determine whether an immune response is triggered, e.g., by detecting a release of cytotoxic granules, phagocytosis, or receptor-ligand mediated cytolysis, from lysed tumor cells.

Traditional assays for measuring cell lysis include addition of a radioisotope, e.g., $^{51}$Cr, to cell culture, which is trapped in the interior of living cells. The radioisotope is released upon cell lysis into the extracellular fluid, providing an indicator of the amount of lysis occurring.

Other assays exist in which levels of Granzyme B are measured. Granzyme B is secreted by activated cytotoxic T cells or NK cells. Granzyme B is released through exocytosis, and in conjunction with perforin, is able to enter target cells to help trigger cell death. Enzyme linked immunoassays (e.g., ELISpot, an ELISA sandwich assay) are known in the art for quantifying the amount of secreted Granzyme B. Essentially, cells are incubated in the presence of antibodies specific for Granzyme B. The cells are removed, and a second Granzyme B specific antibody is added with a detectable marker (e.g., biotin/alkaline phosphatase streptavidin complex). Based on the intensity of color formation, the amount of Granzyme B can be quantified (see, www.rnd-systems.com/products/human-granzyme-b-elispot-kit_e12906#product-details; Malyguine A. et al., Cells (2012) 1(2): 111-126).

What is claimed is:

1. An isolated nucleic acid sequence, optimized for expression in a mammalian cell, encoding a chimeric antigen receptor (CAR) polypeptide, wherein the CAR polypeptide comprises:
   an antigen binding domain coupled to a CAR scaffold, wherein the antigen binding domain comprises:
   a combination of SEQ ID NO: 7 or a nucleic acid sequence with 85% or greater identity thereof and SEQ ID NO: 9 or a nucleic acid sequence with 85% or greater identity thereof; or
   a combination of SEQ ID NO: 17 or a nucleic acid sequence with 85% or greater identity thereof and SEQ ID NO: 18 or a nucleic acid sequence with 85% or greater identity thereof; and
   wherein the CAR scaffold comprises a CD3ζ domain, wherein the CD3ζ domain comprises one or more of:
   the nucleic acid sequence of SEQ ID NO: 24 or a nucleic acid sequence with 85% or greater identity thereof that encodes an ectodomain;
   the nucleic acid sequence of SEQ ID NO: 25 or a nucleic acid sequence with 85% or greater identity thereof that encodes a transmembrane domain; and
   the nucleic acid sequence of SEQ ID NO: 26 or a nucleic acid sequence with 85% or greater identity thereof that encodes a cytoplasmic domain.

2. The isolated nucleic acid sequence of claim 1, wherein the CAR scaffold comprises the CD3ζ domain, and the nucleic acid sequence comprises:
   the nucleic acid sequence of SEQ ID NO: 24 or a nucleic acid sequence with 85% or greater identity thereof that encodes an ectodomain;
   the nucleic acid sequence of SEQ ID NO: 25 or a nucleic acid sequence with 85% or greater identity thereof that encodes a transmembrane domain; and
   the nucleic acid sequence of SEQ ID NO: 26 or a nucleic acid sequence with 85% or greater identity thereof that encodes a cytoplasmic domain.

3. The isolated nucleic acid sequence of claim 1, wherein the CAR scaffold comprises a nucleic acid sequence corresponding to SEQ ID NO: 22 encoding a complete CD3ζ domain.

4. The isolated nucleic acid sequence of claim 1, wherein the nucleic acid sequence encodes an scFv.

5. The isolated nucleic acid sequence of claim 4, wherein the nucleic acid sequence encoding the scFv is human, humanized, synthetic or chimeric.

6. The isolated nucleic acid sequence of claim 4, wherein the nucleic acid sequence additionally comprises a nucleic acid sequence comprising SEQ ID NO: 1.

7. The isolated nucleic acid sequence of claim 1, wherein the nucleic acid sequence encodes a linker comprising glycine and serine amino acids.

8. The isolated nucleic acid sequence of claim 7, wherein the linker comprises about 15 to 25 amino acids.

9. The isolated nucleic acid sequence of claim 1, wherein the antigen binding domain comprises a scFv including a linker, and wherein the linker is encoded by a nucleic acid sequence selected from the group consisting of:
   SEQ ID NO: 3;
   SEQ ID NO: 8;
   SEQ ID NO: 11; and
   SEQ ID NO: 30.

10. A vector comprising the isolated nucleic acid sequence of claim 1.

11. An immune cell comprising the vector of claim 10.

12. An NK cell comprising the vector of claim 10.

13. An immune cell comprising the isolated nucleic acid sequence of claim 1.

14. An NK cell comprising the isolated nucleic acid sequence of claim 1.

15. A method for making an immune cell comprising transducing or transfecting the immune cell with an isolated nucleic acid sequence encoding the chimeric antigen receptor (CAR) polypeptide of claim 1.

16. A method for treating a cancer in a subject comprising administering in an effective amount an immune cell expressing the isolated nucleic acid encoding the chimeric antigen receptor (CAR) polypeptide of claim 1 to the subject, thereby causing selective depletion of the cancer cells.

17. A chimeric antigen receptor (CAR) polypeptide comprising:
   a signal sequence,
   an antigen binding domain; and
   a CAR scaffold,
   wherein the antigen binding domain comprises
   an amino acid sequence comprising the sequence of SEQ ID NO: 33 or an amino acid sequence with 85% or greater identity thereof and an amino acid sequence comprising the sequence of SEQ ID NO: 35 or an amino acid sequence with 85% or greater identity thereof; and
   wherein the CAR scaffold comprises SEQ ID NO: 23 or an amino acid sequence with 85% or greater identity thereof.

18. A chimeric antigen receptor (CAR) polypeptide comprising:
   a signal sequence;
   an antigen binding domain; and
   a CAR scaffold,
   wherein the antigen binding domain comprises
   an amino acid sequence comprising the sequence of SEQ ID NO: 33 or an amino acid sequence with 85% or greater identity thereof and an amino acid sequence comprising the sequence of SEQ ID NO: 35 or an amino acid sequence with 85% or greater identity thereof;
   and the CAR scaffold comprises an amino acid sequence corresponding to SEQ ID NO: 21.

19. An isolated nucleic acid sequence, optimized for expression in a mammalian cell, encoding a chimeric antigen receptor (CAR) polypeptide, wherein the CAR polypeptide comprises an antigen binding domain coupled to a CAR scaffold,
   wherein the antigen binding domain is encoded by a nucleic acid sequence selected from the group consisting of:
   (2) SEQ ID NO: 7 or a nucleic acid sequence with 85% or greater identity thereof and SEQ ID NO: 9 or a nucleic acid sequence with 85% or greater identity thereof; and
   (3) SEQ ID NO: 17 or a nucleic acid sequence with 85% or greater identity thereof and SEQ ID NO: 18 or a nucleic acid sequence with 85% or greater identity thereof; and
   wherein the CAR scaffold is a CD28 domain coupled to a CD37 domain comprising two immunoreceptor tyrosine-based activation motifs (ITAMs).

20. The isolated nucleic acid sequence of claim 19, wherein the CAR scaffold comprises the CD28 domain coupled to the CD3ζ domain, and the nucleic acid sequence comprises one or more of:

the nucleic acid sequence of SEQ ID NO: 27 or a nucleic acid sequence with 85% identity thereof that encodes an ectodomain;

the nucleic acid sequence of SEQ ID NO: 28 or a nucleic acid sequence with 85% identity thereof that encodes a transmembrane domain; and the nucleic acid sequence of SEQ ID NO: 29 or a nucleic acid sequence with 85% identity thereof that encodes a cytoplasmic domain.

21. The isolated nucleic acid sequence of claim 20, wherein the nucleic acid sequence encodes an scFv.

22. The isolated nucleic acid sequence of claim 21, wherein the nucleic acid sequence encoding the scFv is human, humanized, synthetic or chimeric.

23. The isolated nucleic acid sequence of claim 21, wherein the nucleic acid sequence encodes a linker comprising glycine and serine amino acids.

24. The isolated nucleic acid sequence of claim 23, wherein the linker comprises about 15 to 25 amino acids.

25. The isolated nucleic acid sequence of claim 19, wherein the CAR scaffold comprises a nucleic acid sequence corresponding to SEQ ID NO: 5.

26. The isolated nucleic acid sequence of claim 25, wherein the nucleic acid sequence additionally comprises a nucleic acid sequence comprising SEQ ID NO: 1.

27. The isolated nucleic acid sequence of claim 19, wherein the antigen binding domain comprises a scFv including a linker, and wherein the linker is encoded by a nucleic acid sequence selected from the group consisting of:

SEQ ID NO: 3;
SEQ ID NO: 8;
SEQ ID NO: 11; and
SEQ ID NO: 30.

* * * * *

SEQUENCE LISTING

<160> NUMBER OF SEQ ID NOS: 47

<210> SEQ ID NO 1
<211> LENGTH: 45
<212> TYPE: DNA
<213> ORGANISM: Artificial Sequence

```
<220> FEATURE:
<223> OTHER INFORMATION: CD64 leader signal sequence

<400> SEQUENCE: 1
atgtggtttc ttactacatt gctgttgtgg gtcccggtgg acggt                    45

<210> SEQ ID NO 2
<211> LENGTH: 321
<212> TYPE: DNA
<213> ORGANISM: Artificial Sequence
<220> FEATURE:
<223> OTHER INFORMATION: FMC63 light chain variable region

<400> SEQUENCE: 2
gacatccaga tgacacagac tacatcctcc ctgtctgcct ctctgggaga cagagtcacc     60
atcagttgca gggcaagtca ggacattagt aaatatttaa attggtatca gcagaaacca    120
gatggaactg ttaaactcct gatctaccat acatcaagat tacactcagg agtcccatca    180
aggttcagtg gcagtgggtc tggaacagat tattctctca ccattagcaa cctggagcaa    240
gaagatattg ccacttactt ttgccaacag ggtaatacgc ttccgtacac gttcggaggg    300
gggactaagt tggaaataac a                                              321

<210> SEQ ID NO 3
<211> LENGTH: 75
<212> TYPE: DNA
<213> ORGANISM: Artificial Sequence
<220> FEATURE:
<223> OTHER INFORMATION: G-S spacer

<400> SEQUENCE: 3
tcctcagggg gcggggggaag tggtgggggc ggcagcggcg gagggggctc aggaggaggc    60
ggatcaggcg gatca                                                     75

<210> SEQ ID NO 4
<211> LENGTH: 360
<212> TYPE: DNA
<213> ORGANISM: Artificial Sequence
<220> FEATURE:
<223> OTHER INFORMATION: FMC63 heavy chain variable region

<400> SEQUENCE: 4
gaggtgaaac tgcaggagtc aggacctggc ctggtggcgc cctcacagag cctgtccgtc     60
acatgcactg tctcaggggt ctcattaccc gactatggtg taagctggat tcgccagcct    120
ccacgaaagg gtctggagtg gctgggagta atatgggta gtgaaaccac atactataat    180
tcagctctca aatccagact gaccatcatc aaggacaact ccaagagcca agttttctta    240
aaaatgaaca gtctgcaaac tgatgacaca gccatttact actgtgccaa acattattac    300
tacggtggta gctatgctat ggactactgg ggtcaaggaa cctcagtcac cgtctcctca    360

<210> SEQ ID NO 5
<211> LENGTH: 663
<212> TYPE: DNA
<213> ORGANISM: Artificial Sequence
<220> FEATURE:
<223> OTHER INFORMATION: Ectodomain, transmembrane and signaling domains

<400> SEQUENCE: 5
attgaagtta tgtatcctcc tcctacctta gacaatgaga gagcaatgg aaccattatc     60 catgtgaaag ggaaacacct ttgtccaagt ccccctattt ccggaccttc taagccctt    120
```

```
tgggtgctgg tggtggttgg tggagtcctg gcttgctata gcttgctagt aacagtggcc      180
tttattattt tctgggtgag gagtaagagg agcaggctcc tgcacagtga ctacatgaac      240
atgactcccc gccgcccgg gcccacccgc aagcattacc agccctatgc ccaccacgc        300 gacttcgcag cctatcgctc cagagtgaag ttcagcagga gcgcagacgc cccgcgtac       360 cagcagggcc agaaccagct ctataacgag ctcaatctag gacgaagaga ggagtacgat      420
gttttggaca gagacgtgg ccgggaccct gagatggggg gaaagccgca gagaaggaag        480
aaccctcagg aaggcctgta caatgaactg cagaaagata gatggcgga ggcctacagt       540 gagattggga tgaaaggcga gcgccggagg ggcaagggc acgatggcct ttaccagggt        600
ctcagtacag ccaccaagga cacctacgac gcccttcaca tgcaggccct gccccctcgc      660
taa                                                                    663
```

```
<210> SEQ ID NO 6
<211> LENGTH: 267
<212> TYPE: PRT
<213> ORGANISM: Artificial Sequence
<220> FEATURE:
<223> OTHER INFORMATION: CD19-SPScFvFMC63

<400> SEQUENCE: 6

Met Trp Phe Leu Thr Thr Leu Leu Trp Val Pro Val Asp Gly Asp
1               5                   10                  15

Ile Gln Met Thr Gln Thr Ser Ser Leu Ser Ala Ser Leu Gly Asp
                20                  25                  30

Arg Val Thr Ile Ser Cys Arg Ala Ser Gln Asp Ile Ser Lys Tyr Leu
            35                  40                  45

Asn Trp Tyr Gln Gln Lys Pro Asp Gly Thr Val Lys Leu Leu Ile Tyr
        50                  55                  60

His Thr Ser Arg Leu His Ser Gly Val Pro Ser Arg Phe Ser Gly Ser
65                  70                  75                  80

Gly Ser Gly Thr Asp Tyr Ser Leu Thr Ile Ser Asn Leu Glu Gln Glu
                85                  90                  95

Asp Ile Ala Thr Tyr Phe Cys Gln Gln Gly Asn Thr Leu Pro Tyr Thr
            100                 105                 110

Phe Gly Gly Gly Thr Lys Leu Glu Ile Thr Ser Ser Gly Gly Gly Gly
        115                 120                 125

Ser Gly Gly Gly Gly Ser Gly Gly Gly Ser Gly Gly Gly Gly Ser
    130                 135                 140

Gly Gly Ser Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser
```

<210> SEQ ID NO 7
<211> LENGTH: 327
<212> TYPE: DNA
<213> ORGANISM: Artificial Sequence
<220> FEATURE:
<223> OTHER INFORMATION: SHIE2 light chain variable region

<400> SEQUENCE: 7

```
cagtctgccc tgactcagcc tgcctccgtg tctgggtctc ttggacagtc agtcaccatc      60
tcctgcactg gaagcagcag tgatgttggg agttataacc ttgtctcctg gtaccaacag     120
cacccaggca aagcccccaa tctcatgatt tatgatgtca gtaagcggtc aggggtttct     180
aatcgcttct ctggctccaa gtctggcaac acggcctccc tgaccatctc tgggctccag     240
gctgaggacg aggctgatta ttactgcagc tcatatacag catcagcac cgtggtattc      300
ggcggaggga ccaagctgac cgtcctg                                         327
```

<210> SEQ ID NO 8
<211> LENGTH: 60
<212> TYPE: DNA
<213> ORGANISM: Artificial Sequence
<220> FEATURE:
<223> OTHER INFORMATION: linker

<400> SEQUENCE: 8

```
ggcggcggag gaagcggagg cggaggatct gggggcggag gctctggcgg aggggggatct    60
```

<210> SEQ ID NO 9
<211> LENGTH: 357
<212> TYPE: DNA
<213> ORGANISM: Artificial Sequence
<220> FEATURE:
<223> OTHER INFORMATION: SHIE2 heavy chain variable region

<400> SEQUENCE: 9

```
gaggtgcagc tggtggagtc tggggctgag gtgaagaagc ctgggtcctc ggtgaaggtc      60
tcctgcaagg cttctggagg cacCttcagc agctatgcta tcagctgggt gcgacaggcc     120
cctggacaag gcttgagtg gatgggaggg atcatcccta tctttggtac agcaaactac      180
gcacagaagt tccagggcag agtcacgatt accgcggacg aatccacgag cacagcctac     240
atggagctga gcagcctgag atctgaggac acggccgtgt attactgtgc gagagccccg     300
tactactact actacatgga cgtctggggc caagggacca cggtcaccgt gagctca        357
```

<210> SEQ ID NO 10
<211> LENGTH: 327
<212> TYPE: DNA
<213> ORGANISM: Artificial Sequence
<220> FEATURE:
<223> OTHER INFORMATION: RBSC6 light chain variable region

<400> SEQUENCE: 10

```
aacatccaga tgacccagtc tccatcttct gtgtctgcat ctgtaggaga cagagtcacc      60
atcacttgtc gggcgagtca ggatattagc gctggttag cctggtatca gcagaaacca     120
gggaaagccc ctaaactcct gatctatgct gcatccagtt tgcaaagtgg ggtcccatcg     180
aggttcagcg gcagtggatc tgggacagat ttcgctctca ctatcagcag cctgcagcct    240
gaagattttg caacttacta ttgtcaacag gctgacagtg tttctcgat caccttcggc     300
caagggacac gactggagat taaaggc                                         327
```

<210> SEQ ID NO 11
<211> LENGTH: 57
<212> TYPE: DNA
<213> ORGANISM: Artificial Sequence
<220> FEATURE:
<223> OTHER INFORMATION: G-S linker

<400> SEQUENCE: 11
ggcggaggaa gcggaggcgg aggatctggg ggcggaggct ctggcggagg gggatct    57

<210> SEQ ID NO 12
<211> LENGTH: 354
<212> TYPE: DNA
<213> ORGANISM: Artificial Sequence
<220> FEATURE:
<223> OTHER INFORMATION: RBSC6 heavy chain variable region

<400> SEQUENCE: 12
gaggtgcagc tggtgcagtc tgggggaggc ttggtacagc ctgggggggtc cctgagactc    60 tcctgtgcag cctctggatt caccttcagt agctatagca tgaactgggt ccgccaggct    120
ccagggaagg gctggagtg gtttcatac attagtagta gtagtagtac catacagtac    180
gcagactctg tgaagggccg attcaccatc tccagagaca atgccaagaa ctcactgtat    240
ctgcaaatga acagcctgag agacgaggac acggctgtgt attactgtgc gagagggac    300 tactactacg gtatggacgt ctggggccaa gggaccacgg tcaccgtgag ctca    354

<210> SEQ ID NO 13
<211> LENGTH: 336
<212> TYPE: DNA
<213> ORGANISM: Artificial Sequence
<220> FEATURE:
<223> OTHER INFORMATION: Ganitumab light chain variable region

<400> SEQUENCE: 13
gatgttgtaa tgacgcagtc acccctgtca ctcccggtca cacccggaga accagcgtca    60
attagctgcc gatctagcca aagttttgctt cattccaatg gttacaatta tctcgactgg    120
tacttgcaga aacccggcca atcccctcag ctgctcatct accttgggtc taatagggca    180
tctggggttc ccgataggtt ctctggctcc gggagcggca ccgactttac gttgaaaatc    240
tctagggttg aggcggaaga cgtaggcgtt tactattgca tgcaggggac ccactggccg    300
ctgaccttcg gccagggcac caaggttgaa ataaaa    336

<210> SEQ ID NO 14
<211> LENGTH: 366
<212> TYPE: DNA
<213> ORGANISM: Artificial Sequence
<220> FEATURE:
<223> OTHER INFORMATION: Ganitumab heavy chain variable region

<400> SEQUENCE: 14
ggcggatcac aggtacagct ccaggaatca ggacccggtt tggttaagcc ctccgggacc    60
ctttccctca cgtgtgcagt ctcaggtggg tcaattagtt cttccaattg gtggtcttgg    120
gtgcggcaac cacctggtaa aggtctcgag tggataggg aaatttatca agtggctcc    180 accaattata accctcact caagtccagg ttacgatat ctgtggacaa agtaaaaac    240 caattctccc tcaaacttag tagtgtaaca gcggcagaca ccgcggtgta ctactgcgca    300
cggtggacag gccgaactga tgcctttgac atttggggac agggaactat ggtgactgtg    360
tcatcc                                                                    366

<210> SEQ ID NO 15
<211> LENGTH: 321
<212> TYPE: DNA
<213> ORGANISM: Artificial Sequence
<220> FEATURE:
<223> OTHER INFORMATION: Cetuximab light chain variable region

<400> SEQUENCE: 15
gatattcttc ttactcaatc tcccgttatt ttgtcagtat ccccaggtga gcgagtcagc    60
ttctcttgtc gagcgtcaca atccattggc accaacatac attggtacca acagcgcacc   120
aacgggtctc cccggctctt gattaagtac gcatcagaaa gtatttctgg gatacccagt   180
aggttctcag ggagcgggag tggcactgac tttaccctgt ccataaacag cgttgagtct   240
gaggacatcg cggactacta ttgtcagcag aacaacaatt ggccgaccac gtttggtgcg   300
ggaacaaaac ttgaactcaa a                                              321

<210> SEQ ID NO 16
<211> LENGTH: 357
<212> TYPE: DNA
<213> ORGANISM: Artificial Sequence
<220> FEATURE:
<223> OTHER INFORMATION: Cetuximab heavy chain variable region

<400> SEQUENCE: 16
caggtgcagc tcaaacagtc aggacctggc ctcgttcagc caagccaatc actgagtata    60
acgtgcacgg tgagcggctt tagcctgaca aactatggtg tccactgggt ccgccaatct   120
cctggaaaag gcttggagtg gctcggtgtt atctggtccg gtggtaacac agactacaac   180
acgccattca ccagtcgcct tagtattaac aaggacaact ccaagtctca ggttttcttt   240
aaaatgaact ctctgcagtc taatgatacc gcaatttact actgtgcgag gcactcacg    300 tactatgact atgagttcgc gtattgggc caagggactc tcgttactgt ctcagcg       357

<210> SEQ ID NO 17
<211> LENGTH: 364
<212> TYPE: DNA
<213> ORGANISM: Artificial Sequence
<220> FEATURE:
<223> OTHER INFORMATION: FRP5 heavy chain variable region

<400> SEQUENCE: 17
ggacggtcag gtacaactgc agcagtctgg acctgaactg aagaagcctg gagagacagt    60
caagatctcc tgcaaggcct ctgggtatcc tttcacaaac tatggaatga actgggtgaa   120
gcaggctcca ggacagggtt taaagtggat gggctggatt aacacctcca ctggagagtc   180
aacatttgct gatgacttca agggacggtt tgacttctct ttggaaacct ctgccaacac   240
tgcctatttg cagatcaaca acctcaaaag tgaagacatg gctacatatt tctgtgcaag   300
atgggaggtt taccacggct acgttcctta ctggggccaa gggaccacgg tcaccgtttc   360
ctct                                                                  364

<210> SEQ ID NO 18
<211> LENGTH: 318
<212> TYPE: DNA
<213> ORGANISM: Artificial Sequence
<220> FEATURE:
<223> OTHER INFORMATION: FRP5 light chain variable region

<400> SEQUENCE: 18

```
gacatccagc tgacccagtc tcacaaattc ctgtccactt cagtaggaga cagggtcagc      60
atcacctgca aggccagtca ggatgtgtat aatgctgttg cctggtatca acagaaacca     120
ggacaatctc ctaaacttct gatttactcg gcatcctccc ggtacactgg agtcccttct     180
cgcttcactg gcagtggctc tgggccggat ttcactttca ccatcagcag tgtgcaggct     240
gaagacctgg cagtttattt ctgtcagcaa cattttcgta ctccattcac gttcggctcg     300
gggacaaaat tggagatc                                                   318

<210> SEQ ID NO 19
<211> LENGTH: 328
<212> TYPE: DNA
<213> ORGANISM: Artificial Sequence
<220> FEATURE:
<223> OTHER INFORMATION: Trastuzumab heavy chain variable region

<400> SEQUENCE: 19
ggacggtgac atccagatga cccagagccc cagcagcctg agcgccagcg tgggcgacag      60
agtgaccatc acctgcagag ccagccagga cgtgaacacc gccgtggcct ggtaccagca     120
gaagcccggc aaggcccca agctgctgat ctacagcgcc agcttcctgt acagcggcgt      180
gcccagcaga ttcagcggca gcagaagcgg caccgacttc accctgacca tcagcagcct     240
gcagcccgag gacttcgcca cctactactg ccagcagcac tacaccaccc ccccccacctt    300 cggccagggc accaaggtgg agatcaag                                         328

<210> SEQ ID NO 20
<211> LENGTH: 360
<212> TYPE: DNA
<213> ORGANISM: Artificial Sequence
<220> FEATURE:
<223> OTHER INFORMATION: Trastuzumab light chain variable region

<400> SEQUENCE: 20
gaggtgcagc tggtggagag cggcggcggc ctggtgcagc ccggcggcag cctgagactg      60
agctgcgccg ccagcggctt caacatcaag gacacctaca tccactgggt gagacaggcc     120
cccggcaagg gcctggagtg ggtggccaga atctacccca ccaacggcta caccagatac     180
gccgacagcg tgaagggcag attcaccatc agcgccgaca ccagcaagaa caccgcctac     240
ctgcagatga cagcctgag agccgaggac accgccgtgt actactgcag cagatggggc     300
ggcgacggct ctacgccat ggactactgg ggccagggca ccctggtgac cgtgagcagc     360

<210> SEQ ID NO 21
<211> LENGTH: 220
<212> TYPE: PRT
<213> ORGANISM: Artificial sequence
<220> FEATURE:
<223> OTHER INFORMATION: CAR-CD19-CD28/CD3zeta (CAR-19slh28zeta)

<400> SEQUENCE: 21

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60
```

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser Arg Val Lys Phe Ser
            100                 105                 110

Arg Ser Ala Asp Ala Pro Ala Tyr Gln Gln Gly Gln Asn Gln Leu Tyr
        115                 120                 125

Asn Glu Leu Asn Leu Gly Arg Arg Glu Glu Tyr Asp Val Leu Asp Lys
    130                 135                 140

Arg Arg Gly Arg Asp Pro Glu Met Gly Gly Lys Pro Gln Arg Arg Lys
145                 150                 155                 160

Asn Pro Gln Glu Gly Leu Tyr Asn Glu Leu Gln Lys Asp Lys Met Ala
                165                 170                 175

Glu Ala Tyr Ser Glu Ile Gly Met Lys Gly Glu Arg Arg Arg Gly Lys
            180                 185                 190

Gly His Asp Gly Leu Tyr Gln Gly Leu Ser Thr Ala Thr Lys Asp Thr
        195                 200                 205

Tyr Asp Ala Leu His Met Gln Ala Leu Pro Pro Arg
    210                 215                 220

<210> SEQ ID NO 22
<211> LENGTH: 453
<212> TYPE: DNA
<213> ORGANISM: Artificial Sequence
<220> FEATURE:
<223> OTHER INFORMATION: CD3zeta

<400> SEQUENCE: 22
cagctgccca tcaccgaggc tcaatccttt gggctgcttg atcctaagtt gtgttatctt    60
cttgacggca tcctgtttat atacggtgtc attttgacag ctctctttct ccgagtcaag   120
ttcagtcggt ctgcagatgc tccagcatac agcaaggcc aaaatcagct gtataacgag    180
ttgaaccttg gcgacgagaa agaatacgac gtgcttgaca acgcagaggg tcgggaccct   240
gaaatggggg gtaagccgca aaggcggaag aatccacaag agggtctgta taatgaattg   300
caaaaagaca agatggctga ggcatactca gagattggaa tgaaagggga agacggagg   360 ggaaagggcc acgatggact gtaccaaggg ctgagcaccg caactaaaga tacatatgat   420
gctctgcaca tgcaggccct gccacctaga taa                                 453

<210> SEQ ID NO 23
<211> LENGTH: 150
<212> TYPE: PRT
<213> ORGANISM: Artificial Sequence
<220> FEATURE:
<223> OTHER INFORMATION: CD3zeta

<400> SEQUENCE: 23

Gln Leu Pro Ile Thr Glu Ala Gln Ser Phe Gly Leu Leu Asp Pro Lys
1               5                   10                  15

Leu Cys Tyr Leu Leu Asp Gly Ile Leu Phe Ile Tyr Gly Val Ile Leu
                20                  25                  30

Thr Ala Leu Phe Leu Arg Val Lys Phe Ser Arg Ser Ala Asp Ala Pro
            35                  40                  45

Ala Tyr Gln Gln Gly Gln Asn Gln Leu Tyr Asn Glu Leu Asn Leu Gly
        50                  55                  60

Arg Arg Glu Glu Tyr Asp Val Leu Asp Lys Arg Arg Gly Arg Asp Pro

```
            65                  70                  75                  80
Glu Met Gly Gly Lys Pro Gln Arg Arg Lys Asn Pro Gln Glu Gly Leu
                    85                  90                  95

Tyr Asn Glu Leu Gln Lys Asp Lys Met Ala Glu Ala Tyr Ser Glu Ile
                100                 105                 110

Gly Met Lys Gly Glu Arg Arg Arg Gly Lys Gly His Asp Gly Leu Tyr
                115                 120                 125

Gln Gly Leu Ser Thr Ala Thr Lys Asp Thr Tyr Asp Ala Leu His Met
            130                 135                 140

Gln Ala Leu Pro Pro Arg
145                 150

<210> SEQ ID NO 24
<211> LENGTH: 48
<212> TYPE: DNA
<213> ORGANISM: Artificial Sequence
<220> FEATURE:
<223> OTHER INFORMATION: Ectodomain

<400> SEQUENCE: 24
cagctgccca tcaccgaggc tcaatccttt gggctgcttg atcctaag              48

<210> SEQ ID NO 25
<211> LENGTH: 64
<212> TYPE: DNA
<213> ORGANISM: Artificial Sequence
<220> FEATURE:
<223> OTHER INFORMATION: Transmembrane domain

<400> SEQUENCE: 25
ttgtgttatc ttcttgacgg catcctgttt atatacggtg tcattttgac agctctcttt    60
ctcc                                                                64

<210> SEQ ID NO 26
<211> LENGTH: 341
<212> TYPE: DNA
<213> ORGANISM: Artificial Sequence
<220> FEATURE:
<223> OTHER INFORMATION: Cytoplasmic domain

<400> SEQUENCE: 26
gagtcaagtt cagtcggtct gcagatgctc cagcatacca gcaaggccaa aatcagctgt    60
ataacgagtt gaaccttggg cgacgagaag aatacgacgt gcttgacaaa cgcagaggtc   120
gggaccctga atgggggt aagccgcaaa ggcggaagaa tccacaagag ggtctgtata    180
atgaattgca aaagacaag atggctgagg catactcaga gattggaatg aaggggaaa    240 gacggagggg aaagggccac gatgactgt accaagggct gagcaccgca actaaagata   300
catatgatgc tctgcacatg caggccctgc cacctagata a                      341

<210> SEQ ID NO 27
<211> LENGTH: 117
<212> TYPE: DNA
<213> ORGANISM: Artificial Sequence
<220> FEATURE:
<223> OTHER INFORMATION: Ectodomain

<400> SEQUENCE: 27
attgaagtta tgtatcctcc tccttaccta gacaatgaga agagcaatgg aaccattatc    60
catgtgaaag ggaaacacct tgtccaagt cccctatttc ccggaccttc taagccc       117
```

```
<210> SEQ ID NO 28
<211> LENGTH: 78
<212> TYPE: DNA
<213> ORGANISM: Artificial Sequence
<220> FEATURE:
<223> OTHER INFORMATION: Transmembrane domain

<400> SEQUENCE: 28
ttttgggtgc tggtggtggt tggtggagtc ctggcttgct atagcttgct agtaacagtg    60
gcctttatta ttttctgg                                                  78

<210> SEQ ID NO 29
<211> LENGTH: 468
<212> TYPE: DNA
<213> ORGANISM: Artificial Sequence
<220> FEATURE:
<223> OTHER INFORMATION: Cytoplasmic domain

<400> SEQUENCE: 29
gtgaggagta agaggagcag gctcctgcac agtgactaca tgaacatgac tccccgccgc    60
cccgggccca cccgcaagca ttaccagccc tatgccccac cacgcgactt cgcagcctat   120
cgctccagag tgaagttcag caggagcgca gacgcccccg cgtaccagca gggccagaac   180
cagctctata cgagctcaa tctaggacga agagaggagt acgatgtttt ggacaagaga   240
cgtggccggg accctgagat ggggggaaag ccgcagagaa ggaagaaccc tcaggaaggc   300
ctgtacaatg aactgcagaa agataagatg gcggaggcct acagtgagat tgggatgaaa   360
ggcgagcgcc ggaggggcaa ggggcacgat ggcctttacc agggtctcag tacagccacc   420
aaggacacct acgacgccct tcacatgcag gccctgcccc ctcgctaa               468

<210> SEQ ID NO 30
<211> LENGTH: 66
<212> TYPE: DNA
<213> ORGANISM: Artificial Sequence
<220> FEATURE:
<223> OTHER INFORMATION: G-S linker

<400> SEQUENCE: 30
tcctcagggg gcgggggaag tggtgggggc ggcagcggcg gaggggggctc aggaggaggc    60 ggatca                                                                66

<210> SEQ ID NO 31
<211> LENGTH: 1247
<212> TYPE: DNA
<213> ORGANISM: Artificial Sequence
<220> FEATURE:
<223> OTHER INFORMATION: CD64-VH domain-GS spacer-VL domain-CD3zeta
      complete

<400> SEQUENCE: 31
atgtggtttc ttactacatt gctgttgtgg gtcccggtgg acggtcaggt acaactgcag    60
cagtctggac ctgaactgaa gaagcctgga gagacagtca agatctcctg caaggcctct   120
gggtatcctt tcacaaacta tggaatgaac tgggtgaagc aggctccagg acagggttta   180
aagtggatgg gctggattaa cacctccact ggagagtcaa catttgctga tgacttcaag   240
ggacggtttg acttctcttt ggaaacctct gccaacactg cctatttgca gatcaacaac   300
ctaaaagtga agacagtgct acatatttct gtgcaagatg gaggtttac cacggctacg   360 ttccttactg gggccaaggg accacggtca ccgtttcctc ttcctcaggg ggcgggggaa   420
```

```
gtggtggggg cggcagcggc ggagggggct caggaggagg cggatcaggc ggatcagaca    480
tccagctgac ccagtctcac aaattcctgt ccacttcagt aggagacagg gtcagcatca    540
cctgcaaggc cagtcaggat gtgtataatg ctgttgcctg gtatcaacag aaaccaggac    600
aatctcctaa acttctgatt tactcggcat cctcccggta cactggagtc ccttctcgct    660
tcactggcag tggctctggg ccggatttca ctttcaccat cagcagtgtg caggctgaag    720
acctggcagt ttatttctgt cagcaacatt ttcgtactcc attcacgttc ggctcgggga    780
caaaattgga gatccagctg cccatcaccg aggctcaatc ctttgggctg cttgatccta    840
agttgtgtta tcttcttgac ggcatcctgt ttatatacgg tgtcattttg acagctctct    900
ttctccgagt caagttcagt cggtctgcag atgctccagc ataccagcaa ggccaaaatc    960
agctgtataa cgagttgaac cttgggcgac gagaagaata cgacgtgctt gacaaacgca   1020
gaggtcggga ccctgaaatg gggggtaagc cgcaaaggcg gaagaatcca caagagggtc   1080
tgtataatga attgcaaaaa gacaagatgg ctgaggcata ctcagagatt ggaatgaaag   1140
gggaaagacg gaggggaaag ggccacgatg gactgtacca agggctgagc accgcaacta   1200 agatacata tgatgctctg cacatgcagg ccctgccacc tagataa                 1247
```

<210> SEQ ID NO 32
<211> LENGTH: 415
<212> TYPE: PRT
<213> ORGANISM: Artificial Sequence
<220> FEATURE:
<223> OTHER INFORMATION: CD64-VH domain-GS spacer-VL domain-CD3zeta
      complete

<400> SEQUENCE: 32

```
Met Trp Phe Leu Thr Leu Leu Leu Trp Val Pro Val Asp Gly Gln
1               5                   10                  15

Val Gln Leu Gln Gln Ser Gly Pro Glu Leu Lys Lys Pro Gly Glu Thr
            20                  25                  30

Val Lys Ile Ser Cys Lys Ala Ser Gly Tyr Pro Phe Thr Asn Tyr Gly
        35                  40                  45

Met Asn Trp Val Lys Gln Ala Pro Gly Gln Gly Leu Lys Trp Met Gly
    50                  55                  60

Trp Ile Asn Thr Ser Thr Gly Glu Ser Thr Phe Ala Asp Asp Phe Lys
65                  70                  75                  80

Gly Arg Phe Asp Phe Ser Leu Glu Thr Ser Ala Asn Thr Ala Tyr Leu
                85                  90                  95

Gln Ile Asn Asn Leu Lys Ser Glu Asp Met Ala Thr Tyr Phe Cys Ala
            100                 105                 110

Arg Trp Glu Val Tyr His Gly Tyr Val Pro Tyr Trp Gly Gln Gly Thr
        115                 120                 125

Thr Val Thr Val Ser Ser Ser Gly Gly Gly Ser Gly Gly Gly
    130                 135                 140

Gly Ser Gly Gly Gly Ser Gly Gly Gly Ser Gly Gly Ser Asp
145                 150                 155                 160

Ile Gln Leu Thr Gln Ser His Lys Phe Leu Ser Thr Ser Val Gly Asp
                165                 170                 175

Arg Val Ser Ile Thr Cys Lys Ala Ser Gln Asp Val Tyr Asn Ala Val
            180                 185                 190

Ala Trp Tyr Gln Gln Lys Pro Gly Gln Ser Pro Lys Leu Leu Ile Tyr
        195                 200                 205

Ser Ala Ser Ser Arg Tyr Thr Gly Val Pro Ser Arg Phe Thr Gly Ser
```

```
                210                 215                 220
Gly Ser Gly Pro Asp Phe Thr Phe Thr Ile Ser Ser Val Gln Ala Glu
225                 230                 235                 240

Asp Leu Ala Val Tyr Phe Cys Gln Gln His Phe Arg Thr Pro Phe Thr
                245                 250                 255

Phe Gly Ser Gly Thr Lys Leu Glu Ile Gln Leu Pro Ile Thr Glu Ala
                260                 265                 270

Gln Ser Phe Gly Leu Leu Asp Pro Lys Leu Cys Tyr Leu Leu Asp Gly
                275                 280                 285

Ile Leu Phe Ile Tyr Gly Val Ile Leu Thr Ala Leu Phe Leu Arg Val
290                 295                 300

Lys Phe Ser Arg Ser Ala Asp Ala Pro Ala Tyr Gln Gln Gly Gln Asn
305                 310                 315                 320

Gln Leu Tyr Asn Glu Leu Asn Leu Gly Arg Arg Glu Glu Tyr Asp Val
                325                 330                 335

Leu Asp Lys Arg Arg Gly Arg Asp Pro Glu Met Gly Gly Lys Pro Gln
                340                 345                 350

Arg Arg Lys Asn Pro Gln Glu Gly Leu Tyr Asn Glu Leu Gln Lys Asp
                355                 360                 365

Lys Met Ala Glu Ala Tyr Ser Glu Ile Gly Met Lys Gly Glu Arg Arg
370                 375                 380

Arg Gly Lys Gly His Asp Gly Leu Tyr Gln Gly Leu Ser Thr Ala Thr
385                 390                 395                 400

Lys Asp Thr Tyr Asp Ala Leu His Met Gln Ala Leu Pro Pro Arg
                405                 410                 415

<210> SEQ ID NO 33
<211> LENGTH: 109
<212> TYPE: PRT
<213> ORGANISM: Artificial Sequence
<220> FEATURE:
<223> OTHER INFORMATION: SHIE2 light chain variable region

<400> SEQUENCE: 33

Gln Ser Ala Leu Thr Gln Pro Ala Ser Val Ser Gly Ser Leu Gly Gln
1               5                   10                  15

Ser Val Thr Ile Ser Cys Thr Gly Ser Ser Asp Val Gly Ser Tyr
                20                  25                  30

Asn Leu Val Ser Trp Tyr Gln Gln His Pro Gly Lys Ala Pro Asn Leu
                35                  40                  45

Met Ile Tyr Asp Val Ser Lys Arg Ser Gly Val Ser Asn Arg Phe Ser
50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Ser Ser Tyr Thr Gly Ile Ser
                85                  90                  95

Thr Val Val Phe Gly Gly Gly Thr Lys Leu Thr Val Leu
                100                 105

<210> SEQ ID NO 34
<211> LENGTH: 20
<212> TYPE: PRT
<213> ORGANISM: Artificial Sequence
<220> FEATURE:
<223> OTHER INFORMATION: linker

<400> SEQUENCE: 34
```

```
Gly Gly Gly Gly Ser Gly Gly Gly Ser Gly Gly Gly Ser Gly
1               5                   10                  15

Gly Gly Gly Ser
            20
```

<210> SEQ ID NO 35
<211> LENGTH: 119
<212> TYPE: PRT
<213> ORGANISM: Artificial Sequence
<220> FEATURE:
<223> OTHER INFORMATION: SHIE2 heavy chain variable region

<400> SEQUENCE: 35

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Tyr Tyr Tyr Tyr Met Asp Val Trp Gly Gln Gly
            100                 105                 110

Thr Thr Val Thr Val Ser Ser
        115
```

<210> SEQ ID NO 36
<211> LENGTH: 109
<212> TYPE: PRT
<213> ORGANISM: Artificial Sequence
<220> FEATURE:
<223> OTHER INFORMATION: RBSC6 light chain variable region

<400> SEQUENCE: 36

```
Asn Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Arg Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Ala Leu Thr Ile Ser Ser Leu Gln Pro
65                  70                  75                  80

Glu Asp Phe Ala Thr Tyr Tyr Cys Gln Gln Ala Asp Ser Arg Phe Ser
                85                  90                  95

Ile Thr Phe Gly Gln Gly Thr Arg Leu Glu Ile Lys Gly
            100                 105
```

<210> SEQ ID NO 37
<211> LENGTH: 118
<212> TYPE: PRT
<213> ORGANISM: Artificial Sequence
<220> FEATURE:
<223> OTHER INFORMATION: RBSC6 heavy chain variable region -continued

<400> SEQUENCE: 37

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Gln Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gly Asp Tyr Tyr Gly Met Asp Val Trp Gly Gln Gly Thr
            100                 105                 110

Thr Val Thr Val Ser Ser
        115

<210> SEQ ID NO 38
<211> LENGTH: 15
<212> TYPE: PRT
<213> ORGANISM: Artificial Sequence
<220> FEATURE:
<223> OTHER INFORMATION: CD64 leader signal sequence

<400> SEQUENCE: 38

Met Trp Phe Leu Thr Thr Leu Leu Leu Trp Val Pro Val Asp Gly
1               5                   10                  15

<210> SEQ ID NO 39
<211> LENGTH: 25
<212> TYPE: PRT
<213> ORGANISM: Artificial Sequence
<220> FEATURE:
<223> OTHER INFORMATION: G-S spacer

<400> SEQUENCE: 39

Ser Ser Gly Gly Gly Gly Ser Gly Gly Gly Ser Gly Gly Gly Gly
1               5                   10                  15

Ser Gly Gly Gly Gly Ser Gly Gly Ser
            20                  25

<210> SEQ ID NO 40
<211> LENGTH: 112
<212> TYPE: PRT
<213> ORGANISM: Artificial Sequence
<220> FEATURE:
<223> OTHER INFORMATION: Ganitumab light chain variable region

<400> SEQUENCE: 40

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Met Gln Gly
            85                  90                  95

Thr His Trp Pro Leu Thr Phe Gly Gln Gly Thr Lys Val Glu Ile Lys
            100                 105                 110
```

<210> SEQ ID NO 41
<211> LENGTH: 119
<212> TYPE: PRT
<213> ORGANISM: Artificial Sequence
<220> FEATURE:
<223> OTHER INFORMATION: Ganitumab heavy chain variable region

<400> SEQUENCE: 41

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Thr Asn Tyr Asn Pro Ser Leu
            50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Trp Thr Gly Arg Thr Asp Ala Phe Asp Ile Trp Gly Gln Gly
            100                 105                 110

Thr Met Val Thr Val Ser Ser
            115
```

<210> SEQ ID NO 42
<211> LENGTH: 107
<212> TYPE: PRT
<213> ORGANISM: Artificial Sequence
<220> FEATURE:
<223> OTHER INFORMATION: Cetuximab light chain variable region

<400> SEQUENCE: 42

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
            50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
            85                  90                  95

Thr Phe Gly Ala Gly Thr Lys Leu Glu Leu Lys
            100                 105
```

<210> SEQ ID NO 43
<211> LENGTH: 121
<212> TYPE: PRT
<213> ORGANISM: Artificial Sequence
<220> FEATURE:
<223> OTHER INFORMATION: Cetuximab heavy chain variable region

<400> SEQUENCE: 43

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Glu Thr Asn Ser Leu Gln Ser Asn Asp Thr Ala Ile Tyr Tyr
                85                  90                  95

Cys Ala Arg Ala Leu Thr Tyr Tyr Asp Tyr Glu Phe Ala Tyr Trp Gly
            100                 105                 110

Gln Gly Thr Leu Val Thr Val Ser Ala
        115                 120

<210> SEQ ID NO 44
<211> LENGTH: 125
<212> TYPE: PRT
<213> ORGANISM: Artificial Sequence
<220> FEATURE:
<223> OTHER INFORMATION: FRP5 heavy chain variable region

<400> SEQUENCE: 44

Gln Val Gln Leu Gln Gln Ser Gly Pro Glu Leu Lys Lys Pro Gly Glu
1               5                   10                  15

Thr Val Lys Ile Ser Cys Lys Ala Ser Gly Tyr Pro Phe Thr Asn Tyr
            20                  25                  30

Gly Met Glu Thr Asn Trp Val Lys Gln Ala Pro Gly Gln Gly Leu Lys
        35                  40                  45

Trp Met Glu Thr Gly Trp Ile Asn Thr Ser Thr Gly Glu Ser Thr Phe
    50                  55                  60

Ala Asp Asp Phe Lys Gly Arg Phe Asp Phe Ser Leu Glu Thr Ser Ala
65                  70                  75                  80

Asn Thr Ala Tyr Leu Gln Ile Asn Asn Leu Lys Ser Glu Asp Met Glu
                85                  90                  95

Thr Ala Thr Tyr Phe Cys Ala Arg Trp Glu Val Tyr His Gly Tyr Val
            100                 105                 110

Pro Tyr Trp Gly Gln Gly Thr Thr Val Thr Val Ser Ser
        115                 120                 125

<210> SEQ ID NO 45
<211> LENGTH: 106
<212> TYPE: PRT
<213> ORGANISM: Artificial Sequence
<220> FEATURE:
<223> OTHER INFORMATION: FRP5 light chain variable region

<400> SEQUENCE: 45

Asp Ile Gln Leu Thr Gln Ser His Lys Phe Leu Ser Thr Ser Val Gly
1               5                   10                  15

Asp Arg Val Ser Ile Thr Cys Lys Ala Ser Gln Asp Val Tyr Asn Ala
            20                  25                  30

Val Ala Trp Tyr Gln Gln Lys Pro Gly Gln Ser Pro Lys Leu Leu Ile
        35                  40                  45

Tyr Ser Ala Ser Ser Arg Tyr Thr Gly Val Pro Ser Arg Phe Thr Gly
            50                  55                  60

Ser Gly Ser Gly Pro Asp Phe Thr Phe Thr Ile Ser Ser Val Gln Ala
 65                  70                  75                  80

Glu Asp Leu Ala Val Tyr Phe Cys Gln Gln His Phe Arg Thr Pro Phe
                85                  90                  95

Thr Phe Gly Ser Gly Thr Lys Leu Glu Ile
            100                 105

<210> SEQ ID NO 46
<211> LENGTH: 109
<212> TYPE: PRT
<213> ORGANISM: Artificial Sequence
<220> FEATURE:
<223> OTHER INFORMATION: Trastuzumab heavy chain variable region

<400> SEQUENCE: 46

Asp Ile Gln Met Glu Thr Thr Gln Ser Pro Ser Ser Leu Ser Ala Ser
 1               5                  10                  15

Val Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys Leu
        35                  40                  45

Leu Ile Tyr Ser Ala Ser Phe Leu Tyr Ser Gly Val Pro Ser Arg Phe
    50                  55                  60

Ser Gly Ser Arg Ser Gly Thr Asp Phe Thr Leu Thr Ile Ser Ser Leu
 65                  70                  75                  80

Gln Pro Glu Asp Phe Ala Thr Tyr Tyr Cys Gln Gln His Tyr Thr Thr
                85                  90                  95

Pro Pro Thr Phe Gly Gln Gly Thr Lys Val Glu Ile Lys
            100                 105

<210> SEQ ID NO 47
<211> LENGTH: 124
<212> TYPE: PRT
<213> ORGANISM: Artificial Sequence
<220> FEATURE:
<223> OTHER INFORMATION: Trastuzumab light chain variable region

<400> SEQUENCE: 47

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Glu Thr Asn Ser Leu Arg Ala Glu Asp Thr Ala Val Tyr
                85                  90                  95

Tyr Cys Ser Arg Trp Gly Gly Asp Gly Phe Tyr Ala Met Glu Thr Asp
            100                 105                 110

Tyr Trp Gly Gln Gly Thr Leu Val Thr Val Ser Ser
        115                 120